(12) United States Patent
Whiteford et al.

(10) Patent No.: US 8,067,402 B2
(45) Date of Patent: *Nov. 29, 2011

(54) METHODS AND SYSTEMS FOR COATING AN ORAL SURFACE

(75) Inventors: Jeffery A. Whiteford, Belmont, CA (US); William P. Freeman, San Mateo, CA (US)

(73) Assignee: AllAccem, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/638,327

(22) Filed: Dec. 12, 2006

(65) Prior Publication Data

US 2007/0202342 A1 Aug. 30, 2007

Related U.S. Application Data

(60) Provisional application No. 60/749,540, filed on Dec. 12, 2005, provisional application No. 60/755,292, filed on Dec. 30, 2005, provisional application No. 60/756,401, filed on Jan. 5, 2006.

(51) Int. Cl.
  *A61K 31/33* (2006.01)
(52) U.S. Cl. ...................................... 514/183
(58) Field of Classification Search ................ None
  See application file for complete search history.

(56) References Cited

U.S. PATENT DOCUMENTS

| | | |
|---|---|---|
| 2,455,807 A | 12/1948 | Redmon et al. |
| 3,066,112 A | 11/1962 | Bowen |
| 3,179,623 A | 4/1965 | Bowen |
| 3,194,784 A | 7/1965 | Bowen |
| 3,751,399 A | 8/1973 | Lee et al. |
| 3,926,906 A | 12/1975 | Lee et al. |
| 4,321,268 A | 3/1982 | Scherm et al. |
| 4,544,359 A | 10/1985 | Waknine |
| 4,547,531 A | 10/1985 | Waknine |
| 4,666,896 A | 5/1987 | Warner, Jr. et al. |
| RE32,581 E | 1/1988 | Scherm et al. |
| 4,853,987 A | 8/1989 | Jaworski |
| 4,946,942 A | 8/1990 | Fuller et al. |
| 5,064,613 A | 11/1991 | Higgs et al. |
| 5,084,096 A | 1/1992 | Stovicek |
| 5,118,729 A | 6/1992 | Piechocki |
| 5,145,853 A | 9/1992 | Metzger et al. |
| 5,158,766 A | 10/1992 | Greenwald et al. |
| 5,212,318 A | 5/1993 | Buckland |
| 5,230,842 A | 7/1993 | Munde |
| 5,276,068 A | 1/1994 | Waknine |
| 5,344,856 A | 9/1994 | Klein |
| 5,348,988 A | 9/1994 | Suh et al. |
| 5,350,814 A | 9/1994 | McGarry et al. |
| 5,386,018 A | 1/1995 | Au et al. |
| 5,389,703 A | 2/1995 | Lee |
| 5,393,516 A | 2/1995 | Rheinberger et al. |
| 5,414,878 A | 5/1995 | Booth |
| 5,494,987 A | 2/1996 | Imazato et al. |
| 5,496,545 A | 3/1996 | Holmes-Farley et al. |
| 5,521,246 A | 5/1996 | Tien et al. |
| 5,534,565 A | 7/1996 | Zupancic et al. |
| 5,587,023 A | 12/1996 | Booth |
| 5,597,560 A | 1/1997 | Bergamini et al. |
| 5,602,193 A | 2/1997 | Stark |
| 5,658,994 A | 8/1997 | Burgoyne, Jr. et al. |
| 5,667,775 A | 9/1997 | Holmes-Farley et al. |
| 5,698,657 A | 12/1997 | Conner et al. |
| 5,703,231 A | 12/1997 | Randall et al. |
| 5,753,268 A | 5/1998 | Stolle et al. |
| 5,753,269 A | 5/1998 | Groh et al. |
| 5,824,734 A | 10/1998 | Yang |
| 5,874,516 A | 2/1999 | Burgoyne, Jr. et al. |
| 5,948,390 A | 9/1999 | Nelson et al. |
| 5,990,110 A | 11/1999 | Firestone |
| 6,008,313 A | 12/1999 | Walker et al. |
| 6,020,370 A | 2/2000 | Horwell et al. |
| 6,080,170 A | 6/2000 | Nash et al. |
| 6,187,248 B1 | 2/2001 | O'Neill et al. |
| 6,190,650 B1 | 2/2001 | Matthews et al. |
| 6,218,455 B1 | 4/2001 | Smith et al. |
| 6,235,811 B1 | 5/2001 | Robeson et al. |
| 6,242,526 B1 | 6/2001 | Siddiqui et al. |

(Continued)

FOREIGN PATENT DOCUMENTS

GB 599722 1/1947

(Continued)

OTHER PUBLICATIONS

March. Advanced Organic Chemistry, 1994, reaction 6-14, pp. 896-897.*
Dagayi et al. Methods of formation of the carbon-nitrogen double bond, chapter 2 of The chemistry of the carbon-nitrogen double bond, editor Saul Patai, 1970, pp. 61-69.*
"Substructure Search results", http://www.sigmaaldrich.com/catalog/search/substructure/SubstructureSearchPage, accessed Oct. 29, 2009.*
Bhattacharjee et al. Tetrahedron Letters, 1996, 37(20), pp. 3579-3580.*
Marcil, V. et.al. "Butyrate Impairs Lipid Transport by Inhibiting Microsomal Triglyceride Transfer Protein in Caco-2 Cells" J. Nutr. 2003, 133: 2180-2183.
Wren et al. "Dirlotapide: a review of its properties and role in the management of obesity in dogs" 2007 J. vet Pharmacol. Therap. 30 (Suppl. 1), 11-16.

(Continued)

*Primary Examiner* — Noble Jarrell
(74) *Attorney, Agent, or Firm* — Meyertons, Hood, Kivlin, Kowert & Goetzel, P.C.; Eric B. Meyertons

(57) ABSTRACT

A coating system and method are described. In some embodiments, a system may include a composition. The composition may include one or more bridged polycyclic compounds. At least one of the bridged polycyclic compounds may include at least two cyclic groups, and at least two of the cyclic groups may include quaternary ammonium moieties. In some embodiments, a method may include applying a coating to an oral surface. The coating may be antimicrobial. A coating may include antimicrobial bridged polycyclic compounds. Bridged polycyclic compounds may include quaternary ammonium compounds. Bridged polycyclic compounds based coating systems may impart self-cleaning properties to a surface (e.g., a tooth surface).

70 Claims, 2 Drawing Sheets

U.S. PATENT DOCUMENTS

| | | |
|---|---|---|
| 6,267,590 B1 | 7/2001 | Barry et al. |
| 6,268,126 B1 | 7/2001 | Neenan et al. |
| 6,309,221 B1 | 10/2001 | Jensen |
| 6,316,044 B2 | 11/2001 | Ottersbach et al. |
| 6,326,417 B1 | 12/2001 | Jia |
| 6,350,397 B1 | 2/2002 | Heikkila et al. |
| 6,416,546 B1 | 7/2002 | Kimura et al. |
| 6,436,419 B1 | 8/2002 | Sun et al. |
| 6,440,405 B1 | 8/2002 | Cooper et al. |
| 6,455,134 B1 | 9/2002 | Rabasco |
| 6,458,876 B1 | 10/2002 | Rabasco et al. |
| 6,464,971 B1 | 10/2002 | Matthews et al. |
| 6,465,042 B2 | 10/2002 | Saitoh et al. |
| 6,468,953 B1 | 10/2002 | Hitchems et al. |
| 6,492,445 B2 | 12/2002 | Siddiqui et al. |
| 6,500,004 B2 | 12/2002 | Jensen et al. |
| 6,538,143 B1 | 3/2003 | Pinschmidt, Jr. et al. |
| 6,562,329 B2 | 5/2003 | Hadvary et al. |
| 6,593,395 B2 | 7/2003 | Angeletakis et al. |
| 6,608,131 B1 | 8/2003 | Winterowd et al. |
| 6,617,142 B2 | 9/2003 | Keogh et al. |
| 6,632,291 B2 | 10/2003 | Rabon et al. |
| 6,716,955 B2 | 4/2004 | Burgoyne, Jr. |
| 6,720,368 B2 | 4/2004 | Field |
| 6,756,364 B2 | 6/2004 | Barbier et al. |
| 6,803,077 B2 | 10/2004 | Yu |
| 6,858,203 B2 | 2/2005 | Holmes-Farley et al. |
| 6,887,517 B1 | 5/2005 | Cook et al. |
| 6,900,265 B2 | 5/2005 | Schultz et al. |
| 6,908,609 B2 | 6/2005 | Simon et al. |
| 6,924,325 B2 | 8/2005 | Qian |
| 6,929,705 B2 | 8/2005 | Meyers et al. |
| 6,936,640 B2 | 8/2005 | McQueen et al. |
| 7,014,846 B2 | 3/2006 | Holmes-Farley et al. |
| 7,314,857 B2 | 1/2008 | Madhyastha |
| 7,342,083 B2 | 3/2008 | Chang et al. |
| 7,385,012 B2 | 6/2008 | Chang et al. |
| 7,713,955 B2 | 5/2010 | Whiteford et al. |
| 2001/0009931 A1 | 7/2001 | Pflug et al. |
| 2002/0151570 A1 | 10/2002 | Kretschik et al. |
| 2002/0177828 A1 | 11/2002 | Batich et al. |
| 2003/0091641 A1 | 5/2003 | Tiller et al. |
| 2003/0134933 A1 | 7/2003 | Jin et al. |
| 2003/0149149 A1 | 8/2003 | Carlisle et al. |
| 2003/0175659 A1 | 9/2003 | Tiba et al. |
| 2003/0190820 A1 | 10/2003 | Hill et al. |
| 2003/0199605 A1 | 10/2003 | Fischer |
| 2004/0092896 A1 | 5/2004 | Thompson |
| 2004/0199994 A1 | 10/2004 | Sherif et al. |
| 2004/0267009 A1 | 12/2004 | Redko et al. |
| 2005/0008763 A1 | 1/2005 | Schachter |
| 2005/0008777 A1 | 1/2005 | McCleskey et al. |
| 2005/0118911 A1 | 6/2005 | Oles et al. |
| 2005/0129937 A1 | 6/2005 | Patton et al. |
| 2005/0158252 A1 | 7/2005 | Romanowski et al. |
| 2005/0175966 A1 | 8/2005 | Falsafi et al. |
| 2005/0208249 A1 | 9/2005 | Wen et al. |
| 2005/0249818 A1 | 11/2005 | Sawan et al. |
| 2005/0252413 A1 | 11/2005 | Kangas et al. |
| 2005/0256223 A1 | 11/2005 | Kolb et al. |
| 2005/0265931 A1 | 12/2005 | Qian |
| 2005/0271780 A1 | 12/2005 | Schroeder et al. |
| 2007/0202342 A1 | 8/2007 | Whiteford et al. |
| 2008/0020127 A1 | 1/2008 | Whiteford et al. |
| 2008/0021212 A1 | 1/2008 | Whiteford et al. |
| 2008/0207581 A1 | 8/2008 | Whiteford et al. |
| 2008/0275141 A1 | 11/2008 | Whiteford |
| 2009/0054528 A1 | 2/2009 | Whiteford |
| 2009/0069435 A1 | 3/2009 | Whiteford |
| 2009/0074833 A1 | 3/2009 | Whiteford |
| 2009/0105262 A1 | 4/2009 | Whiteford |
| 2009/0270005 A1 | 10/2009 | Takahashi et al. |
| 2010/0004218 A1 | 1/2010 | Whiteford |
| 2010/0016270 A1 | 1/2010 | Whiteford |
| 2011/0015300 A1* | 1/2011 | Whiteford et al. ............ 523/122 |

FOREIGN PATENT DOCUMENTS

| | | |
|---|---|---|
| JP | 2005154379 | 6/2005 |
| WO | 2007/029855 | 3/2007 |
| WO | 2007/070801 | 6/2007 |
| WO | 2008/103847 | 8/2008 |

OTHER PUBLICATIONS

Hussain, M. M. et.al. "Microsomal triglyceride transfer protein and its role inapoB-lipoprotein assembly" Journal of Lipid Research, 2003, vol. 44, 22-32.

Ni, B. et al. "Design and Synthesis of Pyridinium Chiral Ionic Liquids Tethered to a Urea Functionality", J. Org. Chem. 2006, 71, 26, 9857-9860.

Curd, F. H. S. et al. "Synthetic Antimalarials, Part X, Some Aryldiguanide (-biguanide) Derivatives" J. Chem. Soc. 729-737 (1946).

Chandler, C.E. et al. "CP-346086: an MTP inhibitor that lowers plasma cholesterol and triglycerides in experimental animals and in humans" Journal of Lipid Research, vol. 44, 1887-1901, Oct. 2003.

Curd, F. H. S. et al. "Synthetic Antimalarials, Part XXVIII, an alternative route to N1-aryl-N5-alkyldiguanides" J. Chem. Soc. 1630-1636 (1948).

Co-Pending U.S. Appl. No. 12/035,351 entitled, "Bridged Polycyclic Compound Based Compositions for the Inhibition and Amelioration of Disease" to Whiteford filed Feb. 21, 2008.

Hossain, M. A. et al. "Parallels in Cation and Anion Coordination: A New Class of Cascade Complexes" Angew. Chem. Int. Ed., vol. 41, No. 13, 2335-2338, 2002.

Chen, Q. Y. et al. "Synthesis, crystal structure and properties of the first trinuclear copper(II) cryptate bridged by an imidazole anion" J. Chem. Soc., Dalton Trans., 1315-1318, 2002.

Chen, Q. Y. et al. "A study on the heterodinuclear cryptates [LnCuL(DMF)](ClO4)2•MeCN (Ln = Gd, Eu, Tb, Dy, Y)—synthesis, characterization, magnetic and electrochemical properties" J. Chem. Soc., Dalton Trans., 2873-2878, 2002.

Kang, S. G. et al. "Template Synthesis and Crystal Structure of a Novel Mononuclear Nickel(II) Complex with a Face-ti-Face Bis(macrocyclic) Ligand" Inorg. Chem., vol. 36, No. 11, 2478-2481, 1997.

Conejo-Garcia, A. et al. "Synthesis and NMR Studies on a C3-Symmetrical Triquinolina Triscationic Bicyclophane" J. Org. Chem., vol. 70, 5748-5751, 2005.

Shintani, H. "Modification of Medical Device Surface to attain Anti-Infection" Trends Biomater. Artif. Organs, vol. 18 (1), 1-8, 2004.

Kickelbick, G. "Concepts for the incorporation of inorganic building blocks into organic polymers on a nanoscale" Prog. Polym. Sci., vol. 28, 83-114, 2003.

Kull, F. C. et al. "Mixtures of Quaternary Ammonium Compounds and Long-chain Fatty Acids as Antifungal Agents" Appl. Microbiol., vol. 9, No. 6, 538-541, 1961.

Skold, K. et al. "Effect of a chlorhexidine/thymol-containing varnish on prostaglandin E2 levels in gingival crevicular fluid" Eur. J. Oral Sci.., vol. 106, 571-575, 1998.

Chand, D. K. et al. "Synthesis of a Heteroditopic Cryptand Capable of Imposing a Distorted Coordination Geometry onto Cu(II): Crystal Structures of the Cryptand (L), [Cu(L)(CN)](picrate), and [Cu(L)(NCS)]{picrate} and Spectroscopic Studies of the Cu(II) Complexes" Inorg. Chem., 1996, vol. 35, 3380-3387.

Chen, C. Z. et.al. "Quaternary Ammonium Functionalized Poly(propylene imine) Dendrimers as Effective Antimicrobials: Structure-Activity Studies" Biomacromolecules, 2000, vol. 1, No. 3, 473 -480.

Cunliffe, D. et al., "Bacterial Adhesion at Synthetic Surfaces" Applied and Environmental Microbiology, Nov. 1999, vol. 65, No. 11, 4995-5002.

Dibrov, P. et al. "Chemiosmotic Mechanism of Antimicrobial Activity of Ag+ in Vibrio cholerae" Antimicrobial Agents and Chemotherapy, Aug. 2002, vol. 46, No. 8, 2668-2670.

Drew, M. G. B. et al., "d10 Cations within triple-helical cryptand hosts; a structural and modelling study" J. Chem. Soc., Dalton Trans., 2000, 1513-1519.

Gibb, B. C. "Strict Self-Assembly and Self-Assembly with Covalent Modifications" Encyclopedia of Supramolecular Chemistry, Aug. 17, 2004, 1372-1378, DOI: 10.1081/E-ESMC-120012781.

Gomez, R. et al., "Synthesis, characterization and photocativity of nanosized sol-gel TiO2-ZrO2 mixed oxides." The 13th International Congress on Catalysis, Jul. 10-15, 2004.

Han, S. et al., "Low-Temperature Synthesis of Highly Crystalline TiO2 Nanocrystals and their Application to Photocatalysis" Small, 2005, vol. 1, No. 8-9, 812-816.

Huang, J. et al., "Thermomechanical properties of polyimide-epoxy nanocomposites from cubic silsesquioxane epoxides" J. Mater. Chem., 2004, vol. 14, 2858-2863.

Imhof, A. "Preparation and Characterization of Titania-Coated Polystyrene Spheres and Hollow Titania Shells" Langmuir, 2001, vol. 17, 3579-3585.

Kraft, A. et al. "Electroluminescent Conjugated Polymers-Seeing Polymers in a New Light" Angew. Chem. Int. Ed., 1998, vol. 37, 402-428.

Lawrence, N. J. et al., "Polymethylhydrosiloxane: a versatile reducing agent for organic synthesis" J. Chem. Soc., Perkin Trans. 1, 1999, 3381-3391.

Lin, J. et al. "Insights into bactericidal action of surface-attached poly(vinyl-N-hexylpyridinium) chains" Biotechnology Letters, 2002, vol. 24, 801-805.

Lin, J. et al. "Making thin polymeric materials, including fabrics, microbicidal and also water-repellent" Biotechnology Letters, 2003, vol. 25, 1661-1665.

Maness, P. et al. "Bactericidal Activity of Photocatalytic TiO2 Reaction: toward an Understanding of Its Killing Mechanism" Applied and Environmental Microbiology, Sep. 1999, vol. 65, No. 9, 4094-4098.

Marlin, D. S. et al. "Complexation-Induced Translational Isomerism: Shuttling through Stepwise Competitive Binding" Angewandte Chemie, 2006, vol. 45, pp. 77-83.

Ming, W. et al., "Superhydrophobic Films from Raspberry-like Particles" Nano. Lett, Oct. 1, 2005, vol. 5, No. 11, 2298 -2301.

Pernak, J. et al., "Synthesis and anti-microbial activities of some pyridinium salts with alkoxymethyl hydrophobic group" Eur. J. Med. Chem., 2001, vol. 36, 899-907.

Rivas, F. M. et al. "Aromatic Amination/Imination Approach to Chiral Benzimidazoles" J. Org. Chem., 2002, vol. 67, 1708-1711.

Rowan, S. J. et al. "Dynamic Covalent Chemistry" Angew Chem Int Ed Engl., 2002, vol. 41, No. 6, 898-952.

Salvatore, R. N. et al., "Synthesis of secondary amines" Tetrahedron, 2001, vol. 57, 7785-7811.

Schweizer, H. P. "Efflux as a mechanism of resistance to antimicrobials in Pseudomonas aeruginosa and related bacteria: unanswered questions" Genetics and Molecular Research, Mar. 31, 2003, vol. 2, No. 1, 48-62.

Slack, J. M. et al. "Identification of Actinomyces and Related Bacteria in Dental Calculus by the Fluorescent Antibody Technique" J. Dent. Res., 1971, vol. 50, No. 1, 78-82.

Strachan, J. "Synthesis and Characterization of Tetrachlorodiarylethyne-Linked Porphyrin dimers. Effects of Linker Architecture on Intradimer Electronic Communication" Inorg. Chem., 1998, vol. 37, 1191-1201.

Thorsteinsson, T. et.al. "Soft Antimicrobial Agents: Synthesis and Activity of Labile Environmentally Friendly Long Chain Quaternary Ammonium Compounds" J. Med. Chem., 2003, vol. 46, 4173-4181.

Tiller, J. C. et al. "Designing surfaces that kill bacteria on contact" PNAS, 2001, vol. 98, No. 11, 5981-5985.

Tom, R. T. et al., "Freely Dispersible Au@TiO2, Au@ZrO2, Ag@TiO2, and Ag@ZrO2 Core-Shell Nanoparticles: One-Step Synthesis, Characterization, Spectroscopy, and Optical Limiting Properties" Langmuir, 2003, vol. 19, 3439-3445.

Trentler, T. J. et al., "Epoxy Resin-Photopolymer Composites for Volume Holography" Chem. Mater., 2000, vol. 12, 1431-1438.

Waschinski, C. J. et al. "Poly(oxazoline)s with Telechelic Antimicrobial Functions" Biomacromolecules, 2005, vol. 6, 235-243.

Zhang, X. "From Supramolecular Vanadate Receptors to Enzyme Models of Vanadium Haloperoxidase" Philosophisch-Naturwissenschaftlichen Fakultät der Universität Basel, Feb. 2005.

Zhisheng, C. et al "Recent Advances in Antimicrobial Dendrimers", Advanced Materials 2000, vol. 12, No. 11, 843-846.

International Search Report and Written Opinion for PCT/US06/61936 mailed Sep. 12, 2007.

Co-Pending U.S. Appl. No. 11/800,052 entitled, "Methods and Systems for Coating a Surface" to Whiteford et al. filed May 2, 2007.

Co-Pending U.S. Appl. No. 11/800,066 entitled, "Methods and Systems for Coating a Medical Device" to Whiteford et al. filed May 2, 2007.

Co-Pending U.S. Appl. No. 11/800,069 entitled, "Methods and Systems for Preparing an Antimicrobial Composition" to Whiteford et al. filed May 2, 2007.

Co-Pending U.S. Appl. No. 12/228,262 entitled, "Bridged Polycyclic Compound Based Compositions for Coating Oral Surfaces in Pets" to Whiteford filed Aug. 11, 2008.

Co-Pending U.S. Appl. No. 12/228,263 entitled, "Bridged Polycyclic Compound Based Compositions for Coating Oral Surfaces in Humans" to Whiteford filed Aug. 11, 2008.

Co-Pending U.S. Appl. No. 12/228,264 entitled, "Bridged Polycyclic Compound Based Compositions for Topical Applications for Pets" to Whiteford filed Aug. 11, 2008.

Co-Pending U.S. Appl. No. 12/193,529 entitled, "Bridged Polycyclic Compound Based Compositions for Controlling Bone Resorption" to Whiteford filed Aug. 18, 2008.

Zhuang, X.-M. et al. "Cyanide and imidazolate bridged macrocyclic dinuclear CuII complexes: Synthesis, structure and magnetic properties" Inorganica Chimica Acta 358 (2005) 2129-2134.

Pierre, J. L. et al. "Synthesis of a Novel Macrobicyclic Cavity Possessing Six Convergent Hydroxyl Groups and Acting as a Siderophore" Angew. Chem. Int. Ed. Engl. 30 (1991) No. 1, 85-86.

Shin, C. et al. "Novel Synthesis of the Main Central 2,3,6-Trisubstituted Pyridine Skeleton [Fragment A-B-C] of a Macrobicyclic Antibiotic, Cyclothiazomycin" Bull. Chem. Soc. Jpn. 75, (2002) 1583-1596.

International Search Report and Written Opinion for PCT/US2008/054611 mailed Oct. 7, 2008.

Dirksen, A. et al. "Nucleophilic Catalysis of Oxime Ligation" Angew. Chem. Int. Ed. (2006) 45, 7581-7584.

Co-Pending U.S. Appl. No. 12/488,269 entitled, "Bridged Polycyclic Compound Based Compositions for Controlling Cholesterol Levels" to Whiteford filed Jun. 19, 2009.

Co-Pending U.S. Appl. No. 12/488,281 entitled, "Bridged Polycyclic Compound Based Compositions for Renal Therapy" to Whiteford filed Jun. 19, 2009.

Chen, D. et al. "The synthesis of new binucleating polyaza macrocyclic and macrobicyclic ligands: dioxygen affinities of the cobalt complexes" Tetrahedron, vol. 47, Issue 34, Aug. 19, 1991, 6895-6902.

Rosenbaum, D. P. et al. "Effect of RenaGel, a non-absorbable, cross-linked, polymeric phosphate binder, on urinary phosphorus excretion in rats" Nephrol Dial Transplant, (1997) 12, 961-965.

Chertow, G. M. et al. "Poly[allylamine hydrochloride] (RenaGel): a noncalcemic phosphate binder for the treatment of hyperphosphatemia in chronic renal failure" Am J Kidney Dis., (1997), 29, 66-71.

David, S. A. et al. "Towards a rational development of anti-endotoxin agents: novel approaches to sequestration of bacterial endotoxins with small molecules" J. Mol. Recognit. (2001); 14: 370-387.

http://www.bio.brandeis.edu/classes/biochem104/hydrophobic_effect.pdf, May 24, 2010.

International Preliminary Report on Patentability for PCT/US06/61936 mailed Jun. 9, 2009.

International Search Report and Written Opinion for PCT/US2009/053464 mailed Feb. 2, 2010.

Written Opinion for European Application No. 08 730 417.6-1216 mailed Aug. 5, 2010.

Office Action for U.S. Appl. No. 11/800,052 mailed on Mar. 5, 2009.

Office Action for U.S. Appl. No. 11/800,052 mailed on Oct. 29, 2009.

Office Action for U.S. Appl No. 11/800,069 mailed on Aug. 18, 2009.

Office Action for U.S. Appl. No. 11/800,069 mailed on Mar. 22, 2010.

Advisory Action for U.S. Appl. No. 11/800,069 mailed on Jun. 9, 2010.

Office Action for U.S. Appl. No. 12/035,351 mailed on Aug. 5, 2010.
Co-Pending U.S. Appl. No. 12/775,277 entitled, "Methods and Systems for Coating a Surface" to Whiteford et al. filed May 6, 2010.
Examination Report for Patent Application No. 569756 mailed Feb. 26, 2010.
http://www.bio.brandeis.edu/classes/biochem104/hydrophobic_effect.pdf.
Examination Report for New Zealand Patent Application No. 579785 mailed Oct. 8, 2010. pp. 2.
Bhattacharjee, M. et al. "Synthesis of a New Macrocyclic Ligand with Six Amide Receptor Sites" Tetrahedron Letters (1996) vol. 37, No. 20, 3579-3580.
Office Action for U.S. Appl. No. 11/638,327 mailed on Jan. 20, 2011.
Office Action for U.S. Appl. No. 11/800,069 mailed on Jan. 6, 2011.
Final Office Action for U.S. Appl. No. 12/035,351 mailed on Feb. 3, 2011.
Non-Final Office Action for U.S. Appl. No. 12/228,262 mailed on Mar. 31, 2011.
International Preliminary Report on Patentability for PCT/US2009/053464 mailed Feb. 24, 2011.
Non-Final Office Action for U.S. Appl. No. 12/228,263 mailed on Mar. 31, 2011.
Non-Final Office Action for U.S. Appl. No. 12/228,264 mailed on Mar. 31, 2011.
Final Office Action for U.S. Appl. No. 11/638,327 mailed on Jul. 11, 2011.
Advisory Action for U.S. Appl. No. 12/035,351 mailed on May 20, 2011.
Non-Final Office Action for U.S. Appl. No. 12/193,529 mailed on May 27, 2011.
http://www.bio.brandeis.edu/classes/biochem104/hydrophobic_effect.pdf, Aug. 19, 2011.
International Search Report and Written Opinion for PCT/US2009/053464 mailed Feb. 2, 2010.
Non-Final Office Action for U.S. Appl. No. 11/800,066 mailed on Aug. 1, 2011.
Final Office Action for U.S. Appl. No. 11/800,069 mailed on Sep. 16, 2011.
Examination Report for New Zealand Patent Application No. 579785 mailed Aug. 1, 2011, p. 2.

* cited by examiner

METHODS AND SYSTEMS FOR COATING AN ORAL SURFACE

PRIORITY CLAIM

This application claims priority to U.S. Provisional Patent Application No. 60/749,540 entitled "ANTIMICROBIAL FILMS AND COATINGS" filed on Dec. 12, 2005, U.S. Provisional Patent Application No. 60/755,292 entitled "ANTI-MICROBIAL AND/OR SELF-CLEANING FILMS" filed on Dec. 30, 2005, and U.S. Provisional Patent Application No. 60/756,401 entitled "METHODS AND SYSTEMS FOR PREPARING ANTIMICROBIAL COATINGS" filed on Jan. 5, 2006, all of which are incorporated by reference herein.

BACKGROUND OF THE INVENTION

1. Field of the Invention

The present disclosure generally relates to self-cleaning and/or antimicrobial compositions. More particularly, the disclosure generally relates to systems and methods for the customizable formation of antimicrobial compositions. Further, the disclosure generally relates to systems and methods for preparation of films and coatings using the prepared antimicrobial compositions.

2. Description of the Relevant Art

Bacteria exist in a variety of locations—in water, soil, plants, animals, and humans. Bacteria may transfer from person to person, among animals and people, from animals to animals, and through water and the food chain. Most bacteria do little or no harm, and some are even useful to humans. However, others are capable of causing disease. The same bacteria may have different effects on different parts of the host body. For example, *S. aureus* on the skin may be generally harmless, but when they enter the bloodstream they may cause disease.

An antimicrobial may be generally defined as anything that may kill or inhibit the growth of microbes (e.g., high heat or radiation or a chemical). Microbes may be generally defined as a minute life form, a microorganism, especially a bacterium that causes disease. Antimicrobials may be grouped into three broad categories: antimicrobial drugs, antiseptics, and disinfectants. Antimicrobial drugs may be used in relatively low concentrations in or upon the bodies of organisms to prevent or treat specific bacterial diseases without harming the organism. They are also used in agriculture to enhance the growth of food animals. Unlike antimicrobial drugs, antiseptics and disinfectants are usually nonspecific with respect to their targets—they kill or inhibit a variety of microbes. Antiseptics may be used topically in or on living tissue. Disinfectants may be used on objects or in water.

Antimicrobial resistance may be generally described as a feature of some bacteria that enables them to avoid the effects of antimicrobial agents. Bacteria may possess characteristics that allow them to survive a sudden change in climate, the effects of ultraviolet light from the sun, and/or the presence of an antimicrobial chemical in their environment. Some bacteria are naturally resistant. Other bacteria acquire resistance to antimicrobials to which they once were susceptible.

The development of resistance to an antimicrobial is complex. Susceptible bacteria may become resistant by acquiring resistance genes from other bacteria or through mutations in their own genetic material (DNA). Once acquired, the resistance characteristic is passed on to future generations and sometimes to other bacterial species.

Antimicrobials have been shown to promote antimicrobial resistance in at least three ways: through (1) encouraging the exchange of resistant genes between bacteria, (2) favoring the survival of the resistant bacteria in a mixed population of resistant and susceptible bacteria, and (3) making people and animals more vulnerable to resistant infection. Although the contribution of antimicrobials in promoting resistance has most often been documented for antimicrobial drugs, there are also reports of disinfectant use contributing to resistance and concerns about the potential for antiseptics to promote resistance. For example, in the case of disinfectants, researchers have found that chlorinated river water contains more bacteria that are resistant to streptomycin than does non-chlorinated river water. Also, it has been shown that some kinds of *Escherichia coli* (*E. coli*) resist triclosan (an antiseptic used in a variety of products, including soaps and toothpaste). This raises the possibility that antiseptic use could contribute to the emergence of resistant bacteria.

While antimicrobials are a major factor in the development of resistance, many other factors are also involved, including for example the nature of the specific bacteria and antimicrobial involved, the way the antimicrobial is used, characteristics of the host, and environmental factors. Therefore, the use of antimicrobials does not always lead to resistance.

The *Staphylococcus aureus* bacterium (*S. aureus*), one of the most common causes of infections worldwide, has long been considered treatable with antimicrobial drugs. Recently, however, a number of *S. aureus* infections were found that resisted most available antimicrobials, including vancomycin, the last line of treatment for these and some other infections. For example, several years ago in Japan, a four-month-old infant who had developed an *S. aureus* infection following surgery, died after a month of treatments with various antimicrobials, including vancomycin. About a year later, three elderly patients in the United States with multiple chronic conditions were infected with this type of *S. aureus*, now known as vancomycin intermediate-resistant *Staphylococcus aureus* (VISA). They were treated with numerous antimicrobials for an extended period of time and eventually died, but it is unclear what role VISA played in their deaths. More recently, a middle-aged cancer patient in Hong Kong was admitted to a hospital with a fever and died despite two weeks of treatment for VISA.

Antimicrobials are recognized as major contributors in the development of antimicrobial resistance. There are many kinds of antimicrobials, varying in how they are used and in the agencies that have jurisdiction over them. The EPA is in fact conducting a reexamination of all pesticides (and antimicrobials), which received regulatory approval before 1984. In addition, the World Health Organization (WHO) has also repositioned itself to deal with this issue.

The causes for antimicrobial resistance are believed to be multi-factoral. In the case of antibiotics, it has been well documented that resistance is mainly caused by continued over reliance on and imprudent use of these antimicrobial agents. Increasing evidence is being obtained suggesting that the same may be true for the emergence of biocide resistance. There is increasing concern about possible cross-resistance of antibiotics and biocides due to common resistance mechanisms. The consequence of continued exposure to antimicrobials is an increase of bacteria that are intrinsically resistant to antimicrobials or have acquired resistance mechanisms to these substances.

Bacterial resistance mechanisms have been mostly determined for antibiotics and include: 1) exclusion from the cell (e.g., by the outer membrane); 2) enzymatic inactivation; 3) target alterations; and 4) active efflux from the cell. Similar resistance mechanisms are also involved in biocide resistance. Although exclusion from the cell due to reduced outer membrane impermeability was thought to play a key role in the intrinsic resistance of several common bacteria (e.g., *P. aeruginosa*) to many antimicrobial compounds, this is now attributed to synergy between a low-permeability outer membrane and active efflux from the cell. Some bacteria promote acquired multi-drug resistance as a consequence of hyper expression of the efflux genes by mutational events. In addition to antibiotics, these pumps export biocides, dyes, detergents, metabolic inhibitors, organic solvents and molecules involved in bacterial cell-cell communication. A discussion of mechanisms of antimicrobial resistance may be found in Schweizer "Efflux as a mechanism of resistance to antimicrobials in *Pseudomonas aeruginosa* and related bacteria: unanswered questions" *Genet. Mol. Res.,* 2(1): 48-62 (Mar. 31, 2003), which is incorporated by reference as if fully set forth herein.

Concern about possible cross-resistance of antibiotics and biocides due to common resistance mechanisms may be further accentuated when the mechanism of several different antimicrobials are compared. For example, the antimicrobial effects of silver salts have been noticed since ancient times, and today, silver is used to control bacterial growth in a variety of applications, including dental work, catheters, and burn wounds. Added at high (i.e., millimolar) concentrations, $Ag^+$ ions inhibit a number of enzymatic activities, reacting with electron donor groups, especially sulfhydryl groups. However, research in the past few years of the molecular mechanism of the bactericidal effect of much lower (e.g., micromolar) concentrations of $Ag^+$ ions points toward a different mechanism.

The addition of low micromolar concentrations of $Ag^+$ to inside-out membrane vesicles of *V. cholerae* induced a total collapse of both $\Delta pH$ and $\Delta \psi$ irrespective of the presence of $Na^+$ ions. This effect of $Ag^+$ was independent of the presence of the $Na^+$-translocating NQR, known as a specific target for submicromolar $Ag^+$, suggesting that the other $Ag^+$-modified membrane proteins (or perhaps the $Ag^+$-modified phospholipid bilayer itself) may cause the $H^+$ leakage, thus explaining the broad spectrum of the antimicrobial activity of $Ag^+$ ions. It is conceivable that the bactericidal action of these concentrations of $Ag^+$ in *V. cholerae* is not mediated by a specific target but is due to the $H^+$ leakage occurring through virtually any $Ag^+$-modified membrane protein or perhaps through the $Ag^+$-modified phospholipid bilayer itself. In the absence of $Ag^+$ resistance determinants (encoding pumps capable of efficient expelling of the $Ag^+$ ion), this would result in a complete deenergization of the membrane. Taking into account the well-documented crucial importance of the transmembrane proton gradient in overall microbial metabolism, it seems inevitable that the protonophore-like effect of $Ag^+$ described here should result in cell death. A discussion of the antimicrobial properties of silver may be found in Dibrov et al. "Chemiosmotic Mechanism of Antimicrobial Activity of $Ag^+$ in *Vibrio cholerae*" ANTIMICROBIAL AGENTS AND CHEMOTHERAPY, August 2002, p. 2668-2670, which is incorporated by reference as if fully set forth herein.

The antimicrobial effects of titanium dioxide have been known for quite some time and it is used to control bacteria activity. When titanium dioxide ($TiO_2$) is irradiated with near-UV light, this semiconductor exhibits strong bactericidal activity. Evidence has been presented that appears to show that the lipid peroxidation reaction is the underlying mechanism of death of *Escherichia coli* K-12 cells that are irradiated in the presence of the $TiO_2$ photocatalyst. Using production of malondialdehyde (MDA) as an index to assess cell membrane damage by lipid peroxidation, it was observed that there was an exponential increase in the production of MDA, whose concentration reached 1.1 to 2.4 nmol·mg (dry weight) of cells$^{-1}$ after 30 min of illumination, and that the kinetics of this process paralleled cell death. Under these conditions, concomitant losses of 77 to 93% of the cell respiratory activity were also detected, as measured by both oxygen uptake and reduction of 2,3,5-triphenyltetrazolium chloride from succinate as the electron donor. The occurrence of lipid peroxidation and the simultaneous losses of both membrane-dependent respiratory activity and cell viability depended strictly on the presence of both light and $TiO_2$. It was theorized that $TiO_2$ photocatalysis promoted peroxidation of the polyunsaturated phospholipid component of the lipid membrane initially and induced major disorder in the *E. coli* cell membrane. Subsequently, essential functions that rely on intact cell membrane architecture, such as respiratory activity, were lost, and cell death was inevitable. A discussion of the antimicrobial properties of titanium dioxide may be found in Maness et al. "Bactericidal Activity of Photocatalytic $TiO_2$ Reaction: toward an Understanding of Its Killing Mechanism" APPLIED AND ENVIRONMENTAL MICROBIOLOGY, September 1999, p. 4094-4098, which is incorporated by reference as if fully set forth herein.

Phenol and its derivatives exhibit several types of bactericidal action. At higher concentrations, the compounds penetrate and disrupt the cell wall and precipitate cell proteins. Generally, gram-positive bacteria are more sensitive than gram-negative bacteria, which in turn are more sensitive than mycobacteria. The initial reaction between a phenolic derivative and bacteria involves binding of the active phenol species to the cell surface. Once the active has bound to the exterior of the cell, it needs to penetrate to its target sites-either by passive diffusion (gram-positive) or by the hydrophobic lipid bilayer pathway (gram-negative). One of the initial events to occur at the cytoplasmic membrane is the inhibition of membrane bound enzymes. The next level in the damage to the cytoplasmic membrane is the loss in the membrane's ability to act as a permeability barrier. There is limited information regarding the action of phenolics against viruses. The molecular mechanisms probably do not differ from those that occur in bacteria. Phenols act at the germination stage of bacterial spore development; however, this effect is reversible-therefore the sporicidal activity of phenolic compounds is low. As with many disinfectants, the activity of phenols is highly formulation dependant and affected by factors such as temperature, concentration, pH and the presence of organic matter.

Although the mode of action of quaternary ammonium compounds has not yet been completely described in detail, there are definitive explanations of the antimicrobial mode of action of cationic disinfectants in general.

One of the main considerations in examining the mode of action is the characterization of quaternary ammonium compounds as cationic surfactants. This class of chemical reduces the surface tension at interfaces, and is attracted to negatively charged surfaces, including microorganisms. Quaternary ammonium compounds denature the proteins of the bacterial or fungal cell, affect the metabolic reactions of the cell and allow vital substances to leak out of the cell, finally causing death.

Classification of the "generation" of quaternary ammonium compounds may be confusing. The most current definitions of the different generations of quaternary ammonium compounds are as follows:

First Generation: Benzalkonium chlorides (example: Benzalkonium chloride). First generation quaternary ammonium compounds have the lowest relative biocidal activity and are commonly used as preservatives.

Second Generation: Substituted benzalkonium chlorides (example: alkyl dimethyl benzyl ammonium chloride). The substitution of the aromatic ring hydrogens with chlorine, methyl and/or ethyl groups resulted in second generation quaternary ammonium compounds with high biocidal activity.

Third Generation: "Dual Quaternary ammonium compounds" (example: contain an equal mixture of alkyl dimethyl benzyl ammonium chloride+alkyl dimethyl ethylbenzyl ammonium chloride). This mixture of two specific quaternary ammonium compounds resulted in a dual quaternary ammonium compound offering increased biocidal activity, stronger detergency, and increased safety to the user (relative lower toxicity).

Fourth Generation: "Twin or Dual Chain Quaternary ammonium compounds"—dialkylmethyl amines (example: didecyl dimethyl ammonium chloride or dioctyl dimethyl ammonium chloride). Fourth generation quaternary ammonium compounds are superior in germicidal performance, lower foaming, and have an increased tolerance to protein loads and hard water.

Fifth Generation: Mixtures of fourth generation quaternary ammonium compounds with second-generation quaternary ammonium compounds (example: didecyl dimethyl ammonium chloride+alkyl dimethyl benzyl ammonium chloride). Fifth generation quaternary ammonium compounds have an outstanding germicidal performance, they are active under more hostile conditions and are safer to use.

This information is general in principle. For example, it may not always be the case that a disinfectant with a fifth-generation quaternary ammonium compound is better than one with a third-generation quaternary ammonium compound. The non-germicide components of a disinfectant also have an impact on overall performance. Quaternary ammonium compounds are extremely sensitive to hard water, and usually require a chelant in the formula to obtain efficacy in these conditions. Although regarded as standard by one authority, the quaternary ammonium compound generation definitions given above may differ from those found elsewhere. Regardless, the examples given should give one a relative understanding of the evolution of quaternary germicides.

Glutaraldehyde-protein interactions indicate an effect of the dialdehyde on the surface of bacterial cells. Many of the studies indicate a powerful binding of the aldehyde to the outer cell layers. Because of this reaction in the outer structures of the cell, there is an inhibitory effect on RNA, DNA, and protein synthesis as a result.

In reacting with bacterial spores, studies have shown that acid glutaraldehyde could interact at the spores' surface and remain there, whereas alkaline glutaraldehyde could penetrate the spore. Thus, the role of the activator: an alkalinizing agent in facilitating penetration and interaction of glutaraldehyde with components of the spore cortex or core. Inhibition of germination, spore swelling, mycelial growth, and sporulation in fungal species at varying concentrations has been demonstrated. The principal structural wall component of many molds and yeast is chitin, which resembles the peptidoglycan of bacteria and is thus a potentially reactive site for glutaraldehyde action. In viruses, the main targets for glutaraldehyde are nucleic acid, proteins, and envelope constituents. The established reactivity of glutaraldehyde with proteins suggests that the viral capsid or viral-specific enzymes are vulnerable to glutaraldehyde treatment.

Ortho-phthalaldehyde is a claimed alternative aldehyde that is currently under investigation. Unlike glutaraldehyde, ortho-phthalaldehyde is odorless, stable, and effective over a wide pH range. It has been proposed that, because of the lack of alpha-hydrogens, ortho-phthalaldehyde remains in its active form at alkaline pH.

EDTA and other chelating agents are often added to the germicide formula to aid in activity in hard water conditions. These ingredients also add to the antimicrobial activity by chelating magnesium and calcium in the organism. EDTA has been shown to boost the effect of antimicrobial activity against gram-negative organisms such as *Pseudomonas aeruginosa*.

Many antimicrobials function by attacking and disrupting the cell membrane causing the microbe to "bleed" to death. Other antimicrobials function by penetrating the cell membrane and subsequently inhibiting one or more functions within the cell. Therefore microbial adaptations, such as reduced outer membrane impermeability and active efflux from the cell, may reduce the effectiveness of many known and commonly used antimicrobials. Antimicrobial resistance has increased due to the over use and misuse of antimicrobials. Part of the problem has been attributed to antimicrobials which, due to their design, leach into the environment excessively overexposing microbes in the environment promoting antimicrobial resistance.

New antimicrobials are required to combat the new antimicrobial resistant microbes. New antimicrobials may be effective verses microbes which are currently resistant to currently known antimicrobials. New antimicrobials may resist leaching off into the environment beyond a predetermined amount to inhibit polluting the environment unnecessarily.

SUMMARY

For the reasons stated above new antimicrobials are required to combat the new antimicrobial resistant microbes. Antimicrobial compositions are described. More particularly, systems and methods for the customizable formation of antimicrobial compositions for coating surfaces are described. Further, systems and methods for the preparation of films and coatings using the prepared antimicrobial compositions are described.

In some embodiments, a protective coating composition may include a compound. A compound may include a bridged polycyclic compound. A bridged polycyclic compound may be a cavitand. Portions of the bridged polycyclic compound may include two or more quaternary ammonium moieties. The coating composition may be antimicrobial.

In some embodiments, a protective coating composition may be antimicrobial.

In some embodiments, a protective coating composition may be self-cleaning.

In some embodiments, a chemical composition may include a chemical compound, wherein the chemical compound has a general structure (I):

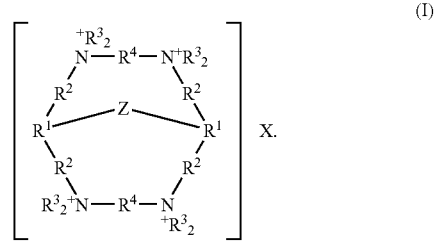

Each $R^1$ may be independently an alkyl group, a substituted alkyl group, an aryl group, a substituted aryl group, N, $N^+R^3$, a heterocycle group, or a substituted heterocycle group. Each $R^2$ may be independently an alkyl group, a substituted alkyl group, an aryl group, a substituted aryl group, a heterocycle group, a substituted heterocycle group, a covalent bond, or an alkene. Each $R^3$ may be independently an alkyl group, a substituted alkyl group, an aryl group, a substituted aryl group, a heterocycle group, a substituted heterocycle group, an alkene, an ether, a PEG, or a PEI. Each $R^4$ may be independently an alkyl group, a substituted alkyl group, an aryl group, a substituted aryl group, a heterocycle group, a substituted heterocycle group, an ether, an amide, an alcohol, an ester, a sulfonamide, a sulfanilamide, or an alkene. Z may include at least one bridge. At least one of the bridges may be $-R^2-N^+R^3{}_2-R^4-N^+R^3{}_2-R^2-$, $-R^2-NR^3-R^4-N^+R^3{}_2-R^2-$, $-R^2-NR^3-R^4-NR^3-R^2-$, or $-R^2-N=R^4=N-R^2-$. Each bridge may independently couples $R^1$ to $R^1$. X may include one or more negatively charged counter ions.

In some embodiments, a chemical composition may include one or more polymerizable compounds.

In some embodiments, a chemical composition may include one or more polymerizable compounds, wherein the chemical composition is configured such that, when the chemical composition is applied to a surface and cured, then at least a portion of the composition forms an antimicrobial coating over at least a portion of the surface.

In some embodiments, at least one $R^3$ may include at least one quaternary ammonium moiety.

In some embodiments, at least one $R^3$ may include at least one phenol moiety.

In some embodiments, at least one $R^3$ may include at least one azole moiety.

In some embodiments, at least one $R^3$ is a benzyl group.

In some embodiments, at least one $R^3$ is a chloro substituted benzyl group.

In some embodiments, at least one $R^3$ is a benzyl group, and wherein at least one $R^3$ is a C6 alkyl group or a C6 substituted alkyl group.

In some embodiments, at least one $R^3$ is a chloro substituted benzyl group, and wherein at least one $R^3$ is a C6 alkyl group or a C6 substituted alkyl group.

In some embodiments, at least one $R^3$ is a methoxy substituted benzyl group, and wherein at least one $R^3$ is a C6 alkyl group or a C6 substituted alkyl group.

In some embodiments, at least one $R^3$ is a alkoxy substituted benzyl group, and wherein at least one $R^3$ is a C6 alkyl group or a C6 substituted alkyl group.

In some embodiments, at least one $R^3$ is a hydroxyl substituted benzyl group, and wherein at least one $R^3$ is a C6 alkyl group or a C6 substituted alkyl group.

In some embodiments, at least one $R^3$ is an ammonium substituted benzyl group, and wherein at least one $R^3$ is a C6 alkyl group or a C6 substituted alkyl group.

In some embodiments, at least one $R^3$ is a polyether substituted benzyl group, and wherein at least one $R^3$ is a C6 alkyl group or a C6 substituted alkyl group.

In some embodiments, at least one $R^3$ is a benzyl group, and wherein at least one $R^3$ is a C6 alkyl group or a C6 substituted imidazole group.

In some embodiments, at least one $R^3$ is a methyl group, and wherein at least one $R^3$ is a C6 alkyl group or a C6 substituted alkyl group.

In some embodiments, at least one $R^3$ is a methyl group, and wherein at least one $R^3$ is a C5-C7 alkyl group or a C5-C7 substituted alkyl group.

In some embodiments, at least one X is an anion. In some embodiments, at least one X is a polymer. In some embodiments, at least one X is a monomer. In some embodiments, at least one X is a halogen. In some embodiments, at least one X is iodine, bromine, or chlorine. In some embodiments, at least one X contains boron. In some embodiments, at least one X is a borate. In some embodiments, at least one X tetrafluoroborate. In some embodiments, at least one X contains nitrogen. In some embodiments, at least one X is a nitrate. In some embodiments, at least one X is $PY_6$, wherein Y is a halogen. In some embodiments, at least one X is hexafluorophosphate. In some embodiments, at least one X is $NTf_2$, and wherein Tf is bis(trifluoromethanesulfonyl)imide.

In some embodiments, Z is one bridge such that the chemical compound has a general structure (II):

$$\begin{bmatrix} \text{(structure II)} \end{bmatrix} X. \quad (II)$$

In some embodiments, Z is two bridges such that the chemical compound has a general structure (III):

$$\begin{bmatrix} \text{(structure III)} \end{bmatrix} X. \quad (III)$$

In some embodiments, Z is one bridge such that the chemical compound has a general structure (IV):

$$\begin{bmatrix} \text{(structure IV)} \end{bmatrix} X. \quad (IV)$$

At least one $R^3$ may be a methyl group. At least one $R^3$ may be a C5-C7 alkyl group or a C5-C7 substituted alkyl group. At least one R4 may be an aryl group or a substituted aryl group.

In some embodiments, Z is one bridge such that the chemical compound has a general structure (IVa):

$$\begin{bmatrix} \text{(structure IVa)} \end{bmatrix} X. \quad (IVa)$$

At least one $R^3$ may be a methyl group. At least one $R^3$ may be a C5-C7 alkyl group or a C5-C7 substituted alkyl group. At least one R4 may be an aryl group or a substituted aryl group. M may include one or more guest molecules associated with one or more portions of compound (IVa).

In some embodiments, a method of making a compound may include coupling an at least bifunctional compound with an at least trifunctional compound in an alcohol based solvent to form a polycyclic imine compound including at least two cyclic groups, wherein at least one of the bifunctional compound and the at least trifunctional compound comprise two or more aldehyde or aldehyde forming moieties, and wherein at least one of the bifunctional compound and the at least trifunctional compound comprise two or more amine or amine forming moieties. The method may further include reducing at least one of the imine moieties of the bridged polycyclic imine compound in an alcohol based solvent with a reducing agent to form a bridged polycyclic compound comprising at least two cyclic groups having a general structure (V):

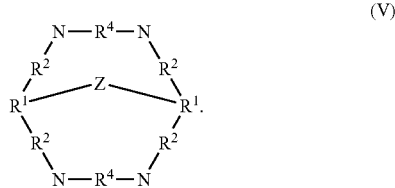

(V)

Each $R^1$ may be independently an alkyl group, a substituted alkyl group, an aryl group, a substituted aryl group, N, a heterocycle group, or a substituted heterocycle group. Each $R^2$ may be independently an alkyl group, a substituted alkyl group, an aryl group, a substituted aryl group, a heterocycle group, a substituted heterocycle group, a covalent bond, or an alkene. Each $R^4$ may be independently an alkyl group, a substituted alkyl group, an aryl group, a substituted aryl group, a heterocycle group, a substituted heterocycle group, an ether, an amide, an alcohol, an ester, a sulfonamide, a sulfanilamide, or an alkene. Z may include at least one bridge. At least one of the bridges may be $—R^2—N=R^4=N—R^2—$ or $—R^2—N=R^4=N—R^2—$. Each bridge may independently couple $R^1$ to $R^1$.

In some embodiments, a method may include formation of the polycyclic imine compound followed by reduction of at least one of the imine moieties of the polycyclic imine compound.

In some embodiments, a method may include formation of the polycyclic imine compound directly followed by reduction of at least one of the imine moieties of the polycyclic imine compound.

In some embodiments, a method may include reducing at least one of the imine moieties of the bridged polycyclic imine compound in tetrahydrofuran solvent with a reducing agent comprises using sodium borohydride as a reducing agent.

In some embodiments, a method may include reducing at least one of the imine moieties of the polycyclic imine compound in an alcohol based solvent with a reducing agent comprises using sodium borohydride as a reducing agent.

In some embodiments, a method may include reducing at least one of the imine moieties of the bridged polycyclic imine compound in an alcohol based solvent with a reducing agent comprises using sodium and ammonia as a reducing agent.

In some embodiments, a method may include alkylating at least four of the amines the chemical compound has a general structure (I):

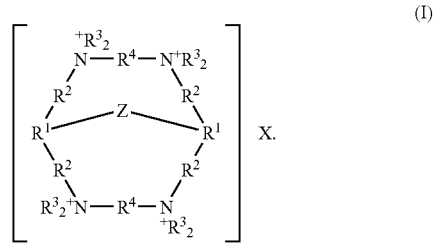

(I)

Each $R^1$ may be independently an alkyl group, a substituted alkyl group, an aryl group, a substituted aryl group, N, $N^+R^3$, a heterocycle group, or a substituted heterocycle group. Each $R^2$ may be independently an alkyl group, a substituted alkyl group, an aryl group, a substituted aryl group, a heterocycle group, a substituted heterocycle group, a covalent bond, or an alkene. Each $R^3$ may be independently an alkyl group, a substituted alkyl group, an aryl group, a substituted aryl group, a heterocycle group, a substituted heterocycle group, an alkene, an ether, a PEG, or a PEI. Each $R^4$ may be independently an alkyl group, a substituted alkyl group, an aryl group, a substituted aryl group, a heterocycle group, a substituted heterocycle group, an ether, an amide, an alcohol, an ester, a sulfonamide, a sulfanilamide, or an alkene. Z comprises at least one bridge, wherein at least one of the bridges may be $—R^2—N^+R^3{}_2—R^4—N^+R^3{}_2—R^2—$, $—R^2—NR^3—R^4—N^+R^3{}_2—R^2—$, $—R^2—NR^3—R^4—NR^3—R^2—$, or $—R^2—N=R^4=N—R^2—$. Each bridge independently couples $R^1$ to $R^1$. X may include one or more negatively charged counter ions.

In some embodiments, a method of coating a surface may include applying a composition to a surface. The composition may include one or more bridged polycyclic compounds. At least one of the bridged polycyclic compounds may include at least two cyclic groups. At least two cyclic groups may be defined in part by quaternary ammonium moieties. The method may include forming an antimicrobial coating over at least a portion of the surface.

In some embodiments, at least one of the bridge polycyclic compounds may include at least four quaternary ammonium moieties which define at least two of the cyclic groups forming the bridged polycyclic compounds.

In some embodiments, at least one of the bridge polycyclic compounds may include at least two phenol moieties which define at least two of the cyclic groups forming the bridged polycyclic compounds.

In some embodiments, at least one of the quaternary ammonium moieties defining at least one of the cyclic groups further comprises an alkyl group, a substituted alkyl group, an aryl group, a heterocycle group, a substituted heterocycle group, or a substituted aryl group.

In some embodiments, at least one of the quaternary ammonium moieties defining at least one of the cyclic groups further comprises an alkyl group, a substituted alkyl group, an aryl group, or a substituted aryl group and an alkyl group, a substituted alkyl group, an aryl group, or a substituted aryl group.

In some embodiments, at least one of the quaternary ammonium moieties defining at least one of the cyclic groups further comprises a C6 alkyl group or a C6 substituted alkyl group and a methyl group or a benzyl group.

In some embodiments, the bridge polycyclic compound has a general structure (I):

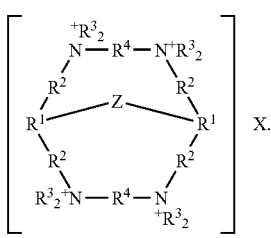

In some embodiments, a method of coating a surface may include curing the composition such that at least a portion of the composition bonds to the surface.

In some embodiments, the composition may include a polymerizable compound. The polymerizable compound may include polymerizable amides, esters, olefins, acrylates, methacrylates, urethanes, vinyl esters, epoxy-based materials, styrene, styrene acrylonitrile, sulfones, acetals, carbonates, phenylene ethers, ureas, or phenylene sulfides. The polymerizable compound may include 2,2'-bis[4-(3-methacryloxy-2-hydroxy propoxy)-phenyl]-propane, dipentaerythritol pentaacrylate, pentaerythritol dimethacrylate, the condensation product of ethoxylated bisphenol A and glycidyl methacrylate, the condensation product of 2 parts hydroxymethylmethacrylate and 1 part triethylene glycol bis (chloroformate), or polyurethane dimethacrylates. The polymerizable compound may include hydroxyalkl methacrylates, 2-hydroxyethyl methacrylate, 1,6-hexanediol dimethacrylate, 2-hydroxypropyl methacrylate, glyceryl dimethacrylate, ethyleneglycolmethacrylates, ethylenegly-col methacrylate, diethyleneglycol methacrylate, or triethyleneglycol methacrylate. The polymerizable compound may include methacrylic acid, maleic acid p-vinylbenzoic acid, 11-methacryloyloxy-1,1-undecanedicarboxylic acid, 1,4-dimethacryloyloxyethylpyromellitic acid, 6methacryloyloxyethylnaphthalene-1,2,6-tricarboxylic acid, 4-methacryloyloxymethyltrimellitic acid and the anhydride thereof, 4-methacryloyloxyethyltrimellitic acid and an anhydride thereof, 4-(2-hydroxy-3-methacryloyloxy)bultytrimellitic acid and an anhydride thereof, 2,3-bis(3,4-dicarboxybenzoyloxy)propyl methacrylate, methacryloyloxytyrosine, N-methacryloyloxytyrosine, N-methacryloyloxyphenylalanine, methacryloyl-p-aminobenzoic acid, the adduct of 2-hydroxyethyl methacrylate with pyromellitic dianhydride, the adduct of 2-hydroxyethyl methacrylate with maleic anhydride, the adduct of 2-hydroxyethyl methacrylate with 3,3',4,4'-benzophenonetetracarboxylic dianhydride, the adduct of 2-hydroxyethyl methacrylale with 3,3',4,4'-biphenyltetracarboxylic dianhydride, the adduct of an aromatic dianhydride with an excess of 2-HEMA, the adduct of 2-HEMA with ethylene glycol bistrimellitate dianhydride, the adduct of 3,3', 4,4'-diphenylsulfone tetracarboxylic dianhydide and 2-HEMA, the adduct of pyromellitic dianhydride with glycerol dimethacrylate, 2-methacryloyloxyethyl acidophosphate, 2-methacryloyloxypropyl acidophosphate, 4-methacryloyloxybutyl acidophosphate, 8-methacryloyloxyoctyl acidophosphate, 10-methacryloyloxydecyl acidophosphate, bis(2-methacryloyloxyethyl)acidophosphate, 2-methacryloyloxyethylphenyl acidophosphate, 2-sulfoethyl methacrylate, 3-sulfo-2-butyl methaclylate, 3-bromro-2-sulfo-2-propyl methacrylate, 3-methoxy-1-sulfo-2-propyl mathacrylate, or 1,1-dimethyl-2-sulfoethyl methacrylamide.

In some embodiments, the composition may include an initiator. The initiator may include benzil diketones, DL-camphorquinone, peroxides, lauryl peroxide, tributyl hydroperoxide, cumene hydroperoxide, 1,1'-azobis(cyclohexanecarbonitrile), or benzoyl peroxide.

In some embodiments, the composition may include an accelerator comprising tertiary amines, dimethylaminoethyl methacrylate, diethylaminoethyl methacrylate, aromatic tertiary amines, 4-(N,N-dimethyl)aminobenzoate, dimethyl-p-toluidine, and dihydroxyethyl-p-toluidine.

In some embodiments, the composition may include one or more of ultra-violet light absorbers, anti-oxidants, stabilizers, fillers, pigments, opacifiers, gelators, or handling agents.

In some embodiments, the composition may include a filler comprising amorphous silica, spherical silica, colloidal silica, barium glasses, quartz, ceramic fillers, silicate glass, hydroxyapatite, calcium carbonate, fluoroaluminosilicate, barium sulfate, quartz, barium silicate, strontium silicate, barium borosilicate, barium boroaluminosilicate, strontium borosilicate, strontium boroaluminosilicate, glass fibers, lithium silicate, ammoniated calcium phosphate, deammoniated calcium phosphate, alumina, zirconia, tin oxide, polymer powders, polymethyl methacrylate, polystyrene, or polyvinyl chloride, titania.

In some embodiments, the composition may include a solvent.

In some embodiments, the composition may include a chelating agent. The chelating agent may include EDTA.

In some embodiments, the composition may include a boric acid compound.

In some embodiments, at least one X comprises tetrafluoroborate.

In some embodiments, the composition may include sodium tetrafluoroborate.

In some embodiments, a compound may include a shape with a substantially curved surface.

In some embodiments, a coating may be self-cleaning. In some embodiments, a coating may inhibit microbial adhesion.

In some embodiments, a compound may have a minimum inhibitory concentration of less than 0.1 mg/mL.

In some embodiments, a composition may have a minimum inhibitory concentration of less than 0.05 mg/mL.

In some embodiments, at least one $R^1$ is $N^+R^3$. In some embodiments, at least one $R^1$ is

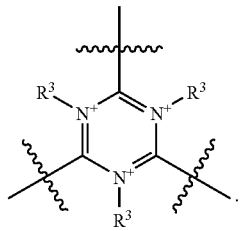

In some embodiments, at least one $R^3$ is hydrophilic. In some embodiments, at least one $R^3$ is a polymer. In some embodiments, at least one $R^3$ is an oxazoline polymer. In some embodiments, at least one $R^3$ is hydrophobic.

In some embodiments, at least one R⁴ may be

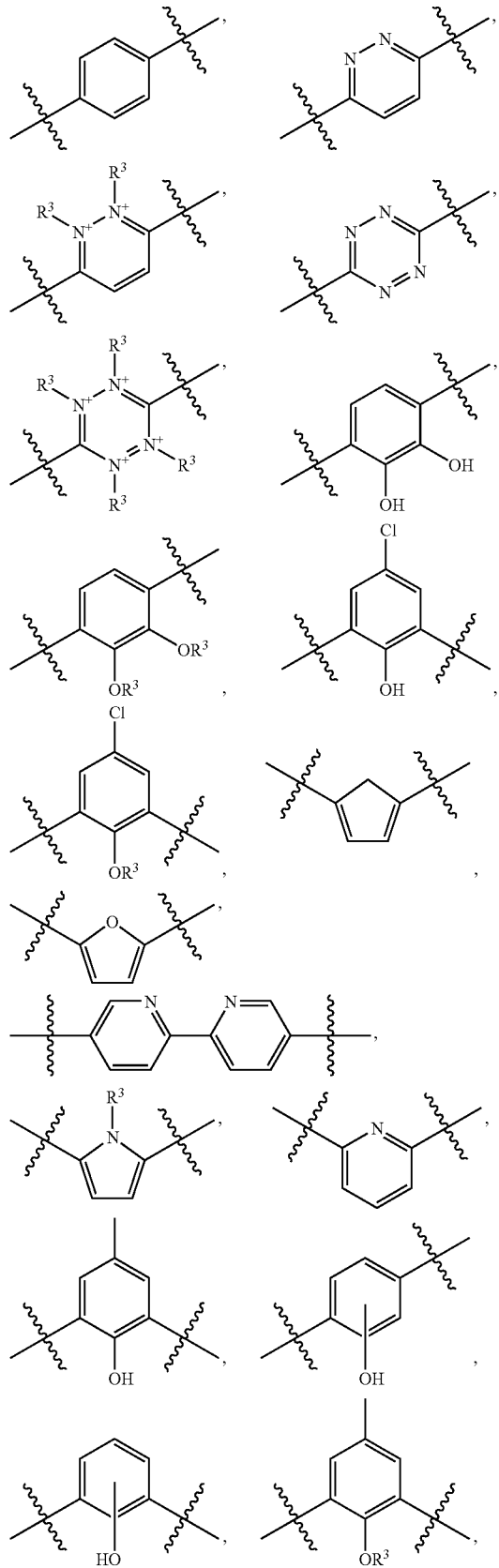

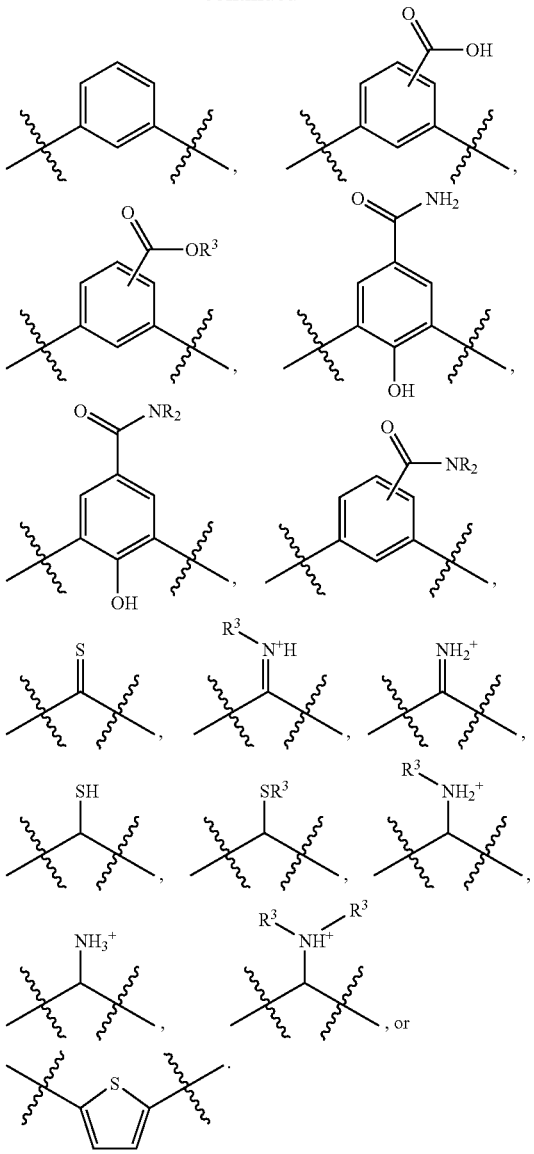

In some embodiments, a composition may include at least one metal (M) coordinated to at least a portion of the compound. At least one M may include a cation. At least one M may be positioned inside a space defined by $R^2$ and $R^4$, and wherein at least one M is coordinated to one or more $N^+R^3{}_2$'s.

In some embodiments, at least one X may include a halogen ion.

In some embodiments, at least one X may include one or more elements with antimicrobial activity.

In some embodiments, at least one X may include one or more elements with antiinflammatory activity In some embodiments, at least one X may include boron.

In some embodiments, a composition may include one or more metals and/or metal ions with antimicrobial properties.

In some embodiments, a composition may include one or more metals and/or metal ions with antiinflammatory properties.

In some embodiments, a composition may include one or more metals and/or metal ions, and wherein one or more of the metals are light activated such that activating the metal with light increases the antimicrobial activity of the metal.

In some embodiments, a composition may include one or more metals and/or metal ions, and wherein at least one metals and/or metal ions is silver. At least one metals and/or metal ions may be zinc, copper, gold, or cesium. At least one metals and/or metal ions may be silver, zinc, copper, gold, calcium, nickel, cobalt, barium, strontium, lead, lanthanum, iron, manganese, cadmium, magnesium, Y, La, Ce, Pr, Nd, Eu, Gd, Tb, Dy, Ho, Er, Tm, Yb, Ce, or alkaline earth metals.

In some embodiments, a method of coating a surface may include pretreating the surface such that the treated surface reacts with the composition. In some embodiments, a method of coating a surface may include pretreating the surface such that the treated surface reacts with the composition by coupling an amide precursor electrophile to the surface. In some embodiments, a method of coating a surface may include pretreating the surface such that the treated surface reacts with the composition by coupling maleic anhydride and/or a maleic anhydride derivative to the surface.

In some embodiments, a composition may include a metal oxide coated bridged polycyclic compound. The metal oxide may include titanium oxide. The metal oxide may include zirconium oxide. The metal oxide may include hafniium oxide. The metal oxide may include boron. The metal oxide may include zinc. The metal oxide may include tantalum. The metal oxide may include titanium oxide, zirconium oxide, hafiium oxide, tungsten oxide, boron, zinc, vanadium, silicon, calcium, bismuth, V, Si, $CaBi_2O_4$, barium, or tantalum In some embodiments, a composition may include stabilizers. The stabilizers may function to increase the solubility of the compound. The stabilizers may function to increase the solubility of the compound in hydrophobic solvents.

In some embodiments, a composition may include metal oxide coated bridged polycyclic compound, and the composition may function to increase the solubility of the compound in hydrophilic solvents.

In some embodiments, a metal oxide coated bridged polycyclic compound is light activated. In some embodiments, a metal oxide coated bridged polycyclic compound is light activated such that activating the metal oxide coated bridged polycyclic compound with light increases the antimicrobial activity of the metal oxide coated bridged polycyclic compound. In some embodiments, a metal oxide coated bridged polycyclic compound is ultraviolet light activated such that activating the metal oxide coated bridged polycyclic compound with light increases the antimicrobial activity of the metal oxide coated bridged polycyclic compound.

In some embodiments, a composition may include a matrix.

In some embodiments, a composition may include thermoplastic polymers.

In some embodiments, a composition may include thermosetting polymers.

In some embodiments, a composition may include engineering plastics.

In some embodiments, a composition may include liquid crystal polymers.

In some embodiments, a composition may include aminoacrylic resins.

In some embodiments, a composition may include epoxy resins.

In some embodiments, a composition may include polyurethane resins.

In some embodiments, a composition may include a cross-linking reagent.

In some embodiments, a composition may include a polymerization catalyst.

In some embodiments, a composition may include a stabilizer.

In some embodiments, a composition may include a delustering agent.

In some embodiments, a composition may include an optical whitening agent.

In some embodiments, a composition may include an organic pigment.

In some embodiments, a composition may include an inorganic pigment.

In some embodiments, a composition may include an inorganic filler.

In some embodiments, a composition may include a plasticizer.

In some embodiments, a composition may include a surfactant.

In some embodiments, a composition may include polyvinyl alcohol.

In some embodiments, a composition may include polymethyl methacrylate.

In some embodiments, a composition may include polymethyl-co-polybutyl methacrylate.

In some embodiments, a composition comprises a coalescing solvent.

In some embodiments, a coated surface, may include a chemical composition. At least a portion of the chemical composition may form an antimicrobial coating over at least a portion of a surface. The chemical composition may include one or more bridged polycyclic compounds. At least one of the bridged polycyclic compounds may include at least two cyclic groups. At least two cyclic groups may be defined in part by quaternary ammonium moieties.

In some embodiments, a compound and/or a coating composition may have a minimum inhibitory concentration of greater than 900 µM (e.g., 900 µM-1500 µM, 900 µM-2000 µM, 1500 µM-2500 µM, etc.). In some embodiments, a compound and/or a coating composition may have a minimum inhibitory concentration of less than 10.0 mg/mL less than 5.0 mg/mL, less than 1.0 mg/mL, less than 0.1 mg/mL, or less than 0.05 mg/mL. In such compositions, antimicrobial properties may not be the primary function of a coating composition. For example, self-cleaning properties may be the primary focus of the coating composition.

In some embodiments, at least some of the herein described compounds includes a metal oxide coating or shell. The metal oxide may include titanium oxide, zirconium oxide, hafiium oxide, boron, zinc, vanadium, silicon, calcium, bismuth, barium or tantalum. Metal oxide shells may include metals which are light activated such that activation with light increases the antimicrobial activity of the compound and metal oxide in particular. In some embodiments, a metal oxide shell may include stabilizers. Stabilizers may function to increase the solubility of a compound in hydrophobic and/or hydrophilic solvents.

In some embodiments, a method of coating a building substrate, may include applying a composition to a surface of a building substrate. The composition may include one or more bridged polycyclic compounds. At least one of the bridged polycyclic compounds may include at least two cyclic groups. At least two cyclic groups may be defined in part by quaternary ammonium moieties. The method may include forming an antimicrobial coating over at least a portion of the surface.

The building substrate may include at least a portion of an interior and/or exterior wall, one or more structural supports of a building, or at least a portion of a roof and/or ceiling.

The method may include using the composition as a primer for the surface.

The method may include using the composition as a sealant for the surface.

The composition may include a pigment and the method further including using the composition as a paint for the surface.

The composition may include a chelating agent. The chelating agent may include EDTA.

The composition may include a boric acid compound.

At least one X of the compound may include tetrafluoroborate.

In some embodiments, a coating composition may include sodium tetrafluoroborate.

In some embodiments, a coating composition may include potassium tetrafluoroborate.

In some embodiments, a building substrate may be coated with a coating The coating may include a chemical composition at least a portion of which forms an antimicrobial coating over at least a portion of a surface of the building substrate. The chemical composition may include one or more bridged polycyclic compounds. At least one of the bridged polycyclic compounds may include at least two cyclic groups. At least two cyclic groups may be defined in part by quaternary ammonium moieties.

In some embodiments, a method of coating a marine substrate, may include applying a composition to a surface of a marine substrate. The composition may include one or more bridged polycyclic compounds. At least one of the bridged polycyclic compounds may include at least two cyclic groups. At least two cyclic groups may be defined in part by quaternary ammonium moieties. The method may include forming an antimicrobial coating over at least a portion of the surface.

The method may include inhibiting the growth of bacteria on the surface.

The marine substrate may include at least a portion of a boat, at least a portion of an outer hull of a boat, at least a portion of a pier, at least a portion of a boat dock, at least a portion of an outer hull of a submersible vessel, at least a portion of a surf board, or at least a portion of a offshore oil and/or gas rig.

In some embodiments, a marine substrate may be coated with a coating The coating may include a chemical composition at least a portion of which forms an antimicrobial coating over at least a portion of a surface of the marine substrate. The chemical composition may include one or more bridged polycyclic compounds. At least one of the bridged polycyclic compounds may include at least two cyclic groups. At least two cyclic groups may be defined in part by quaternary ammonium moieties.

In some embodiments, a method of inhibiting growth of mollusks on a marine substrate, may include applying a composition to a surface of a marine substrate. The composition may include one or more bridged polycyclic compounds. At least one of the bridged polycyclic compounds may include at least two cyclic groups. At least two cyclic groups may be defined in part by quaternary ammonium moieties. The method may include forming an antimicrobial coating over at least a portion of the surface. The method may include inhibiting growth of mollusks on the marine substrate to which the composition has been applied.

In some embodiments, a method of coating an oral surface, may include applying a composition to a surface of an oral surface. The composition may include one or more bridged polycyclic compounds. At least one of the bridged polycyclic compounds may include at least two cyclic groups. At least two cyclic groups may be defined in part by quaternary ammonium moieties. The method may include forming an antimicrobial coating over at least a portion of the surface.

The oral surface may include at least a portion of a tooth surface, at least a portion of a gum, at least a portion of soft tissue, or at least a portion of a dental fixture. A dental fixture may include a filling, at least a portion of a bridge, or at least a portion of a denture.

The composition may be in the form of a gel.

In some embodiments, a composition may include a coalescing solvent.

The method may include using the composition as a bonding agent.

The method may include using the composition as a resin cement.

The method may include using the composition as a sealant.

The method may include using the composition as a varnish.

The method may include using the composition as a resin.

In some embodiments, an oral surface may be coated with a coating The coating may include a chemical composition at least a portion of which forms an antimicrobial coating over at least a portion of the oral surface. The chemical composition may include one or more bridged polycyclic compounds. At least one of the bridged polycyclic compounds may include at least two cyclic groups. At least two cyclic groups may be defined in part by quaternary ammonium moieties.

In some embodiments, a method of coating a medical device, may include applying a composition to a surface of a medical device. The composition may include one or more bridged polycyclic compounds. At least one of the bridged polycyclic compounds may include at least two cyclic groups. At least two cyclic groups may be defined in part by quaternary ammonium moieties. The method may include forming an antimicrobial coating over at least a portion of the surface.

In some embodiments, a medical device may include at least a portion of a stent, at least a portion of a catheter, at least a portion of a cannulae, at least a portion of a contact lenses, or at least a portion of a feeding tube.

In some embodiments, a composition may be included as part of an application kit for coating at least a portion of the medical device.

In some embodiments, a medical device may be coated with a coating The coating may include a chemical composition at least a portion of which forms an antimicrobial coating over at least a portion of the medical device. The chemical composition may include one or more bridged polycyclic compounds. At least one of the bridged polycyclic compounds may include at least two cyclic groups. At least two cyclic groups may be defined in part by quaternary ammonium moieties.

In some embodiments, a method of coating a personal care device, may include applying a composition to a surface of a personal care device. The composition may include one or more bridged polycyclic compounds. At least one of the bridged polycyclic compounds may include at least two cyclic groups. At least two cyclic groups may be defined in part by quaternary ammonium moieties. The method may include forming an antimicrobial coating over at least a portion of the surface.

In some embodiments, a composition may be included as part of an application kit for coating at least a portion of the personal care device.

In some embodiments, a personal care device may include a foot bath, a pedicure bath system, or one or more pedicure instruments.

In some embodiments, a personal care device may be coated with a coating The coating may include a chemical composition at least a portion of which forms an antimicrobial coating over at least a portion of the personal care device. The chemical composition may include one or more bridged polycyclic compounds. At least one of the bridged polycyclic compounds may include at least two cyclic groups. At least two cyclic groups may be defined in part by quaternary ammonium moieties.

BRIEF DESCRIPTION OF THE DRAWINGS

Advantages of the present invention may become apparent to those skilled in the art with the benefit of the following detailed description of the preferred embodiments and upon reference to the accompanying drawings in which.

Figure 1:
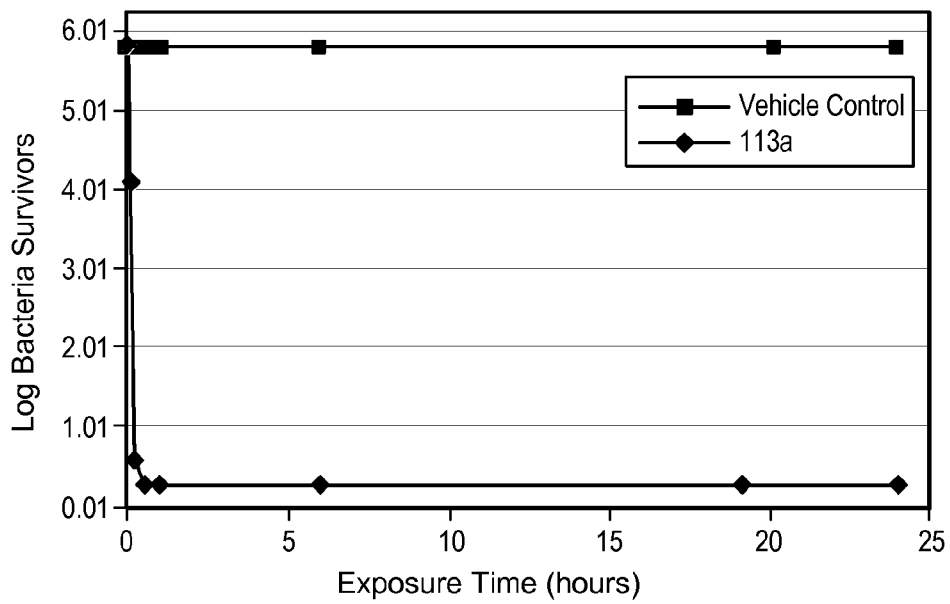
FIG. 1 depicts a graphical representation of time kill assay tests for a bridged polycyclic compound tested against *Staphylococcus aureaus*.
Figure 2:
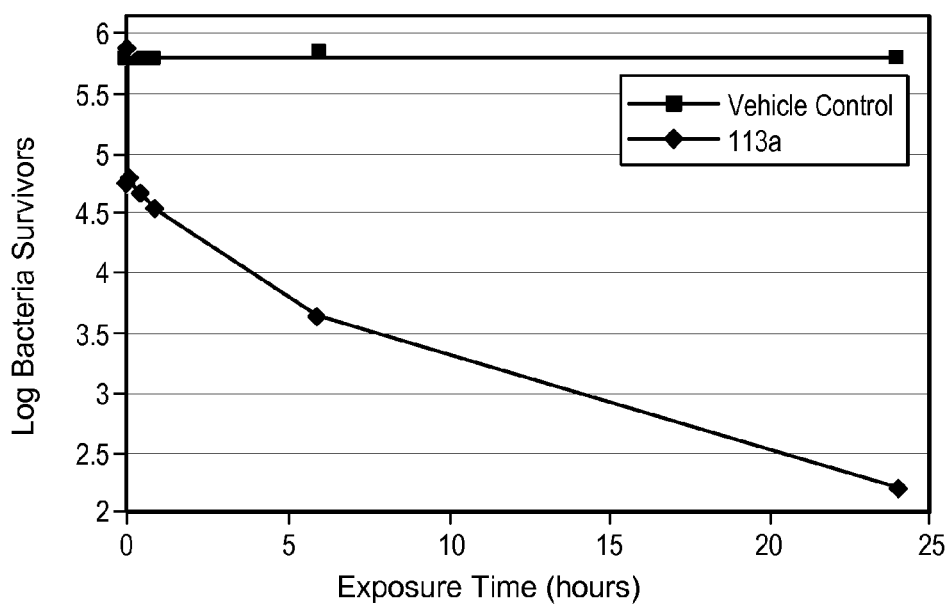
FIG. 2 depicts a graphical representation of time kill assay tests for a bridged polycyclic compound tested against *Escherichia coli*.
Figure 3:
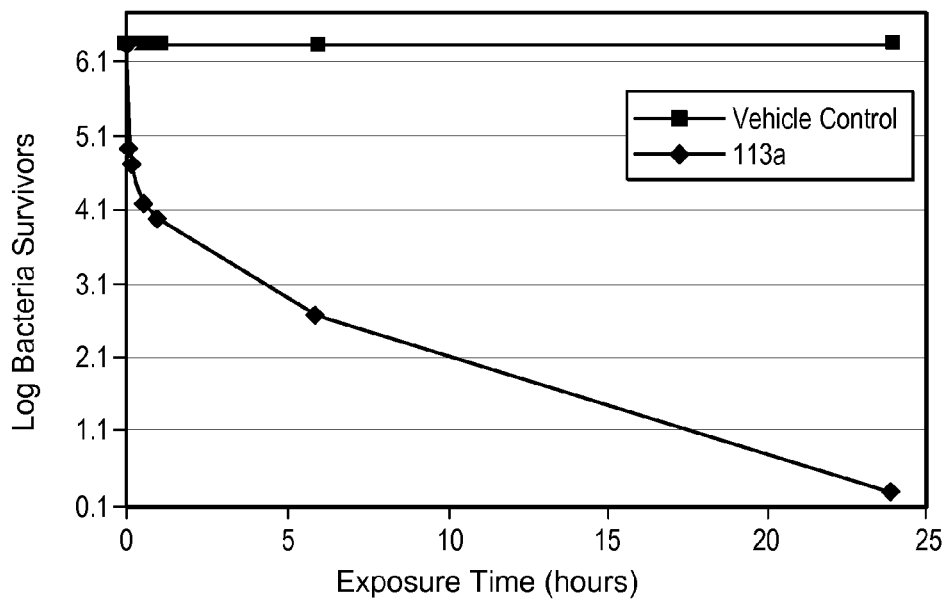
FIG. 3 depicts a graphical representation of time kill assay tests for a bridged polycyclic compound tested against *Escherichia coli*.
Figure 4:
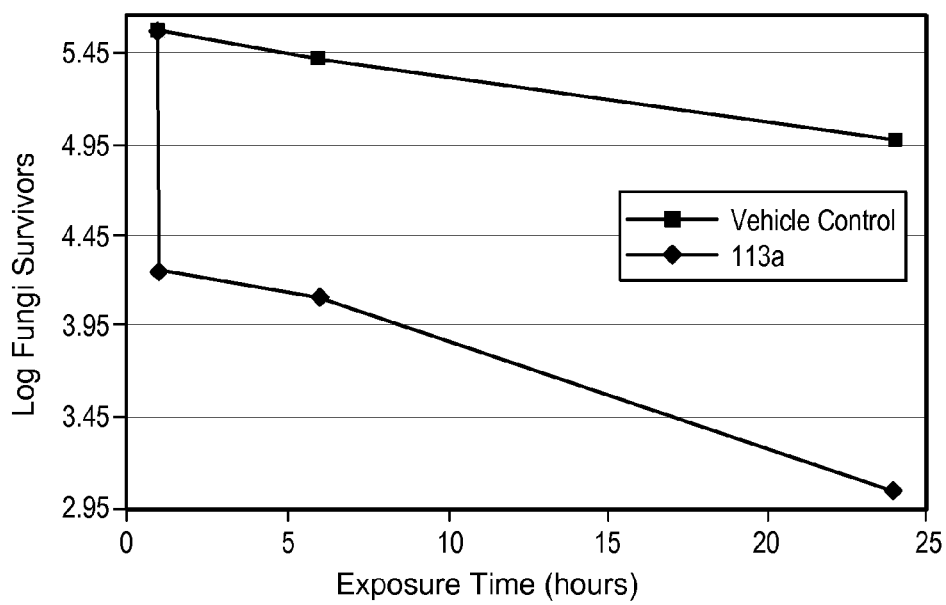
FIG. 4 depicts a graphical representation of time kill assay tests for a bridged polycyclic compound tested against *Aspergillus niger*.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DEFINITIONS

Unless defined otherwise, all technical and scientific terms used herein have the same meaning as commonly understood by one of ordinary skill in the art.

The term "accelerator" as used herein generally refers to a substance that speeds a chemical reaction.

The term "acyl" as used herein generally refers to a carbonyl substituent, —C(O)R, where R is alkyl or substituted alkyl, aryl, or substituted aryl, which may be called an alkimoyl substituent when R is alkyl.

The term "adhesive" as used herein generally refers to a substance (e.g., glue, starch, paste, or mucilage) that bonds two materials together by adhering to the surface of each.

The term "aldehyde" as used herein generally refers to any of a class of organic compounds containing the group —CHO (i.e., 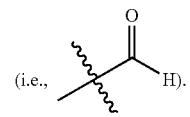 ).

The term "aldehyde forming moiety" as used herein generally refers to any of a class of organic compounds which form an aldehyde in solution or react in an equivalent manner to an aldehyde such that an at least similar chemical product is acieved as would have been achieved with an aldehyde.

The terms "alkenyl" and "alkene" as used herein generally refer to any structure or moiety having the unsaturation C═C. As used herein, the term "alkynyl" generally refers to any structure or moiety having the unsaturation C≡C.

The term "alkoxy" generally refers to an —OR group, where R is an alkyl, substituted lower alkyl, aryl, substituted aryl. Alkoxy groups include, for example, methoxy, ethoxy, phenoxy, substituted phenoxy, benzyloxy, phenethyloxy, t-butoxy, and others.

The term "alkyl" as used herein generally refers to a chemical substituent containing the monovalent group $C_nH_{2n}$, where n is an integer greater than zero. Alkyl includes a branched or unbranched monovalent hydrocarbon radical. An "n-mC" alkyl or "(nC-mC)alkyl" refers to all alkyl groups containing from n to m carbon atoms. For example, a 1 -4C alkyl refers to a methyl, ethyl, propyl, or butyl group. All possible isomers of an indicated alkyl are also included. Thus, propyl includes isopropyl, butyl includes n-butyl, isobutyl and t-butyl, and so on. The term alkyl may include substituted alkyls.

The term "alkyl-aryl" as used herein generally refers to a chemical substituent containing an alkyl group coupled to an aryl group or a substituted aryl group.

The terms "amino" or "amine" as used herein generally refer to a group —NRR', where R and R' may independently include, but are not limited to, hydrogen, alkyl, substituted alkyl, aryl, substituted aryl or acyl.

The terms "amine forming moiety" as used herein generally refers to any of a class of organic compounds which form an amine in solution or react in an equivalent manner to an anmine such that an at least similar chemical product is achieved as would have been achieved with an amine.

The terms "amphiphile" or "amphiphilic" as used herein generally refer to a molecule or species which exhibits both hydrophilic and lipophilic character. In general, an amphiphile contains a lipophilic moiety and a hydrophilic moiety. The terms "lipophilic" and "hydrophobic" are interchangeable as used herein. An amphiphile may form a Langmuir film.

Non-limiting examples of hydrophobic groups or moieties include lower alkyl groups, alkyl groups having 6, 7, 8, 9, 10, 11, 12, or more carbon atoms, including alkyl groups with 14-30, or 30 or more carbon atoms, substituted alkyl groups, alkenyl groups, alkynyl groups, aryl groups, substituted aryl groups, saturated or unsaturated cyclic hydrocarbons, heteroaryl, heteroarylalkyl, heterocyclic, and corresponding substituted groups. A hydrophobic group may contain some hydrophilic groups or substituents insofar as the hydrophobic character of the group is not outweighed. In further variations, a hydrophobic group may include substituted silicon atoms, and may include fluorine atoms. The hydrophobic moieties may be linear, branched, or cyclic.

Non-limiting examples of hydrophilic groups or moieties include hydroxyl, methoxy, phenyl, carboxylic acids and salts thereof, methyl, ethyl, and vinyl esters of carboxylic acids, amides, amino, cyano, isocyano, nitrile, ammonium salts, sulfonium salts, phosphonium salts, mono- and di-alkyl substituted amino groups, polypropyleneglycols, polyethylene glycols, epoxy groups, acrylates, sulfonamides, nitro, —OP(O)(OCH$_2$CH$_2$N$^+$RRR)O$^-$, guanidinium, aminate, acrylamide, pyridinium, piperidine, and combinations thereof, wherein each R is independently selected from H or alkyl. Further examples include polymethylene chains substituted with alcohol, carboxylate, acrylate, or methacrylate. Hydrophilic moieties may also include alkyl chains having internal amino or substituted amino groups, for example, internal —NH—, —NC(O)R—, or —NC(O)CH=CH$_2$— groups, wherein R is H or alkyl. Hydrophilic moieties may also include polycaprolactones, polycaprolactone diols, poly(acetic acid)s, poly(vinyl acetates)s, poly(2-vinyl pyridine)s, cellulose esters, cellulose hydroxylethers, poly(L-lysine hydrobromide)s, poly(itaconic acid)s, poly(maleic acid)s, poly(styrenesulfonic acid)s, poly(aniline)s, or poly(vinyl phosphonic acid)s. A hydrophilic group may contain some hydrophobic groups or substituents insofar as the hydrophilic character of the group is not outweighed.

The term "aryl" as used herein generally refers to a chemical substituent containing an aromatic group (e.g., phenyl). An aromatic group may be a single aromatic ring or multiple aromatic rings which are fused together, coupled covalently, or coupled to a common group such as a methylene, ethylene, or carbonyl, and includes polynuclear ring structures. An aromatic ring or rings may include, but is not limited to, substituted or unsubstituted phenyl, naphthyl, biphenyl, diphenylmethyl, and benzophenone groups. The term "aryl" includes substituted aryls The term "antiinflammatory" as used herein generally refers to a substance acting to reduce certain signs of inflammation (e.g., swelling, tenderness, fever, and pain).

The term "antimicrobial" as used herein generally refers to a substance capable of destroying or inhibiting the growth of microbes, prevents the development of microbes, and/or inhibits the pathogenic action of microbes as well as viruses, fungi, and bacteria.

The term "bridged polycyclic compound" as used herein generally refers to a compound that is composed of two or more cyclic systems that share two or more atoms. A cyclic system is formed from a group of atoms which together form a continuous loop. A bridged polycyclic compound may include a bridging atom or group of atoms that connects two or more non-adjacent positions of the same ring. An example of a bridged bicyclic system (i.e., a compound composed of two cyclic systems) with two atoms (atoms "A") common to both cyclic systems is depicted below. One of the linking groups "L" represents a bridging atom or group of atoms.

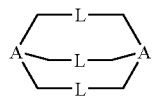

The term "building substrate" as used herein generally refers to a natural or synthetic material used in the construction of a residential or commercial structure.

The term "cavitand" as used herein generally refers to a natural or synthetic molecular compound with enforced cavities large enough to complex complementary compounds or ions. More specifically, a cavitand may be generally defined as a three-dimensional compound that maintains a substantially rigid structure and binds a variety of molecules in the cavities produced by the structure of the three-dimensional compound.

The term "chelating agent or complexing agent" as used herein generally refers to any of various compounds that combine with metals to form chelates.

The term "coalescing agents or solvents" as used herein generally refers to any of various compounds that are used in coatings to promote film formation (e.g., in architectural and industrial latex coating).

The term "coating" as used herein generally includes coatings that completely cover a surface, or portion thereof, as well as coatings that may only partially cover a surface, such as those coatings that after drying leave gaps in coverage on a surface. The later category of coatings may include, but is not limited to a network of covered and uncovered portions (e.g., non-continuous covered regions of the surface). When the coatings described herein are described as being applied to a surface, it is understood that the coatings need not be applied to, or that they cover the entire surface. For instance, the coatings will be considered as being applied to a surface even if they are only applied to modify a portion of the surface. The coating may be applied to a surface or impregnated within the material used to construct an item or a portion of an item.

The terms "coupling" and "coupled" with respect to molecular moieties or species, atoms, synthons, cyclic compounds, and nanoparticles refers to their attachment or association with other molecular moieties or species, atoms, synthons, cyclic compounds, and nanoparticles. The attachment or association may be specific or non-specific, reversible or non-reversible, the result of chemical reaction, or complexation or charge transfer. The bonds formed by a coupling reaction are often covalent bonds, or polar-covalent bonds, or mixed ionic-covalent bonds, and may sometimes be Coulombic forces, ionic or electrostatic forces or interactions.

The terms "crystalline" or "substantially crystalline", when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal typically does not extend beyond the boundaries of the crystal. In this case, "long-range ordering" will mean substantial order across at least the majority of the dimension of the nanostructure. In some instances, a nanostructure may bear an oxide or other coating, or may be comprised of a core and at least one shell. In such instances it will be appreciated that the oxide, shell(s), or other coating need not exhibit such ordering (e.g., it may be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, etc., as long as the structure exhibits substantial long range ordering (e.g., order over at least about 80% of the length of at least one axis of the nanostructure or its core). It may be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein.

The term "cyclic" as used herein generally refers to compounds having wherein at least some of the atoms are arranged in a ring or closed-chain structure.

The term "dental compositions" as used herein generally refers to any substances typically associated with any type of dental work and/or in related fields and includes, but is not limited to, dental primers, adhesives, surface sealants, liners, luting cements, varnishes, impression materials, equipment and impression systems, and composite restoratives.

The term "dental fixture" as used herein generally refers to an at least partially synthetic material configured to positioned in and/or coupled to at least a portion of an oral cavity. For example a dental fixture may include, but is not limited to, a filling, a bridge, a false tooth, a cap, or denture.

The term "effective concentration" or "effective amount" as used herein generally refers to a sufficient amount of the antimicrobial agent is added to decrease, prevent or inhibit the growth of microbial organisms. The amount will vary for each compound and upon known factors related to the item or use to which the antimicrobial agent is applied.

The term "film" as used herein generally refers to a thin sheet of material (e.g., plastic) used to at least partially cover at least a portion of a surface. The material may be transparent, translucent, or opaque. The film may be a solid continuous sheet or the film may contain perforations (e.g., a web like material).

The terms "functionalized" or "functional group" as used herein generally refers to the presence of a reactive chemical moiety or functionality. A functional group may include, but is not limited to, chemical groups, biochemical groups, organic groups, inorganic groups, organometallic groups, aryl groups, heteroaryl groups, cyclic hydrocarbon groups, amino (—NH$_2$), hydroxyl (—OH), cyano (—C≡N), nitro (NO$_2$), carboxyl (—COOH), formyl (—CHO), keto (—CH$_2$C(O)CH$_2$—), ether (—CH$_2$—O—CH$_2$—), thioether (—CH$_2$—S—CH$_2$—), alkenyl (—C=C—), alkynyl, (—C≡C—), epoxy

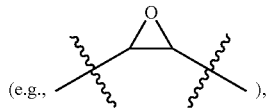

(e.g., ), metalloids (functionality containing Si and/or B) and halo (F, Cl, Br, and I) groups. In some embodiments, the functional group is an organic group.

The term "gram-negative bacteria" or "gram-negative bacterium" as used herein generally refers to bacteria which have been classified by the Gram stain as having a red stain. Gram-negative bacteria have thin walled cell membranes consisting of a single layer of peptidoglycan and an outer layer of lipopolysacchacide, lipoprotein, and phospholipid. Exemplary organisms include, but are not limited to, Enterobacteriacea consisting of *Escherichia, Shigella, Edwardsiella, Salmonella, Citrobacter, Klebsiella, Enterobacter, Hafnia, Serratia, Proteus, Morganella, Providencia, Yersinia, Erwinia, Buttlauxella, Cedecea, Ewingella, Kluyvera, Tatumella* and *Rahnella*. Other exemplary gram-negative organisms not in the family Enterobacteriacea include, but are not limited to, *Pseudomonas aeruginosa, Stenotrophomonas maltophilia, Burkholderia, Cepacia, Gardenerella, Vaginalis,* and *Acinetobacter* species.

The term "gram-positive bacteria" or "gram-positive bacterium" as used herein refers to bacteria, which have been classified using the Gram stain as having a blue stain. Gram-positive bacteria have a thick cell membrane consisting of multiple layers of peptidoglycan and an outside layer of teichoic acid. Exemplary organisms include, but are not limited to, *Staphylococcus aureus*, coagulase-negative *staphylococci, streptococci, enterococci, corynebacteria,* and *Bacillus* species.

The term "heteroaryl" generally refers to a completely unsaturated heterocycle.

The term "heterocycle" as used herein generally refers to a closed-ring structure, in which one or more of the atoms in the ring is an element other than carbon. Heterocycle may include aromatic compounds or non-aromatic compounds. Heterocycles may include rings such as thiophene, pyridine, isoxazole, phthalimide, pyrazole, indole, furan, or benzo-fused analogues of these rings. Examples of heterocycles include tetrahydrofuran, morpholine, piperidine, pyrrolidine, and others. In some embodiments, "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms (e.g., N, O, and S) and wherein the nitrogen and sulfur heteroatoms may optionally be oxidized, and the nitrogen may optionally be quaternized, and including any bicyclic group in which any of the above-defined heterocyclic rings is fused to a benzene ring. In some embodiments, heterocycles may include cyclic rings including boron atoms. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H16H-1,5,2-dithiazinyl, 2H-pyrrolyl, 3H-indolyl, 4-piperidonyl, 4a H-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles.

The term "initiator" as used herein generally refers to a substance that initiates a chemical reaction.

The term "ion" as used herein generally refers to an atom(s), radical, or molecule(s) that has lost or gained one or more electrons and has thus acquired an electric charge.

The terms "marine" or "marine substrate" as used herein generally refer to any aqueous environment including sea and freshwater either in the open environment such as the ocean, a lake or river, or any other extensively submerged surface such as the lining of a pipe, a pier or the inner surface of a fish tank, a water intake and discharge systems for reservoirs, for example.

The term "matrix" generally refers to a material, often a polymeric material and/or a prepolymeric material, into which a second material (e.g., a nanostructure) is embedded, surrounded, or otherwise associated. A matrix is typically composed of one or more monomers, but may include other matrix components/constituents. Often the matrix constituents include one or more "addressable" components or complementary binding pairs, that optionally promote assembly and/or cross-linkage of the matrix.

The term "medical device" as used herein generally refers to a device used which pertains to treating or determining the state of one's health. Medical devices are any article that contacts patients or are used in health care, and may be for use either internally or externally.

The term "microbe" as used herein generally refers to a minute life form; a microorganism. In some embodiments, a microbe may include a bacterium that causes disease.

The term "mollusks" as used herein generally refers to any of numerous invertebrate animals of the phylum Mollusca, usually living in water and often having a hard outer shell (e.g., barnacles, clams, oysters). They have a muscular foot, a well-developed circulatory and nervous system, and often complex eyes. Mollusks may include gastropods (snails and shellfish), slugs, octopuses, squids, and the extinct ammonites.

The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal.

The terms "monofunctional", "bifunctional", "trifunctional", and "multifunctional" generally refers to a number of attachment sites a particular compound, molecule, atom, etc. may include (monofunctional having one site, bifunctional having two sites, trifunctional having three sites, and multifunctional having more than one site).

The term "nanocrystal" as used herein generally refers to a nanostructure that is substantially monocrystalline. A nanocrystal thus has at least one region or characteristic dimension with a dimension of less than about 500 nm, e.g., less than about 200 nm, less than about 100 nm, less than about 50 nm, or even less than about 20 nm. The region or characteristic dimension may be along the smallest axis of the structure. Examples of such structures include nanowires, nanorods, nanotubes, branched nanowires, nanotetrapods, nanotripods, nanobipods, nanocrystals, nanodots, quantum dots, nanoparticles, nanoribbons, etc. Nanostructures may be substantially homogeneous in material properties, or in certain embodiments may be heterogeneous (e.g., heterostructures). Optionally, a nanocrystal may comprise one or more surface ligands (e.g., surfactants). The nanocrystal is optionally substantially single crystal in structure (a "single crystal nanostructure" or a "monocrystalline nanostructure"). Nanostructures may be fabricated from essentially any convenient material or material, the nanostructure may be prepared from an inorganic material, e.g., an inorganic conductive or semiconductive material. A conductive or semi-conductive nanostructure often displays 1-dimensional quantum confinement, e.g., an electron may often travel along only one dimension of the structure. Nanocrystals may be substantially homogeneous in material properties, or in certain embodiments may be heterogeneous (e.g., heterostructures). The term "nanocrystal" is intended to encompass substantially monocrystalline nanostructures comprising various defects, stacking faults, atomic substitutions, etc., as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. The nanocrystals may be fabricated from essentially any convenient material or materials.

The terms "nanostructure" or "nanoparticle" are used herein to generally refer to a structure having at least one region or characteristic dimension with a dimension of less than about 500 nm, e.g., less than about 200 nm, less than about 100 nm, less than about 50 nm, or even less than about 20 nm. The region or characteristic dimension may be along the smallest axis of the structure. Examples of such structures include nanowires, nanorods, nanotubes, branched nanocrystals, nanotetrapods, tripods, bipods, nanocrystals, nanodots, quantum dots, nanoparticles, branched tetrapods (e.g., inorganic dendrimers), etc. Nanostructures may be substantially homogeneous in material properties, or in certain embodiments may be heterogeneous (e.g., heterostructures). Nanostructures may be, e.g., substantially crystalline, substantially monocrystalline, polycrystalline, amorphous, or a combination thereof. In one aspect, each of the three dimensions of the nanostructure has a dimension of less than about 500 nm, e.g., less than about 200 nm, less than about 100 nm, less than about 50 nm, or even less than about 20 nm. Nanostructures may comprise one or more surface ligands (e.g., surfactants).

The terms "oligomeric" and "polymeric" are used interchangeably herein to generally refer to multimeric structures having more than one component monomer or subunit.

The term "oral surface" as used herein generally refers to a portion of the mouth and/or something positioned in and/or coupled to a portion of the mouth. For example an oral surface may include, but is not limited to, at least a portion of a tooth, at least a portion of the gum, at least a portion of the tongue, at least a portion of a dental fixture (e.g., a filling, a bridge, a cap a false tooth).

The term "pharmaceutically acceptable salts" includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

The term "personal care" item and/or associated facility as used herein generally refers to a device or system used in or typically associated with a salon (e.g., hair and/or nail) or a day spa, including footbaths, or any device which comes into contact with multiple persons and/or contains such devices, thereby potentially passing along harmful bacteria.

The term "polycyclic," as used herein, generally refers to a chemical compound having two or more atomic rings in a molecule. Steroids are polycyclic compounds. The term "polymerizable compound," as used herein, generally refers to a chemical compound, substituent or moiety capable of undergoing a self-polymerization and/or co-polymerization reaction (e.g., vinyl derivatives, butadienes, trienes, tetraenes, dialkenes, acetylenes, diacetylenes, styrene derivatives).

The term "primer," as used herein, generally refers to an undercoat of paint or size applied to prepare a surface (e.g., for painting).

The term "quaternary ammonium moiety," as used herein, generally refers to a tetravalent charged nitrogen (e.g., $N^+R^3_4$).

The terms "R"'" in a chemical formula refer to a hydrogen or a functional group, each independently selected, unless stated otherwise. In some embodiments the functional group may be an organic group. In some embodiments the functional group may be an alkyl group. In some embodiment, the functional group may be a hydrophobic or hydrophilic group.

The terms "reducing," "inhibiting" and "ameliorating," as used herein, when used in the context of modulating a pathological or disease state, generally refers to the prevention and/or reduction of at least a portion of the negative consequences of the disease state. When used in the context of an adverse side effect associated with the administration of a drug to a subject, the term(s) generally refer to a net reduction in the severity or seriousness of said adverse side effects.

The term "sealant," as used herein, generally refers to any of various liquids, paints, chemicals, or soft substances that may be applied to a surface or circulated through a system of pipes or the like, drying to form a hard, substantially watertight coating. When used in the context of dentistry sealant generally refers to any of several transparent synthetic resins applied to the chewing surfaces of an oral cavity as a preventive measure against tooth decay in the occlusal pits and fissures.

The term "self-cleaning" (e.g., surfaces) as used herein generally refers to a surface which inhibits adhesion of matter to the surface. Self-cleaning generally refers to the mechanisms of adhesion between two surfaces which are in contact. These systems generally attempt to reduce their free surface energy. If the free surface energies between two components are intrinsically very low, it may generally be assumed that there will be weak adhesion between these two components. The important factor here is the relative reduction in free surface energy. In pairings where one surface energy is high and one surface energy is low the crucial factor is very often the opportunity for interactive effects, for example, when water is applied to a hydrophobic surface it is impossible to bring about any noticeable reduction in surface energy. This is evident in that the wetting is poor. The water applied forms droplets with a very high contact angle. Perfluorinated hydrocarbons (e.g., polytetrafluoroethylene) have very low surface energy. There are hardly any components which adhere to surfaces of this type, and components deposited on surfaces of this type are in turn very easy to remove. The term self-cleaning as used herein also generally refers to a chemical transformation of a contaminant that comes into contact with the surface such that it is broken down by oxidative decomposition (e.g., photooxidation by a metal oxide such as photocatalytic oxidation of phenol or E. Coli inactivation due to photooxidation by $TiO_2$).

The term "substituted alkyl" as used herein generally refers to an alkyl group with an additional group or groups attached to any carbon of the alkyl group. Substituent groups may include one or more functional groups such as alkyl, lower alkyl, aryl, acyl, halogen, alkylhalo, hydroxy, amino, alkoxy, alkylamino, acylamino, acyloxy, aryloxy, aryloxyalkyl, mercapto, both saturated and unsaturated cyclic hydrocarbons, heterocycles, and other organic groups.

The term "substituted alkyl-aryl" as used herein generally refers to an alkyl-aryl group with an additional group or groups attached to any carbon of the alkyl-aryl group. Additional groups may include one or more functional groups such as lower alkyl, aryl, acyl, halogen, alkylhalo, hydroxy, amino, alkoxy, alkylamino, acylamino, acyloxy, aryloxy, aryloxyalkyl, thioether, heterocycles, both saturated and unsaturated cyclic hydrocarbons which are fused to the aromatic ring(s), coupled covalently or coupled to a common group such as a methylene or ethylene group, or a carbonyl coupling group such as in cyclohexyl phenyl ketone, and others.

The term "substituted aryl" as used herein generally refers to an aryl group with an additional group or groups attached to any carbon of the aryl group. Additional groups may include one or more functional groups such as lower alkyl, aryl, acyl, halogen, alkylhalo, hydroxy, amino, alkoxy, alkylamino, acylamino, acyloxy, aryloxy, aryloxyalkyl, thioether, heterocycles, both saturated and unsaturated cyclic hydrocarbons which are fused to the aromatic ring(s), coupled covalently or coupled to a common group such as a methylene or ethylene group, or a carbonyl coupling group such as in cyclohexyl phenyl ketone, and others.

The term "substituted heterocycle" as used herein generally refers to a heterocyclic group with an additional group or groups attached to any element of the heterocyclic group. Additional groups may include one or more functional groups such as lower alkyl, aryl, acyl, halogen, alkylhalos, hydroxy, amino, alkoxy, alkylamino, acylamino, acyloxy, aryloxy, aryloxyalkyl, thioether, heterocycles, both saturated and unsaturated cyclic hydrocarbons which are fused to the heterocyclic ring(s), coupled covalently or coupled to a common group such as a methylene or ethylene group, or a carbonyl coupling group such as in cyclohexyl phenyl ketone, and others.

The term "substrate" as used herein generally refers to a body or base layer or material (e.g., onto which other layers are deposited).

The term "thioether" as used herein generally refers to the general structure R—S—R' in which R and R' are the same or different and may be alkyl, aryl or heterocyclic groups. The group —SH may also be referred to as "sulfhydryl" or "thiol" or "mercapto."

Bridged Polycyclic Antimicrobials

New antimicrobials are required to combat the new antimicrobial resistant microbes. New antimicrobials may be effective verses microbes which are currently resistant to currently known antimicrobials. New antimicrobials may resist leaching off into the environment beyond a predetermined amount to inhibit polluting the environment unnecessarily (which may concurrently increase the occurrence of antimicrobial resistant microbes from overexposure of antimicrobials).

One strategy for combating antimicrobial resistant organisms is by modifying known antimicrobials to increase their effectiveness. In some embodiments, quaternary ammonium compounds may be modified to increase their effectiveness. It is typically thought that quaternary ammonium compounds denature the proteins of the bacterial or fungal cell, affect the metabolic reactions of the cell and allow vital substances to leak out of the cell, finally causing death. In addition, quaternary ammonium compounds are not known to be toxic towards higher forms of life (e.g., humans).

One of the main considerations in examining the mode of action is the characterization of quaternary ammonium compounds as cationic surfactants. This class of chemical reduces the surface tension at interfaces, and is attracted to negatively charged surfaces, including microorganisms. Quaternary ammonium compounds denature the proteins of the bacterial or fungal cell, affect the metabolic reactions of the cell and allow vital substances to leak out of the cell, finally causing death.

Most uses of quaternary ammonium compounds as antimicrobials involve formulations of disinfectants and sanitizers which are not bound to a surface, resulting in effluent stream pollution and contamination. They are simply wetted onto the surface such as in disinfecting wipes which are primarily ammonium. salts as their liquid active ingredient. When they are incorporated into surfaces they are not crosslinked but are allowed to float to the surface thereby becoming depleted over time the same way silver and triclosan are incorporated in plastics. Coupling quaternary ammonium compounds to a surface or formation within a polymer matrix may inherently reduce the effectiveness of the quaternary ammonium compounds, by decreasing the accessibility of microbes to the most active cationic portion of the molecule. Increasing accessibility to the quaternary ammonium compounds within a surface coating or with any use increases the effectiveness of the quaternary ammonium compound.

In some embodiments, the effectiveness of an antimicrobial (e.g., quaternary ammonium compound) may be increased by coupling the antimicrobial within or on a curved surface, where the curved surface is on a molecular scale. For example, a curved surface may be created using nanoparticles (e.g., spherical nanoparticles). Nanoparticles may incorporate into their structure antimicrobial compounds with greater exposed surface area due to the curved surface of the nanoparticle.

In some embodiments, a compound may include a nanoparticle. The nanoparticle may include a bridged polycyclic compound. A compound may be formed using self-assembly techniques and principles. A compound may be formed from portions which are themselves antimicrobial (e.g., quaternary ammonium compounds). A compound may bind moieties to at least portions of itself which have, for example, antimicrobial properties.

In some embodiments, a protective coating composition may include a compound. A compound may be a bridged polycyclic compound. A bridged polycyclic compound may be a cavitand. Portions of the bridged polycyclic compound may include two or more quaternary ammonium moieties. The protective coating composition may be antimicrobial.

In some embodiments, a composition may include one or more bridged polycyclic compounds. At least one of the bridged polycyclic compounds may include at least two cyclic groups. A general example of a bridged polycylic compound including only two cyclic groups may include, but is not limited to, a compound 100 having a general structure

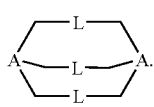

In some embodiments, at least two cyclic groups may be defined in part by quaternary ammonium moieties, by the nitrogen of the quaternary ammonium moiety comprising one of the atoms which forms a part of the cyclic structure itself. For example, a cyclic structure which is formed at least in part by a quaternary ammonium moiety may include, but is not limited to structure 101

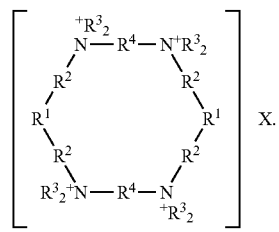

Structure 101 is an example of quaternary ammonium moieties defining at least in part a cyclic group, however, compound 101 is not an example of a polycyclic compound and compound 101 is not an example of a bridged polycyclic compound.

In some embodiments, a bridged polycyclic compound may include at least two quaternary ammonium moieties, at least three quaternary ammonium moieties, at least four quaternary ammonium moieties, at least five quaternary ammonium moieties, at least six quaternary ammonium moieties, at least seven quaternary ammonium moieties, or at least eight quaternary ammonium moieties.

In some embodiments, a compound 100 may have a general structure

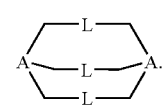

Compound 100 may be formed by coupling a trifunctional corner unit A with a bifunctional linker unit L as depicted in Scheme 2.

Scheme 2.
Schematic depiction of the formation of compound 100.

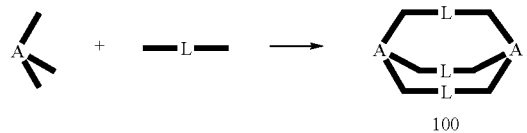

Scheme 2 should not be used as to limit the disclosure set forth herein. Corner unit A may include multiple dentate linkers other than the one depicted in Scheme 2 (e.g., a trifunctional linker A is depicted in Scheme 2) including, but not limited to, bifunctional, tetrafunctional (e.g., compound 100a) etc. In some embodiments, a corner unit A may be coupled to a linker unit L in any multitude of ways known to one skilled in the art.

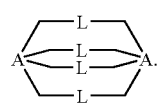

In some embodiments, a compound 100c may have a general structure

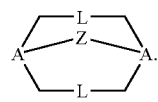

Compound 100c may be a bridged polycyclic compound. Compound 100c may be antimicrobial. In some embodiments, Z may include at least one bridge. Bridge Z may couple 2 non adjacent atoms.

In some embodiments, at least one of the bridges is —$R^2$—$N^+R^3_2$—$R^4$—$N^+R^3_2$—$R^2$—, such that each bridge independently couples A to A. In some embodiments, at least one of the bridges may be —$R^2$—$N^+R^3_2$—$R^4$—$N^+R^3_2$—$R^2$—. Each bridge may independently couple A to A. In some embodiments, at least one of the bridges may be —$R^2$—$NR^3$—$R^4$—$N^+R^3_2$—$R^2$—. Each bridge may independently couple A to A. In some embodiments, at least one of the bridges may be —$R^2$—N=$R^4$=N—$R^2$—. Each bridge may independently couple A to A.

For example when Z is 1 compound 100c may be a compound 100 having a general structure

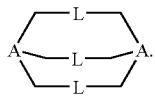
100

When, for example, Z is 2 a compound 100c may be a compound 100a having a general structure

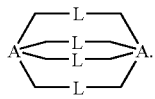
100a

When, for example, Z is 2 a compound 100c may be a compound 100d having a general structure

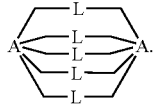
100d

In some embodiments, a compound may include a bridged polycyclic compound formed from two corner units (e.g., compound 100b). Compound 100b may be formed by coupling a multifunctional (e.g., trifunctional) corner unit A with a second multifunctional (e.g., trifunctional) corner unit A as depicted in Scheme 2a.

Scheme 2a.
Schematic depiction of the formation of compound 100b.

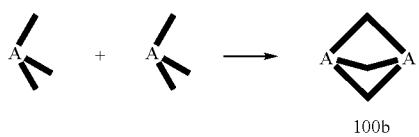
100b

In some embodiments, a compound 102 may have a general structure

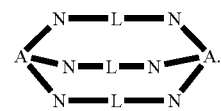
102

Compound 102 may include a moiety coupling corner unit A with linker unit L, the moiety including a nitrogen.

In some embodiments, a compound 103 may have a general structure

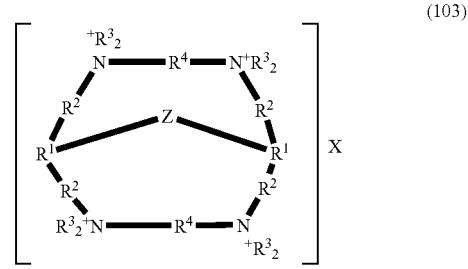
(103)

In some embodiments, $R^1$ may be independently alkyl, substituted alkyl, aryl, substituted aryl, N, $N^+R^3$, heterocycle, or substituted heterocycle. $R^2$ may be independently alkyl, substituted alkyl, aryl, substituted aryl, heterocycle, substituted heterocycle, covalent bond, or alkene. $R^3$ may be independently alkyl, substituted alkyl, aryl, substituted aryl, heterocycle, substituted heterocycle, alkene, ether, PEG, or PEI. $R^4$ may be independently alkyl, substituted alkyl, aryl, substituted aryl, $N^+R^3$, heterocycle, substituted heterocycle, alkyl ether, PEG, PEI, ether, or alkene. $R^4$ may independently include amide, alcohol, ester, sulfonamide, or sulfanilamide. $R^4$ may be independently alkyl, substituted alkyl, aryl, substituted aryl, heterocycle, substituted heterocycle, ether, amide, alcohol, ester, sulfonamide, sulfanilamide, or alkene. X may be one or more counter ions. Z may include at least one bridge.

In some embodiments, at least one of the bridges may be —$R^2$—$N^+R^3_2$—$R^4$—$N^+R^3_2$—$R^2$—. Each bridge may independently couple $R^1$ to $R^1$. In some embodiments, at least one of the bridges may be —$R^2$—$NR^3$—$R^4$—$N^+R^3_2$—$R^2$—. Each bridge may independently couple $R^1$ to $R^1$. In some embodiments, at least one of the bridges may be —$R^2$—$NR^3$—$R^4$—$NR^3$—$R^2$—. Each bridge may independently couple $R^1$ to $R^1$. In some embodiments, at least one of the bridges may be —$R^2$—N=$R^4$=N—$R^2$—. Each bridge may independently couple $R^1$ to $R^1$.

For example when Z is 1 compound 103 may be a compound 104 having a general structure

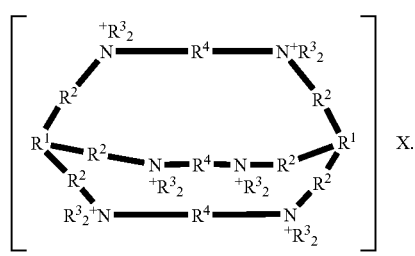
104

When, for example, Z is 2 a compound 103 may be a compound 104 a having a general structure

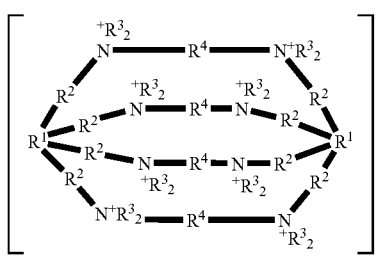

In some embodiments, a compound 104 may have a general structure

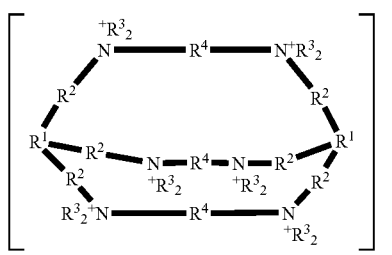

In some embodiments, $R^1$ may be alkyl, substituted alkyl, aryl, substituted aryl, $N^+R^3$, heterocycle, or substituted heterocycle. $R^2$ may be alkyl, substituted alkyl, aryl, substituted aryl, $N^+R^3$, heterocycle, substituted heterocycle, covalent bond, or alkene. $R^3$ may be alkyl, substituted alkyl, aryl, substituted aryl, $N^+R^3$, heterocycle, substituted heterocycle, alkyl ether, PEG, PEI, or alkene. $R^4$ may be alkyl, substituted alkyl, aryl, substituted aryl, $N^+R^3$, heterocycle, substituted heterocycle, alkyl ether, PEG, PEI, ether, or alkene. $R^4$ may include amide, alcohol, ester, sulfonamide, or sulfanilamide. X may be one or more counter ions.

In some embodiments, counterions may include one or more halogens (e.g., Br, Cl, I, etc.). A specific embodiment of a halogen counterion may include Iodine which has proven as a more effective counterion for bridged polycyclic antimicrobial compounds. As has been discussed herein, counterions may affect the properties of the chemical compound and subsequent composition. Boron based counterions may increase certain antimicrobial properties (e.g., $BF_4^-$).

In some embodiments, salts of specific counterions may be added to an antimicrobial composition to increase the effectiveness of the composition. For example, any of the counterions described herein for use in making the bridged polycyclic compound (e.g., counterions which increase the antimicrobial effectiveness of the compound), may be added to the composition later (e.g., as a salt such as sodium or potassium tetrafluoroborate). In some embodiments, a combination of the two strategies may be used, additionally allowing for two or more different counterions or salts to be included in the final formulation of the composition. Each of the counterions and/or salts may increase the antimicrobial effectiveness of the composition in a different manner. Other examples of counterions (which may be added as an appropriate salt later) may include an anion, a polymer, a monomer, a halogen, an iodine, a bromine, a chlorine, a triflate, a tosylate, a boron, a borate, tetrafluoroborate, a nitrogen containing gourp, a nitrate, a halogen, a hexafluorophosphate, or an $NTf_2$ (wherein Tf is bis(trifluoromethanesulfonyl)imide).

In some embodiments, a compound may include one or more guest molecules coupled to the compound such as compound 106 having a general structure

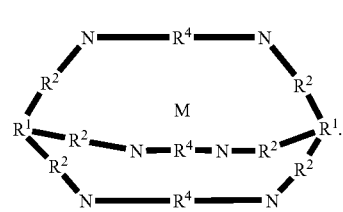

In some embodiments, $R^1$ may be alkyl, substituted alkyl, aryl, substituted aryl, N, $N^+R^3$, heterocycle, or substituted heterocycle. $R^2$ may be alkyl, substituted alkyl, aryl, substituted aryl, $N^+R^3$, heterocycle, substituted heterocycle, covalent bond, or alkene. $R^3$ may be alkyl, substituted alkyl, aryl, substituted aryl, $N^+R^3$, heterocycle, substituted heterocycle, alkyl ether, PEG, PEI, or alkene. $R^4$ may be alkyl, substituted alkyl, aryl, substituted aryl, $N^+R^3$, heterocycle, substituted heterocycle, alkyl ether, PEG, PEI, ether, or alkene. M may include one or more guest molecules associated with one or more portions of compound 107 (e.g., amines). M may be one or more metals. M may include silver, zinc, copper, gold, calcium, nickel, cobalt, barium, strontium, lead, lanthanum, iron, manganese, cadmium, magnesium, yttrium, lanthanum, cesium, praseodymium, neodymium, europium, gadolinium, terbium, dysprosium, holmium, erbium, thulium, ytterbium, or alkaline earth metals or cesium. In some embodiments, M may include organic cation salts as templates (e.g., trimethyl ammonium, etc.). M may include light activated elements such that an antimicrobial property of M is increased. X may be one or more counter ions.

In some embodiments, M may be one or more guest molecules. X may be one or more counter ions. M (e.g., Ag+ counter ion) may bind thereby keeping M in close proximity (e.g., F-ions have been reported and verified by x-ray single crystal structure to bind in ammonium salt cavitands). An anion may bind to an ammonium thus affording a close association of the cation counterion. In some embodiments, M may pi-bond coordinate to $R_4$ (e.g., aryl) or a heterocycle binding (e.g., pyridiyl $R_4$ nitrogen to a Ag+ or a phenol —OH or O-binding to the Ag+).

In some embodiments, M may be two silver metals associated with compound 107 forming a compound 107 a having the general structure

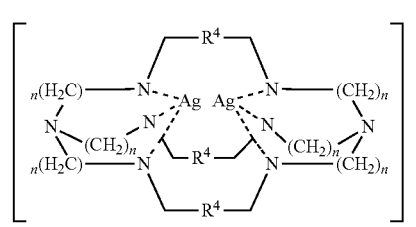

In some embodiments, a compound may include one or more guest molecules coupled to the compound such as compound 108 having a general structure

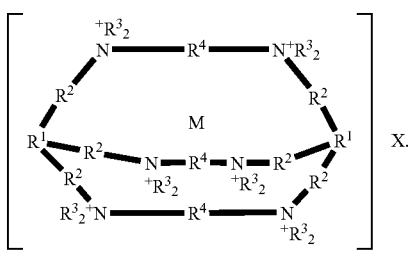

In some embodiments, R¹ may be alkyl, substituted alkyl, aryl, substituted aryl, N⁺R³, heterocycle, or substituted heterocycle. R² may be alkyl, substituted alkyl, aryl, substituted aryl, N⁺R³, heterocycle, substituted heterocycle, covalent bond, or alkene. R³ may be alkyl, substituted alkyl, aryl, substituted aryl, N⁺R³, heterocycle, substituted heterocycle, alkyl ether, PEG, PEI, or alkene. R⁴ may be alkyl, substituted alkyl, aryl, substituted aryl, N⁺R³, heterocycle, substituted heterocycle, alkyl ether, PEG, PEI, ether, or alkene. M may be one or more metals. M may include silver, zinc, copper, gold, calcium, nickel, cobalt, barium, strontium, lead, lanthanum, iron, manganese, cadmium, magnesium, yttrium, lanthanum, cesium, praseodymium, neodymium, europium, gadolinium, terbium, dysprosium, holmium, erbium, thulium, ytterbium, or alkaline earth metals or cesium. In some embodiments, M may include organic cation salts as templates (e.g., triethyl ammonium, etc.). M may include light activated elements such that an antimicrobial property of M is increased. X may be one or more counter ions.

It should be understood that any of the compounds depicted herein may or may not have one or more metals coupled to the structure. For example, a structure depicted with a metal associated with the compound also includes a compound without a metal associated with the compound. A structure depicted without a metal associated with the compound also includes a compound with a metal associated with the compound. Although in many instances metals depicted herein are shown positioned within a space defined by compounds described herein, this should not be seen as limiting, metals may be coupled (e.g., complexed to) to a compound along an outer surface of the compound.

Metals may include any elements in the periodic chart designated as metals, known to one skilled in the art. In some embodiments, metals may include any cationic metal known to one skilled in the art (e.g., Zn, Cu, Au, Ag, Cs, Mn, Mg, Ca, Ni, Co, etc.). In some embodiments, metals may include metals which have antimicrobial properties and/or anti-inflammatory properties (e.g., Ag, Zn, etc.). In some embodiments, metals may function to couple one or more atoms or molecules within a compound (e.g., compound 108) and/or to the surface of the compound. In some embodiments, one or more metals coupled to a compound may include one or more inorganic/organometallic compounds. A compound (e.g., a bridged polycyclic compound) may include two or more different metals coupled (e.g., associated in some way) to the compound. In some embodiments, a metal may be coupled to a bridged polycyclic molecule.

In some embodiments, R¹ may be N⁺(1-22C alkyl), N⁺(1-12C alkyl), N⁺(1-6C alkyl), N⁺(6C alkyl), N⁺R³,

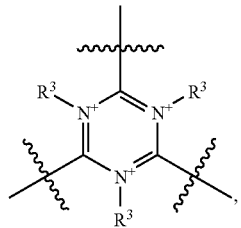

cyclam, aza crown ether, tris ethylamine N substituted cyclam, or

In some embodiments, R² may be 1-2C alkyl, 1-6C alkyl, 2-4C alkyl, CH₂, or a bond (e.g., covalent, ionic) between R¹ and a N of, for example, compound 108.

In some embodiments, R³ may be hydrophobic or hydrophilic. R³ may be 1-3C alkyl, 4-5C alkyl, 6-10C alkyl, 7-9C alkyl, 10-22C alkyl, 15-22C alkyl, 6-10C alkyl ether, 7-9C alkyl ether, methyl, PEI (polyethyleneimine), or PEG (polyethyleneglycol). R³ may be 6C alkyl. R³ may be a polymer. R³ may be an oxazoline polymer.

In some embodiments, R⁴ may be an aryl, substituted aryl, heterocycle, or substituted heterocycle. R⁴ may

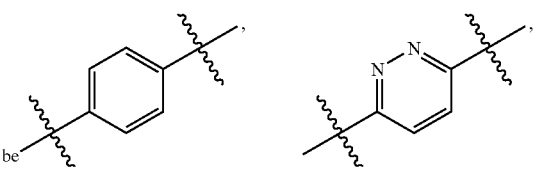

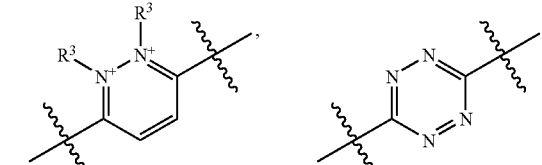

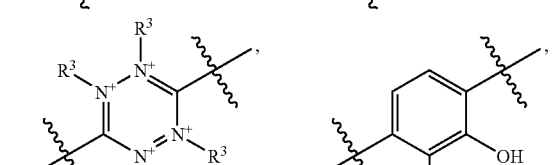

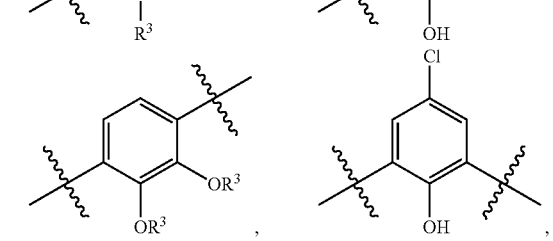

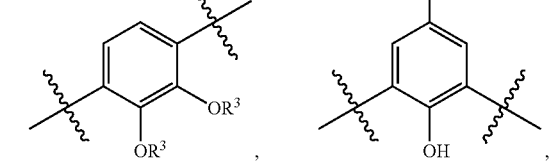

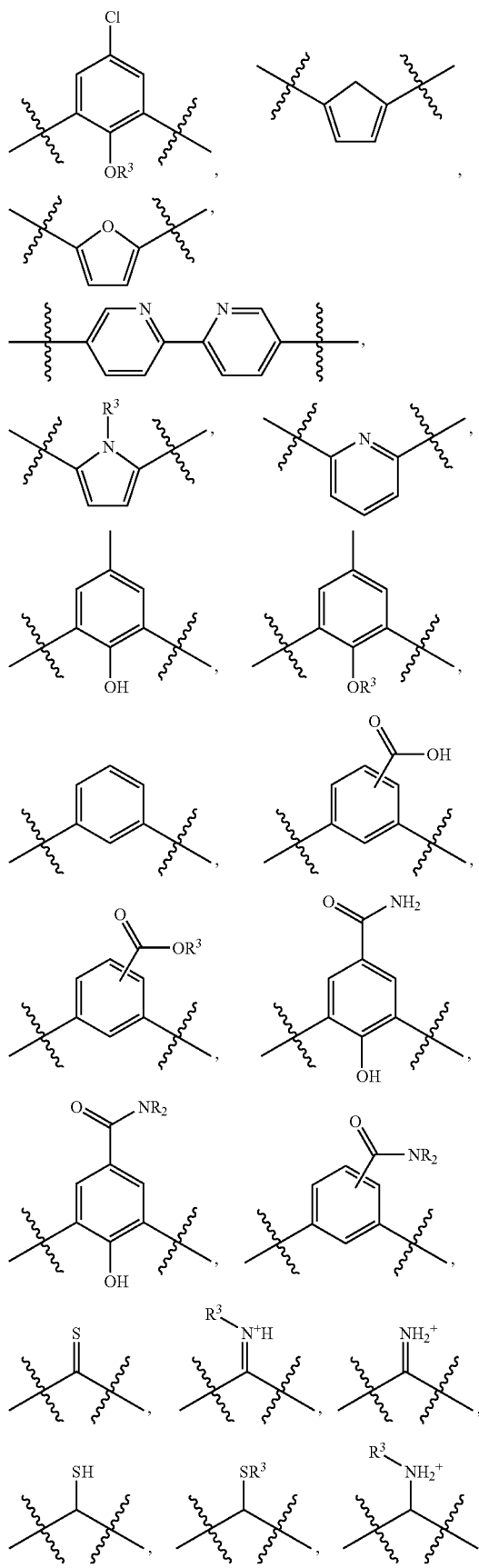

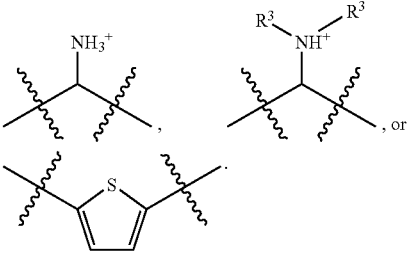

Forming one or more portions of a compound from one or more aromatic rings may provide advantages.

Advantages may include providing rigidity to the compound enhancing the stability of the compound. Aromatic rings may facilitate the self-assembly of the constituent parts of the compound. Other advantages may include pie stacking of compounds relative to one another or of "guests" positioned within the compound. A substituted aryl or heterocycle may include moieties (e.g., N) which bind to other elements (e.g., metals such as silver) or molecules.

$R^4$ may include substituents (e.g., $R^3$) which effect properties of a compound as a whole (e.g., hydrophobicity, hydrophilicity, self-cleaning, antimicrobial, cross-coupling properties).

In some embodiments, a compound 108 may include an embodiment such as compound 110 having a general structure

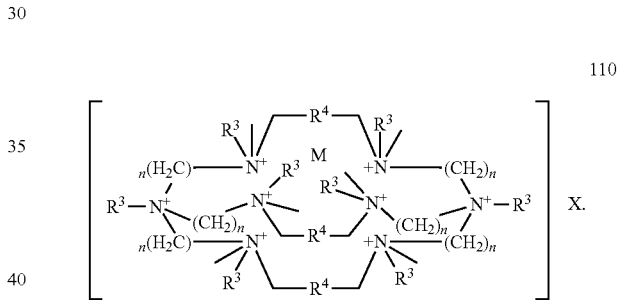

In some embodiments, $R^3$ may be alkyl, substituted alkyl, aryl, substituted aryl, $N^+R^3$, heterocycle, substituted heterocycle, alkyl ether, PEG, PEI, or alkene. $R^4$ may be alkyl, substituted alkyl, aryl, substituted aryl, $N^+R^3$, heterocycle, substituted heterocycle, alkyl ether, PEG, PEI, ether, or alkene. M may include one or more "guest" molecules (e.g., one or more metals). X may be one or more counter ions.

In some embodiments, M may be two silver metals associated with compound 110 forming a compound 112 having the general structure

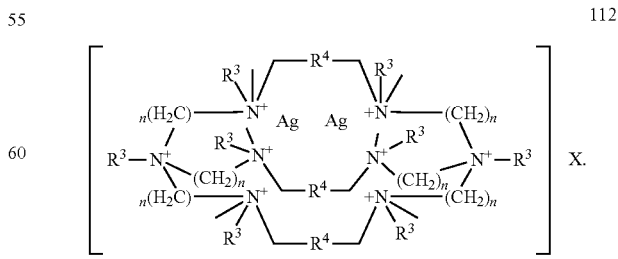

In some embodiments, $R^3$ may be alkyl, substituted alkyl, aryl, substituted aryl, $N^+R^3$, heterocycle, substituted heterocycle, alcyl ether, PEG, PEI, or alkene. R⁴ may be alkyl, substituted alkyl, aryl, substituted aryl, N⁺R³, heterocycle, substituted heterocycle, alkyl ether, PEG, PEI, ether, or alkene. M may be one or more guest molecules. X may be one or more counter ions. M (e.g., Ag+ counter ion) may bind thereby keeping M in close proximity (e.g., F-ions have been reported and verified by x-ray single crystal structure to bind in ammonium salt bridged polycyclic molecules). An anion may bind to an ammonium thus affording a close association of the cation counterion. In some embodiments, M may pi-bond coordinate to R⁴ (e.g., aryl) or a heterocycle binding (e.g., pyridiyl R⁴ nitrogen to a Ag+ or a phenol —OH or O-binding to the Ag+).

In some embodiments, a compound 104 may include an embodiment such as compound 111 having a general structure

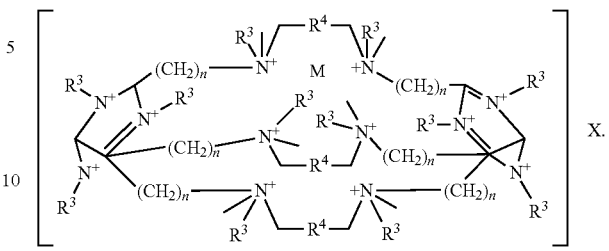

114

In some embodiments, R³ may be alkyl, substituted alkyl, aryl, substituted aryl, N⁺R³, heterocycle, substituted hetero-

111

8 Br⁻.

In some embodiments, a compound 104 may include any number of combination of embodiments such as compound 113 having a general structure

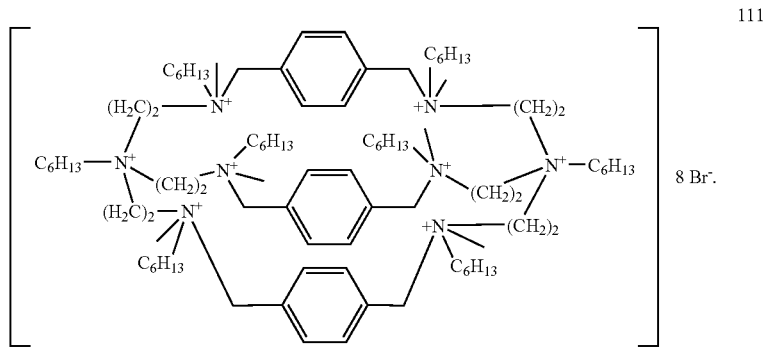

113

Where:
113a is $R^{3.1}=C_6H_{13}$, $R^{3.2}=CH_3$ and $R^{3.3}=R^{3.1}$ or $R^{3.2}$
113b is $R^{3.1}=C_8H_{17}$, $R^{3.2}=CH_3$ and $R^{3.3}=R^{3.1}$ or $R^{3.2}$
113c is $R^{3.1}=C_{10}H_{21}$, $R^{3.2}=CH_3$ and $R^{3.3}=R^{3.1}$ or $R^{3.2}$
113d is $R^{3.1}=C_{12}H_{25}$, $R^{3.2}=CH_3$ and $R^{3.3}=R^{3.1}$ or $R^{3.2}$
113e is $R^{3.1}=C_6H_{13}$, $R^{3.2}=CH_2Ph$ and $R^{3.3}=R^{3.1}$ or $R^{3.2}$
113f is $R^{3.1}=C_{12}H_{25}$, $R^{3.2}=CH_2Ph$ and $R^{3.3}=R^{3.1}$ or $R^{3.2}$
113h is $R^{3.1}=C_4H_9$, $R^{3.2}=CH_3$ and $R^{3.3}=R^{3.1}$ or $R^{3.2}$ In some embodiments, a compound 104 may include a an embodiment such as compound 114 having a general structure cycle, alkyl ether, PEG, PEI, or alkene. R⁴ may be alkyl, substituted alkyl, aryl, substituted aryl, N⁺R³, heterocycle, substituted heterocycle, alkyl ether, PEG, PEI, ether, or alkene. M may be one or more metals. X may be one or more counter ions.

Substituents (e.g., R³) may be configured to perform a variety of functions. By using different substituents, properties of a compound such as the bridged polycyclic compounds described herein may be customized to meet a particular industrial and/or individual's need. For example, R³ may be hydrophobic or hydrophilic depending upon the specific property needed.

In some embodiments, a substituent (e.g., R³) may be multifunctional such that it imparts two or more properties to a formed compound. For example a substituent (e.g., R³) may function to increase the hydrophilicity of a compound, as well as, function as a cross-coupling reagent to cross-link compounds to one another under appropriate conditions (e.g., a substituent may include one or more heteroatoms within its structure such as N, O, and S).

In some embodiments, substituents such as R³ may function to enhance hydrophobicity and/or lipophilicity. Depending upon the needs of a customer the hydrophobicity/lipophilicity of a compound may be increased. Adjusting the hydrophobicity/lipophilicity of a compound may consequently adjust the solubility of the compound in a particular solvent and/or matrix. Increasing the liphophilicity of a substituent (e.g., R³) coupled to an ammonium salt may increase the anti-microbial activity of a compound. In some embodiments, a compound may have a minimum inhibitory concentration (MIC) of less than 900 μM, of less than 600 μM, or of less than 300 μM. A discussion of relationship between substituent chain length and antimicrobial activity of quaternary ammonium salts may be found in Pernak et al., "Synthesis and anti-microbial activities of some pyridinium salts with alkoxymethyl hydrophobic group" *Eur. J. Med. Chem.* 36 (2001) 899-907, which is incorporated by reference as if fully set forth herein.

The relationship between substituent chain length and antimicrobial activity is demonstrated in tests conducted on 113a, 113b, 113d, 113e, and 113h detailed herein in the Examples portion. A series of bridged polycyclic compounds were synthesized wherein different substituents were coupled to the quaternary ammonium moieties. Substituents included C1, C4, C6, C8, C12, and benzyl in combinations of C1 with C4, C6, C8, and C12, as well as, combinations of benzyl with C6 and C12. Time kill and residual surface tests of the antimicrobial strength of the compounds were tested against examples of gram+bacteria (e.g., *Staphylococcus aureus*, most common surgical wound infection), gram—bacteria (e.g., *Escherichia coli*, most commonly acquired hospital infection), and fungus (e.g., *Aspergillus niger*, a toxic black mold found in residences). Of the various alkyl chains combined with C1 tested, the C6, C1 compound tested as the strongest antimicrobial compound. When the test results of the C6, C1 were compared to the benzyl derivatives, once again, the C6,C1 derivative tested as the overall strongest antimicrobial.

The 113a C6C1 compound is unique in regards to the relatively short alkyl chain vs. known quaternary antimicrobials and high antimicrobial activity. Discrete quaternary ammonium or pyridinium antimicrobial molecules usually possess long alkyl chains. The most effective discrete (e.g., noncyclic) quaternary ammonium or pyridinium salt antimicrobials have an alkyl chain length between 12 and 18 carbon atoms as described by T. Loftsson et. al. in *J. Med. Chem.* 46, 2003, 4173-4181, which is incorporated by reference as if fully set forth herein.

In general it is known in the art that quaternary ammonium compounds are effective biocidal agents when they possess an alkyl chain with at least eight carbon atoms (S. Block, 'Disinfection, Sterilization and Preservation', $3^{rd}$ Ed., Lea and Febiger, Philadelphia, Pa., 1983; cited in 'Recent Advances in Antimicrobial Dendrimers', S. L. Cooper et. al. *Adv. Mater.* 2000, 12, no. 11, 843-846, which is incorporated by reference as if fully set forth herein). In a study of dendrimer quaternary ammonium salts, dendriter biocides carrying $C_{10}$ alkyl chains were the most potent (S. L. Cooper et.al. *Biomacromolecules*, 1 (3), 473 480, 2000), which is incorporated by reference as if fully set forth herein.

Typically, non-discrete polymers are some of the only antimicrobials to show any appreciable antimicrobial activity with alkyl groups of <8 carbons. However, non-discrete polymers (e.g. polyethyleneimine quaternary ammonium containing polymers) demonstrated weaker overall antimicrobial activity in antimicrobial residual surface tests (A. M. Klibanov et.al. *Biotechnology Letters*, 25, 2003, 1661-1665), which is incorporated by reference as if fully set forth herein.

Furthermore, the straightforward route and synthesis efficiency makes bridged polycyclic compounds (e.g., 113a) more attractive from a manufacturing standpoint over the more laborious methods required for typical dendrimer synthesis. Both bridged polycyclic compounds (e.g., 113a) and dendrimers have the advantage of being polyvalent (multiple positively charged sites on one molecule to attract microbes) affording increased activity vs. traditional discrete quaternary ammonium salts (S. L. Cooper et. al. U.S. Pat. No. 6,440, 405). However, the dendrimer synthesis requires large volumes of solvents/reagents relative to obtained product and long periods of time (days) to synthesize as described by S. L. Cooper et. al. in U.S. Pat. No. 6,440,405, which is incorporated by reference as if fully set forth herein.

In some embodiments, substituents such as $R^3$ may function to enhance hydrophilicity and/or lipophobicity. Depending upon the needs of a customer the hydrophilicity/lipophobicity of a bridged polycyclic compound may be increased. Adjusting the hydrophilicity/lipophobicity of a compound may consequently adjust the solubility of the compound in a particular solvent and/or matrix.

In some embodiments, substituents such as $R^3$ may function to enhance the self-cleaning properties of which the compound may impart to a surface to which the compound is coupled. In some embodiments, substituents may enhance the antimicrobial properties of the compound. Self-cleaning and antimicrobial properties may function in combination with one another.

The search for self-cleaning surfaces has come about from the observation of such surfaces occurring naturally in nature, such as lotus leaves. To clean a surface, material has to be transported along it, and best, off it. By tuning the wettability of the substrate, two basic options arise. The surface may be rendered very wettable, and the decontamination process is based on film flow. But, interestingly, biology hints at a different option. Non-wettable plant leaf surfaces, such as those of the famous Lotus plant, have a built-in elementary cleaning mechanism. This was noticed in the mid-nineties by botanists studying plant surfaces. They observed that droplets running off the leaves may carry dry contaminants along—the origin for the Lotus leaf's status as a sacred object of purity. It is widely held that self-cleaning surfaces are a combination of low surface-energy species and a peculiar topographic feature based on dual-size roughness: the coarse-scale rough structure is about 10-20 µm, whereas the finer structure on top of the coarse structure is in the range of 100 nm to 1 µm. The dual-size structure has proven to be vital in generating the superhydrophobicity of the lotus leaves, especially for obtaining low water rolloff angles. Techniques for forming superhydrophobic surfaces may be found in Ming et al., "Superhydrophobic Films from Raspberry-like Particles" *Nano Lett.*, 5 (11), 2298-2301, 2005, which is incorporated by reference as if fully set forth herein.

In some embodiments, a first compound described herein may include a plurality of second compounds coupled to the surface of the first compound. The first compound may be several times larger than the second compound. The first compound may be an order of magnitude or larger than the second compound. The first compound may include, but is not limited to, compounds such as compound 100 Second compounds may be coupled to active sites on the first compound to form a third compound. In some embodiments, the second compound may include, but is not limited to, compounds such as compound 100, coupled to active sites of a first compound. Coupling the third compound to a surface may provide the necessary surface topography (e.g., a dual-roughness) to produce a self-cleaning surface.

In some embodiments, a topology of a surface treated with the coating compositions described herein may have at least one layer having elevations whose average height may be from 20 nm to 25 µm and whose average separation is from 20 nm to 25 µm, whose average height is from 50 nm to 10 µm and/or whose average separation is from 50 nm to 10 µm, or whose average height is from 50 nm to 4 µm and/or whose average separation is from 50 nm to 4 µm. The topology of a surface treated with the coating compositions described herein may have elevations whose average height is from 0.25 to 1 µm and whose average separation is from 0.25 to 1 µm. The average separation of the elevations is the separation between the highest elevation of an elevation and the most adjacent highest elevation. If an elevation has the shape of a cone, the tip of the cone is the highest elevation of the elevation. If the elevation is a rectangular parallelepid, the uppermost surface of the rectangular parallelepid is the highest elevation of the elevation.

In some embodiments, a hydrophobic coating may be applied over a protective coating including a self-cleaning topological surface.

In some embodiments, substituents (e.g., $R^3$) coupled to portions of a compound may function as the finer structure relative to the coarser structure of the compounds. Substituents such as $R^3$ may increase the hydrophobicity of the compounds to which the substituents are coupled.

However, a disadvantage of the hydrophobic surfaces is that if the structures are sufficiently complicated, (e.g., moldings with undercuts or porous moldings or sponges, water may not then penetrate these voids) the result being that the cleaning properties of the surface may be inhibited. The globular shape of the water droplets on these surfaces may cause visual impairment if the droplets do not roll off from the surface because the surface is, for example, horizontal. In such instances, highly wettable surfaces may be advantageous, since a water droplet on these becomes distributed over almost the entire surface and forms a film of minimum thickness. This occurs in particular if the surface tension of the water is reduced by appropriate means (e.g., surfactants) and/or a hydrophilic surface is present. In some embodiments, hydrophilic substituents (e.g., $R^3$) may be coupled to active sites (e.g., amines) on compounds described herein. In some embodiments, hydrophilic substituents/coatings (e.g., hydrophilic silicas) may be coupled to compounds described herein. A discussion of hydrophilic substances and particles may be found in U.S. Patent Application, Publication No. 20050118911 to Oles et al. ("Oles"), which is incorporated by reference as if fully set forth herein. Increasing the hydrophilicity of a surface may inhibit microbial adhesion. Substituents for inhibiting microbial adhesion may be found in Ming et al., "Bacterial Adhesion at Synthetic Surfaces" *APPLIED AND ENVIRONMENTAL MICROBIOLOGY*, November 1999, p. 4995-5002, which is incorporated by reference as if fully set forth herein.

A self-cleaning surface including compounds may be enhanced by decreasing the surface energy or increasing the hydrophobicity of the self-cleaning surface. Several different techniques may be used in combination with compounds to increase the hydrophobicity and self-cleaning properties of a surface.

In some embodiments, a surface may be first coated with a hydrophobic substance (e.g., a hydrophobic polymer) and followed by applying compounds to the coating. The hydrophobic substance may be a matrix which also reacts with active sites on provided compounds (e.g., siloxy based polymers). In some embodiments, compounds may be dispersed within a matrix before applying the matrix to a surface. The matrix may act as a low energy hydrophobic coating which also couples the compounds to the surface after curing the matrix.

In some embodiments, counter ions for a bridged polycyclic compound may be selected to adjust particular properties of a compound or to introduce new properties to the compound. Adjusting properties of a compound based on a selection of a particular counter ion allows further customization of a compound. In some embodiments, counter ions may include counter ions which have or enhance antimicrobial properties and/or anti-inflammatory properties (e.g., boron, zinc). In some embodiment, counter ions may adjust the hydrophilicity or hydrophobicity of the complex. Counter ions may include metals. Research has held that specific counter ions do affect the antimicrobial activity of quaternary ammonium compounds.

Counter ions may include, but are not limited to, organic, inorganic, or organometallic moieties. Examples of counter ions may include inorganic ions (e.g., halogen ions, such as fluorine, bromine, chlorine and iodine), organic ions (e.g., tosylate, prosylate sulfuric acid, nitric acid and phosphoric acid, and ions of organic acids such as succinic acid, fumaric acid, lactic acid, glycolic acid, citric acid, tartaric acid and benzoic acid), or coordinate type anions (e.g., fluoro sulfate and tetrafluoro borate).

In some embodiments, counter ions may include a hydrophobic organic group (e.g., lauryl sulfate, dodecylbenzene sulphonate, diethylhexyl sulphosuccinate, carboxylic acid derivatives with alkane, alkene or alkyne aliphatic tails such as myristic acid salts, octadecanate, dodecanoic acid salts, oleic acid salts, Palmitoleic acid salts, lauric acid salts, Stearic acid salts, phosphinic acid salts, phosphonic acid salts (i.e. tetradecylphosphonate, hexadecylphosphonate) and dodecylsulphonate, dodecylsulfate anions).

Synthesis of Bridged Polycyclic Compounds

For commercialization purposes compounds such as bridged polycyclic compounds (and their metal and/or metal oxide coated counterparts) require an efficient and cost effective method of synthesis. In some embodiments, bridged polycyclic compounds may be formed through the self-assembly of two or more compounds to form much larger complex system in fewer steps and more efficiently than traditional stepwise synthetic means.

At the most general level, the words "self-assembly" are used to identify the phenomenon whereby some kind of higher-level pattern emerges from the interactions of multiple simple components. An example of self-assembly from the Stang group is shown in Scheme 1 (Stang, P. J.; Cao, D. H. *J. Am. Chem. Soc.* 1994, 116, 4981). To set this particular type of self-assembly in its proper context, it should be noted that in the field of chemistry, the term "self-assembly" is used to describe two distinct types of processes. On the one hand, there are assemblies that lead to the formation of essentially infinite arrays, while on the other hand, there are assemblies such as that shown in Scheme 1 that lead to distinct, bounded species. Furthermore, within each of these categories, it is possible to make a further distinction that reflects the scale of organization. For example, for infinite arrays, one may consider processes such as crystallization, where the molecules are ordered at the molecular level (ca. $10^{-9}$ m), or the formation of self-assembled monolayers and bilayers, where there is little order between individual molecules, but a larger scale of organization is evident across say the $10^{-6}$ m level. Likewise, the scale of organization for assemblies leading to distinct species may be broken down into similar categories. It may be noted the self-assembly of macroscale objects ($10^{-3}$ m) is currently being investigated. However, as far as the interaction of molecules to form distinct species goes, it may be considered the formation of micelles and vesicles that constitutes assembly at the $10^{-6}$ m level.

Scheme 1.
A typical strict self-assembly reported by Stang et al.

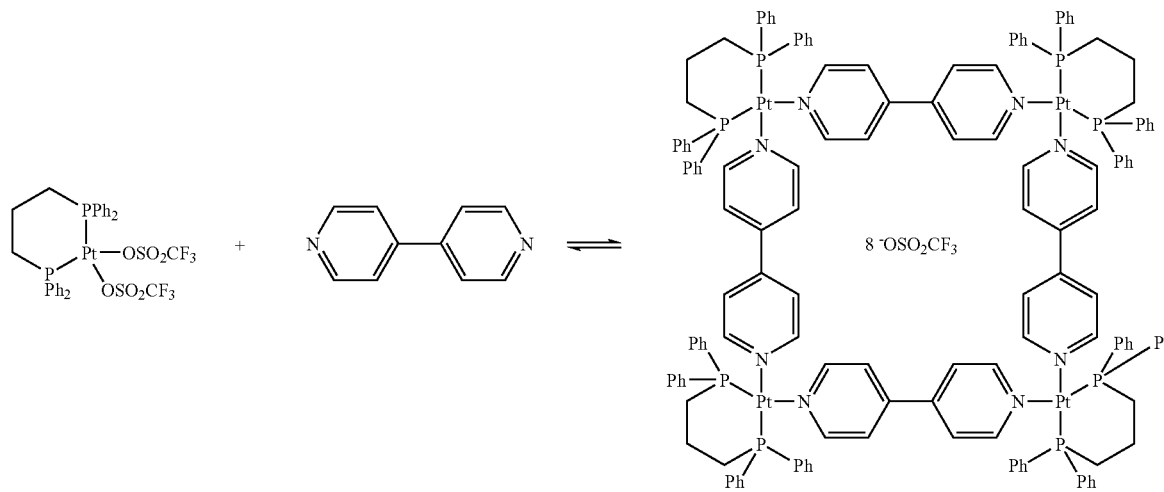

The essential features of chemical assembly processes is that they share a common self-correcting mechanism. In other words, strict self-assemblies are fully reversible, dynamic, systems that lead to a product that represents the global thermodynamic minimum for the system. Sometimes an additive or template is needed to boost the efficiency of the assembly, but this is the only true variable if one is speaking of strict self-assembly. At their cores, strict molecular assemblies consist of subunits, product, and an equilibrium that relates the two.

One addition to the assembly lexicon added a layer of complexity to the above definition. Thus, one of the seven different classes of self-assembly originally proposed by Lindsey—which are strict self-assembly processes (with or without a template) positioned in different chemical settings—is commonly known as "irreversible self-assembly." This term is used to describe two-step processes, whereby a strict self-assembly processes is followed by irreversible reactions that covalently knit together the array of subunits. As Whitesides noted, strictly speaking this term is a misnomer. Hence, along with other types of post-assembly modified self-assemblies, one categorizes these processes as "self-assembly with covalent modification." Postmodification generally comes in the form of a series of covalent bond formation steps and is of less interest to us here. The crux of any self-assembly process is the self-assembly.

Even within the strict confines given above, self-assembly processes come in all shapes and sizes. One of the results of this complexity is that defining self-assembly is difficult. Thus, although definitions from Hamilton, Whitesides, and Lehn were highly influential in clarifying the quality of self-assembly, signs of confusion still appear in the literature. Perhaps part of the problem lies in Kelvin's dictum: if we cannot put a number to it, we do not understand it. Put another way, without a unifying quantitative description of self-assembly, one's appreciation of self-assembly is limited. With the idea of a unifying quantitative description of self-assemblies, Lehn pointed out that one's approach must require a kind of molecular information science, of "molecular informatics." Hence, chemists have, over the last 15 years or so, been busy contributing to this information data bank. As this collection of data increases, it becomes possible to begin to quantify assemblies. This process is, in effect, writing the rule book that will ultimately allow molecular subunits to be readily designed and synthesized for a required self-assembly. A discussion of supramolecular self-assembly using covalent bonds may be found in Bruce C. Gibb "Strict Self-Assembly and Self-Assembly with Covalent Modifications" Encyclopedia of Supramolecular Chemistry 17 Aug. 2004, which is incorporated by reference as if fully set forth herein.

Dynamic covalent chemistry relates to chemical reactions carried out reversibly under conditions of equilibrium control. The reversible nature of the reactions introduces the prospects of "error checking" and "proof-reading" into synthetic processes where dynamic covalent chemistry operates. Since the formation of products occurs under thermodynamic control, product distributions depend only on the relative stabilities of the final products. In kinetically controlled reactions, however, it is the free energy differences between the transition states leading to the products that determines their relative proportions. Supramolecular chemistry has had a huge impact on synthesis at two levels: one is noncovalent synthesis, or strict self-assembly, and the other is supramolecular assistance to molecular synthesis, also referred to as self-assembly followed by covalent modification. Noncovalent synthesis has given us access to finite supermolecules and infinite supramolecular arrays. Supramolecular assistance to covalent synthesis has been exploited in the construction of more-complex systems, such as interlocked molecular compounds (for example, catenanes and rotaxanes) as well as container molecules (molecular capsules). The appealing prospect of also synthesizing these types of compounds with complex molecular architectures using reversible covalent bond forming chemistry has led to the development of dynamic covalent chemistry. Historically, dynamic covalent chemistry has played a central role in the development of conformational analysis by opening up the possibility to be able to equilibrate configurational isomers, sometimes with base (for example, esters) and sometimes with acid (for example, acetals). These stereochemical "balancing acts" revealed another major advantage that dynamic covalent chemistry offers the chemist, which is not so easily accessible in the kinetically controlled regime: the ability to re-adjust the product distribution of a reaction, even once the initial products have been formed, by changing the reaction's environment (for example, concentration, temperature, presence or absence of a template). This highly transparent, yet tremendously subtle, characteristic of dynamic covalent chemistry has led to key discoveries in polymer chemistry. A discussion of supramolecular self-assembly may be found in Rowan, S. J. et al. "Dynamic covalent chemistry" *Angew Chem Int Ed Engl.*, 2002 Mar. 15; 41(6):898-952, which is incorporated by reference as if set forth herein.

In some embodiments, self-assembly techniques (e.g., dynamic covalent chemistry) may be employed to synthesize stable compounds, which are themselves large enough to be described as nanoparticles and/or which may be used to form nanoparticles.

Bridged polycyclic compounds represented by compounds 104 and 108 may be synthesized by any means known to one skilled in the art. As has been mentioned, self-assembly may be a useful technique for efficiently synthesizing nanoparticles described herein. In some embodiments, nanoparticles such as compounds 104 and 108 may be formed via self-assembly using Schiff base condensation reactions between amines and aldehydes to form an imine as depicted in Scheme 3.

Scheme 3.
Schematic depiction of the formation of compound 102.

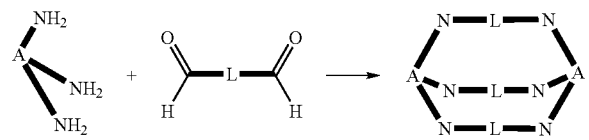

In Scheme 3, the amine depicted is trifunctional and the aldehyde is bifunctional. However, the example depicted in Scheme 3 should not be seen as a limiting embodiment. For example, a Schiff base condensation reaction is depicted in Scheme 4 in which the amine is bifunctional and the aldehyde is trifunctional.

Scheme 4.
Schematic depiction of the formation of compound 102.

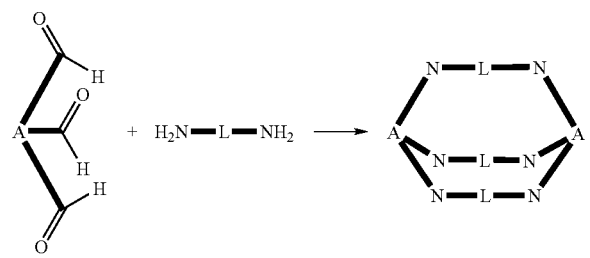

In some embodiments, two different trifunctional molecules may be reacted with one another in order to form an asymmetric adduct. Scheme 4a depicts an embodiment of the formation of an asymmetric adduct.

Scheme 4a.
Schematic depiction of the formation of compound 100c.

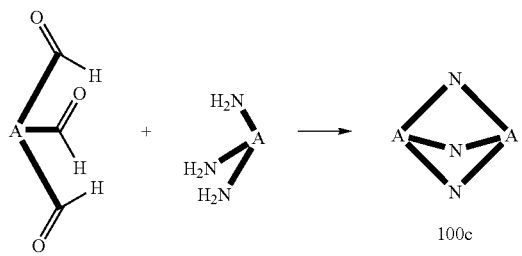

For example, a trifunctional amine (e.g., tris(2-aminoethyl) amine (TREN)) may be reacted with a trifunctional aldehyde (e.g., 1,3,5-aldehyde substituted phenyl). Triethanolamine may be functionalized at the OH with an aminoacid to give N—(CH$_2$CH$_2$OC(O)Phenyl(CHO). N—(CH$_2$CH$_2$OC(O) Phenyl(CHO) may be reacted with any triamine to give an asymmetric example of a bridged polycyclic compound. A discussion of synthesis techniques for different multifunctional ligands (e.g., trifunctional aldehydes) may be found in Chand et al. "Synthesis of a Heteroditopic Cryptand Capable of Imposing a Distorted Coordination Geometry onto Cu(II): Crystal Structures of the Cryptand (L), [Cu(L)(CN)](picrate), and [Cu(L)(NCS)] {picrate) and Spectroscopic Studies of the Cu(II) Complexes" Inorg Chem 1996, 35, 3380-3387, which is incorporated by reference as if fully set forth herein.

In some embodiments, formation of a bridged polycyclic compound (e.g., Schemes 4, 4a, or 5) may be carried out in an alcohol (e.g., ethanol).

A more specific example of the self-assembly Schiff base condensation strategy depicted in Scheme 3 is depicted in Scheme 5 showing the formation of imine compound 116. Imine compound 116 may be used as an intermediate toward the formation of compound 110.

Scheme 5.
Schematic depiction of the formation of compound 116.

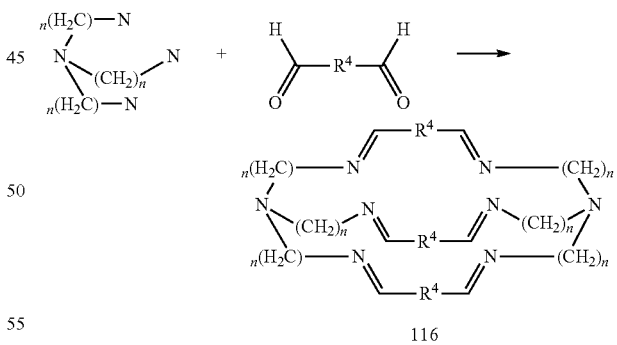

A Schiff base condensation may be carried out using an acid catalyst (e.g., acetic acid). A Schiff base condensation may be carried out using any means known to one skilled in the art. Techniques for amine aldehyde condensations may be found in U.S. Patent Application, Publication No. 2004/0267009 to Redko et al. ("Redko"), which is incorporated by reference as if fully set forth herein.

Other examples of Schiff base condensations may include reactions such as those depicted in Scheme 5a. Scheme 5a depicts a substituted amine condensing with an aldehyde.

Scheme 5a.
Schematic depiction of the formation of compound 116a.

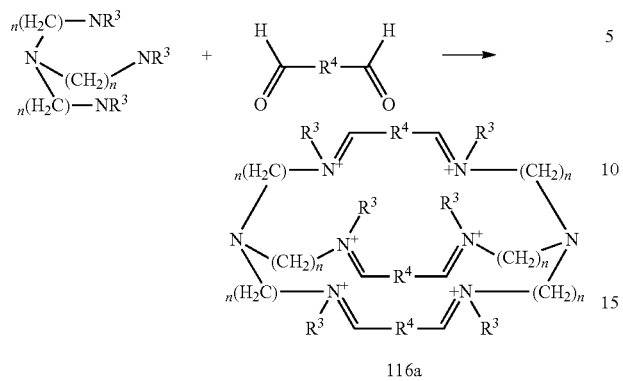

116a

In some embodiments, a template may be used to facilitate the formation of compounds such as 118. A template may include a metal template. A metal template may include any metal cation. A template may assist in preorganizing one or more reagents in a Schiff base condensation such that labile reagents are properly oriented to form a bridged polycyclic compound as opposed to an oligomer, facilitating the reaction. Scheme 6 depicts a schematic representation of the formation of a compound 118 using such a strategy.

Scheme 6.
Schematic depiction of the formation of compound 118 using a metal template.

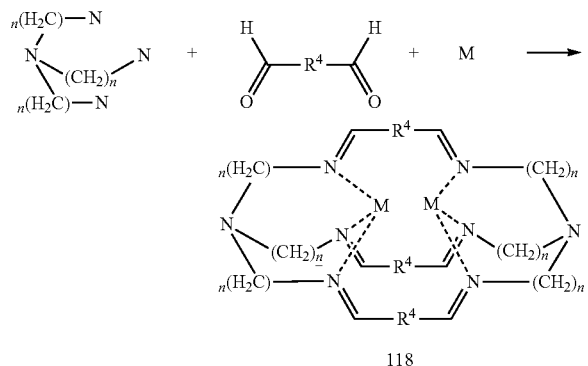

118

In some embodiments, compound 118 may be used as an intermediate toward the formation of a bridged polycyclic compound (e.g., compound 110). Techniques for template facilitated synthesis of molecules may be found in Drew et al., "$d^{10}$ Cations within triple-helical cryptand hosts; a structural and modeling study" *J. Chem. Soc., Dalton Trans.*, 2000, 1513-1519, which is incorporated by reference as if fully set forth herein.

When a metal template is used in the formation of a bridged polycyclic compound (e.g., compound 118), the template may be carried through the rest of the synthesis. In some embodiments, a metal template may be replaced in a later transmetallation step. It may be more efficient to consider all of the properties of the metal template so that a transmetallation step is not necessary at a later time. Not only may a metal's templating ability for a condensation reaction be considered but whether or not the metal also has antimicrobial or anti-inflammation properties.

Schiff base condensation chemistry should not be viewed as a limiting example of a method for forming bridged polycyclic compounds as described herein. There exist many other methods of forming bridged polycyclic compounds as described herein. Other types of condensation reactions are known. Scheme 6a depicts an embodiment of a condensation reaction which may be used to form a bridged polycyclic compound (e.g., compound 118a).

Scheme 6a.
Schematic depiction of the formation of compound 118a.

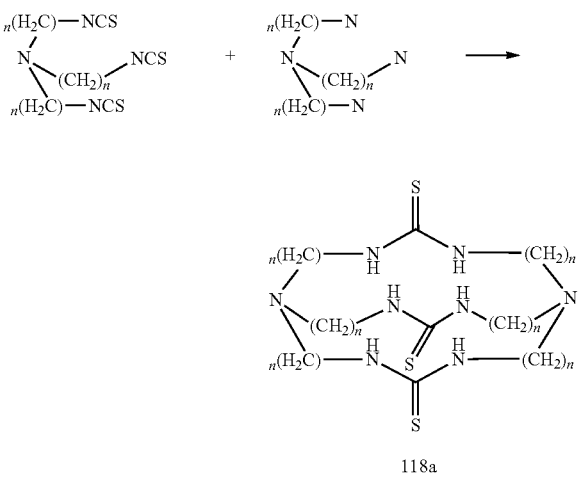

118a

Techniques for the synthesis of molecules using condensation reactions as generally depicted in Scheme 6a may be found in Xiao-an Zhang, "From Supramolecular Vanadate Receptors to Enzyme Models of Vanadium Haloperoxidase" *Philosophisch-Naturwissenschaftlichen Fakultät der Universität Basel*, 2005, which is incorporated by reference as if fully set forth herein. Compound 118a may be further reduced to the thiol (e.g., thioether, including peptides and/or peptide mimics and/or aziridines), alkylated, metalated, and/or used as a core for a core-shell compound.

In some embodiments, imine compounds (e.g., 7 and 8) may be reduced to an amine (e.g., a secondary amine). Schemes 7 and 8 depict representations of the reductions of two different imine compounds to their respective amines. Schemes 7 and 8 depict the reduction of all imines in compounds 116 and 118, however in some instances this may not be desirable and only some of the imines may be reduced to preserve at least some of the imine functional groups for later exploitation.

Scheme 7.
Schematic depiction of the formation of compound 120.

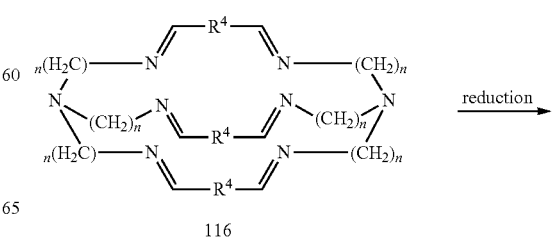

116

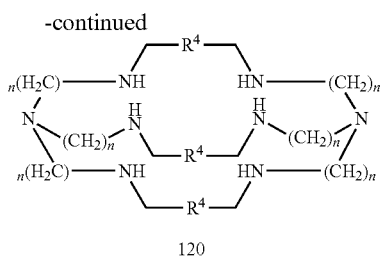

120

Scheme 8.
Schematic depiction of the formation of compound 122.

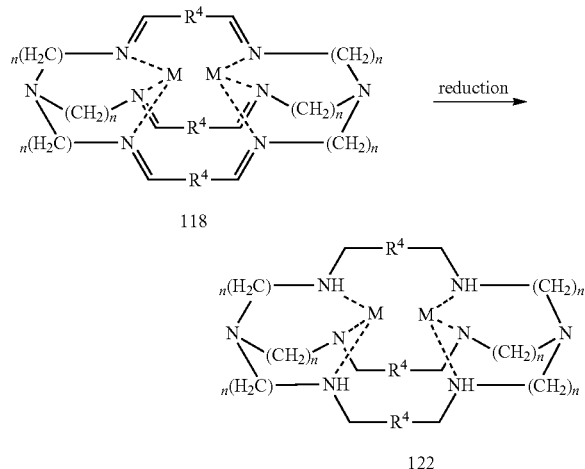

Reduction techniques are well known to one skilled in the art, and there are many reductions techniques known to one skilled in the art which may be applied. Some common reductive reagents include, but are not limited to, $LiAlH_4$, $NaBH_4$, $H_2$, or polymethylhydrosiloxane (PMHS). Some compounds such as PMHS may be used with a lewis acid (e.g., $B(C_6H_5)_3$, $ZnCl_2$, $BF_3$, $AlCl_3$, Zn-diamine, $Ti(O^iPr)_4$, $IrCl[COD]_2$, $IrCl[COE]_2$, $RhCl[COD]_2$, $IrCl_3$, $Ti(OR)_4$, $Ti(CO_2OR)_4$, $Ti(ester)_4$, $Ti(amine)_4$, $CuI$, $Cu(OAc)_2$, etc.). Methods for using PMHS as a reducing agent may be found in Lawrence et al., "Polymethylhydrosiloxane: a versatile reducing agent for organic synthesis" *J. Chem. Soc., Perkin Trans.* 1, 1999, 3381-3391, which is incorporated by reference as if fully set forth herein.

In some embodiments, a reduction may be carried out in an alcohol (e.g., ethanol) with with a reducing agent (e.g., sodium borohydride).

In some embodiments, coupling of corner units or corner units and linker units to form bridged polycyclic imine compounds may be carried out in an alcohol (e.g., ethanol) based solvent. In some embodiments, reduction of at least some of the imines may be carried out without any substantial work up directly following the coupling step (e.g., by adding a reducing agent such as sodium borohydride) to form a bridged polycyclic compound.

In the past reactions such as the coupling and reduction steps have been carried out as two totally separate steps involving for example working up (e.g., purifying and isolating) the reaction after the coupling step before the reducing step. One or more of these steps (e.g., the coupling step) have in the past been carried out in for example acetonitrile resulting in a seemingly polymeric substance, followed by an isoxolate extraction. In reality the isoxolate extraction may have been merely driving the reaction towards the bridged polyclic product, by conversion of polymer and oligomer products.

Running the reactions in a solution of heated ethanol results in almost quantitative yields of the desired product without any substantial work up or isolation protocols.

In some embodiments, coupling of corner units or corner units and linker units to form bridged polycyclic imine compounds may be carried out in a green solvent. In some embodiments, a green solvent may include any solvent which is naturally occurring and which has been found not to harm the environment when used on an industrial scale. In some embodiments, a green solvent may include water or an alcohol based solvent (e.g., ethanol). A catalyst may be used to run the reaction in water. In some embodiments a catalyst may include aniline. A similar method is described in Angewante Chemie Vol. 45, pages 75-81, which is incorporated by reference as if fully set forth herein.

In some embodiments, certain industrial wastes may be used as a hydride source for reducing an imine to an amine. Using an industrial waste may have several advantages. Using industrial wastes as reactive reagents may be environmentally friendly due to the recycling of waste which must normally be disposed. Industrial wastes are normally very inexpensive, if not free, and sometimes companies will pay for them to be removed. Some industrial wastes may be used as a matrix for the bridged polycyclic compounds facilitating application of the bridged polycyclic compounds to surfaces.

In some embodiments, one or more amines of a bridged polycyclic compound may transformed into the corresponding ammonium salt. A precursor of a substituent $R^3$ may be reacted with an amine of a bridged polycyclic compound forming quaternary ammonium salts. In some embodiments, X of a precursor may include a halogen (e.g., alkyl bromide). A base, more specifically a weak base, may be used in combination with for example an alkyl bromide. A portion of a precursor of a substituent $R^3$ may act as a counter ion X. A nonlimiting example may include reacting compound 120 with bromohexane in the presence of a base (e.g., triethylamine) forming an amine alkylated with the hexyl and the resulting bromine ion acts as at least one of the counter ions X to compound 124. It is to be understood that counter ions may be exchanged at a later point in a synthetic sequence to a more desirable counter ion (e.g., a counter ion that can demonstrate increased antimicrobial properties compared to other halide counterions) using methods known to one skilled in the art. A counterion of this type is tetrafluoroborate. Tetrafluoroborate can be readily exchanged for iodide by adding potassium tetrafluoroborate to a solution of an iodide salt in common solvents known to those skilled in the art as described by A.D. Headley, et. al. in *J. Org. Chem.* 2006, ASAP received Jun. 27, 2006, which is incorporated by reference as if fully set forth herein. Ion exchange is a common technique and can also be found in D. F. Bocian *Inorg. Chem.* 1998, 37, 1191-1201 and S. T. Diver *J. Org. Chem.* 2002, 67, 1708-1711, which is incorporated by reference as if fully set forth herein. Schemes 9 and 10 depict the formation of quaternary ammonium salt compounds 124 and 126.

Scheme 9.
Schematic depiction of the formation of compound 124.

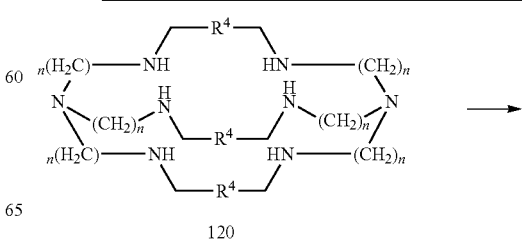

120

-continued

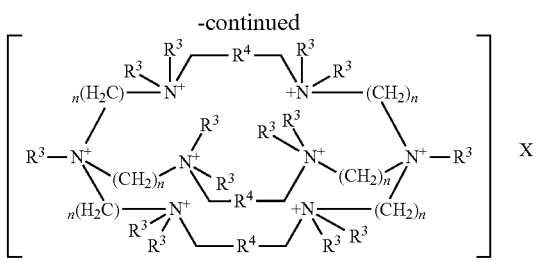

124

Scheme 10.
Schematic depiction of the formation of compound 126.

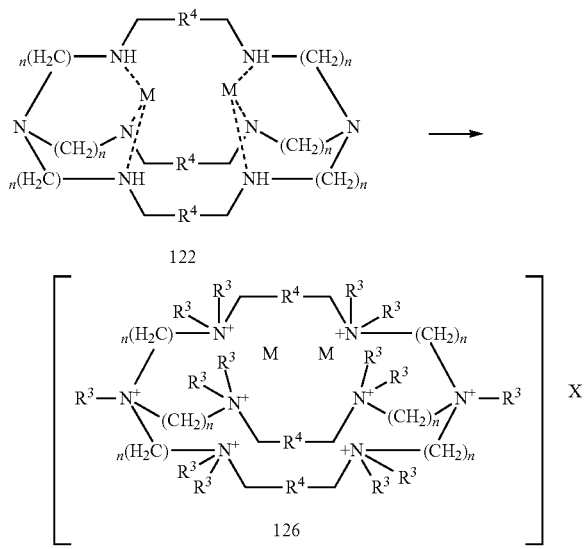

Common techniques for functionalizing amines may be found in a review by Salvatore et al., "Synthesis of secondary amines" *Tetrahedron* 57, 2001, 7785-7811, which is incorporated by reference as if fully set forth herein.

In some embodiments, an amine may be functionalized (e.g., compound 122) by reacting with an epoxide. For example, reacting compound 122 with an epoxide may result in an epoxide ring opening and thus a free alcohol coupled to at least some of the amines in compound 122. The resulting free alcohol may be reacted with $(OR)_3Si(CH_2)_nN^+R_3$ resulting from the attack of the N on the epoxide containing carbon. This may result in an ammonium on the bridged polycyclic compound and an ammonium pendant arm. Free amines of the herein described bridged polycyclic compounds may be reacted with a di-epoxide crosslinker (e.g., 1,2,7,8-diepoxyoctane or epoxypropyl terminated polydimethylsiloxane), followed by $(OR)_3Si(CH_2)_nN^+R_3$ to functionalize the crosslinked mixture. Reaction with a vinyl epoxide may result in a light crosslink terminus and an alcohol (e.g., with which a silane may be reacted). A free amine of a bridged polycyclic compound described herein may be modified by an epoxy alkane (or glycidyl ether (e.g., hexyl, octyl or decyl glycidyl ether)), followed by further modification by a variety of alkoxysilanes with desired functional groups (e.g., an alkyl ammonium salt attached to the Si). One may modify a free amine with alkyl anhydrides (e.g., 2-octen-1-ylsuccinic anhydride).

In another example of functionalizing an amine at least in part defining a bridged polycyclic compound, a functionalized substituent may be coupled to the amine. A functionalized substituent may include an alkyl amine group. A non-limiting example of an alkyl amine may include —$CH_2CH_2CH_2NH(CH_2)_5CH_3$. The amine may be further functionalized. For example the amine of the alkyl amine may be alklyated such that another quaternary amine is available increasing the antimicrobial activity of the bridged polycyclic compound. The synthesis of such an embodiment is detailed in the Examples section.

As mentioned previously, it is widely held that self-cleaning surfaces are a combination of low surface-energy species and a peculiar topographic feature based on dual-size roughness: the coarse-scale rough structure is about 10-20 μm, whereas the finer structure on top of the coarse structure is in the range of 100 nm to 1 μm. The dual-size structure has proven to be vital in generating the superhydrophobicity of the lotus leaves, especially for obtaining low water rolloff angles. In some embodiments, free amines of a bridged polycyclic compound as described herein may be mixed with an oxide bridged polycyclic compound (e.g., $TiO_2$ or $SiO_2$), followed by a di-epoxide linker (e.g., 1,2,7,8-diepoxyoctane or epoxypropyl terminated polydimethylsiloxane) and a photo activated crosslink (e.g., N-vinyl-2-pyrrolidinone). A discussion of the reaction of epoxides, oxides, amines, etc. may be found in Trentler et al., "Epoxy Resin-Photopolymer Composites for Volume Holography" *Chem. Mater.* 2000, 12, 1431-1438, which is incorporated by reference as if fully set forth herein. There are many methods for cross-linking bridged polycyclic compounds which may also lead to the desired topography necessary for superhydrophobicity, including crosslinking oxide bridged polycyclic compounds with silsesquioxanes. A discussion of the reaction of epoxides (e.g., vinyl epoxides), silsesquioxanes, etc. may be found in Huang et al., "Thermomechanical properties of polyimide-epoxy nanocomposites from cubic silsesquioxane epoxides" *J. Mater. Chem.* 2004, 14, 2858-2863, which is incorporated by reference as if fully set forth herein. General techniques (e.g., using Michael-type additions) for functionalizing/modifying the surface of particles (which may be applied to bridged polycyclic compounds as described herein) may be found in U.S. Pat. No. 6,887,517 to Cook et al. ("Cook"), which is incorporated by reference as if fully set forth herein.

In some embodiments, one or more amines of a bridged polycyclic compound may be functionalized in more than one step. For example, several secondary amines forming a bridged polycyclic compound may be transformed into tertiary amines, followed by subsequent transformation into a quaternary amine. Such synthetic flexibility allows customization of the amines such that different functional groups may be coupled to the same amine. Depending on the reactions conditions required to couple the different functional groups to the amine, the reactions may be run sequentially without any purification steps between coupling different functional groups to the amine. Scheme 11 depicts a generic representation of a two step functionalization sequence of the secondary amines of compound 120 to form the quaternary ammonium salts of compound 128. In the first step bromohexane and a nonnucleophilic base (e.g., triethylamine) are added to the reaction mixture, followed by the addition of methyliodide and more triethylamine to form compound 128 such that several of the quaternary amrnmonium salts include two different functional groups. The ability to customize the functional groups attached to the quaternary ammonium salt is important at least in that the functional groups attached to a quaternary ammonium salt may effect the antimicrobial properties of the salt. Customization of functional groups attached to bridged polycyclic compounds, and amines specifically, may allow coupling of functional groups with different functionalities (e.g., groups which function to cross-couple bridged polycyclic compounds to one another or to a surface.

Scheme 11.
Schematic depiction of the formation of compound 126.

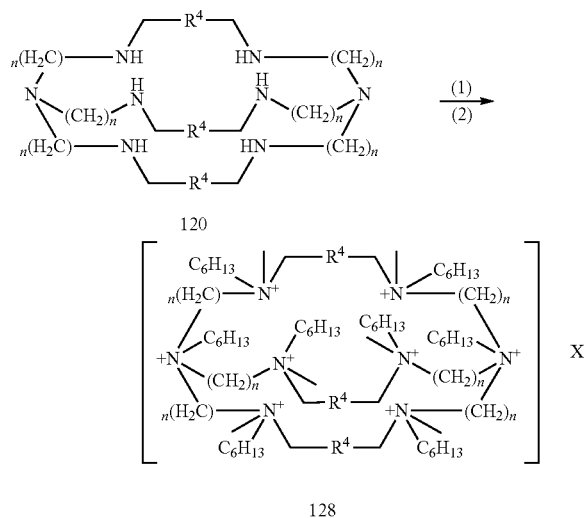

Metal Oxide Coatings of Bridged polycyclic Compounds

Nanocrystals of transition metal oxides have attracted a great deal of attention from researchers in various fields due to their numerous technological applications. Among them, titanja ($TiO_2$) nanocrystals have been the most intensively studied owing to their versatile applications, which include solar cells, photocatalysts, and photochromic devices. Many synthetic methods have been reported for the preparation of $TiO_2$ nanocrystals, including sol-gel reactions, hydrotherrnal reactions, nonhydrolytic sol-gel reactions, template methods, and reactions in reverse micelles. $TiO_2$ nanocrystals with various morphologies and shapes, such as nanorods, nanotubes, nanowires, and nanospheres may be produced depending on the synthetic method used.

Due to the high reactivity of titanium precursors such as $TiCl_4$ and titanium alkoxides, the control of the reaction rate is a key factor in obtaining $TiO_2$ nanocrystals with the desired crystalline structure and/or shapes. Chemseddine and co-workers have reported the synthesis of uniform-sized $TiO_2$ nanocrystals whose shapes varied depending on the ratio of $Me_4NOH$ to titanium alkoxide. However, the synthesis was performed at a very low concentration and produced only a small quantity of the nanocrystals. Weller and co-workers have reported the controlled growth of $TiO_2$ nanocrystals by modulation of the hydrolysis rate, using oleic acid as a stabilizing surfactant at 80° C., and Jun et al. have reported the surfactant-mediated shape evolution of anatase nanocrystals in nonaqueous media at 300° C. Techniques for low temperature synthesis of metal oxide and metal oxide shells may be found in Han et al., "Low-Temperature Synthesis of Highly Crystalline $TiO_2$ Nanocrystals and their Application to Photocatalysis" *Small*, 1, No. 8-9, 812-816, and Imihof et. al. "Preparation and Characterization of Titania-Coated Polystyrene Spheres and Hollow Titania Shells" *Langmuir*, 17, 3579-3585, which are incorporated by reference as if fuilly set forth herein.

Additionally Core-shell metal nanoparticles is an emerging and active area of contemporary science. While most of the research in this area has been on noble-metal nanocores and molecular shells, there has been a slow and steady growth of activity on nanomaterials with chalcogenide shells. Monolayers anchored onto metal cores have been used as precursors to make oxide shells. An approach in this direction has been used to make silica-coated gold clusters. Similar method have been used in the synthesis of $ZrO_2$-covered nanoparticles of silver. In all these methodologies, the monolayer cover is important, as the chemistry is specific to the shell. Previous monolayer routes to oxide-shell materials are rather involved and requires multistep processes, and scale-up is difficult. More recently a one step method was developed using the well-known reduction of noble metals with dimethylformamide (DMF) in the presence of oxide-forming precursors used by Liz-Marzan et al. for the synthesis of Ag@$TiO_2$. Using this method $TiO_2$- and $ZrO_2$-covered Au and Ag redissolvable particles were synthesized. Work was initiated on oxide-protected metal colloids because this is one way to make metal nanoparticles stable under extreme conditions. Recent work on optical nonlinearity has shown that these materials are some of the best optical limiters known thus far. However, at high light intensities, they are susceptible to damage, leading to photofragmentation, ligand desorption, etc. To make them stable at extreme conditions, it is necessary to protect them with stable and chemically inert shells such as oxides. Oxide-protected colloids were irradiated with laser pulses of intensities up to 2.8GW/$cm_2$, and no sign of laser-induced damage was observed. This kind of cover also makes it possible to fabricate/process materials in the form of thin films and disks for applications. Particles with oxide shells are interesting from other perspectives as well. The catalytic properties of the oxide surfaces, modified with the metal core, especially photocatalysis, are an important aspect. The shells being porous at low thickness makes it possible for ions and molecules to diffuse through them. Apart from implications in catalysis, this also leads to changes in the dielectric constant, which results in changes in color. Modified properties such as electrical transport upon exposure to gases and ions are another important aspect. The shell being inert may be used to deliver metal colloids into reactive environments and may even be thought of as a mode to deliver drugs. From all these perspectives, it is interesting and possibly desirable to make core-shell particles with oxide covers by simple and scalable procedures. Techniques for synthesizing metal oxide shells may be found in Tom et al., "Freely Dispersible Au@$TiO2$, Au@$ZrO2$, Ag@$TiO2$, and Ag@$ZrO2$ Core-Shell Nanoparticles: One-Step Synthesis, Characterization, Spectroscopy, and Optical Limiting Properties" *Langmuir* 2003, 19, 3439-3445, which is incorporated by reference as if fully set forth herein.

Coating of colloidal particles with a layer of a different material is used as a means to modify their surface chemical, reactive, catalytic, optical, or magnetic properties. Such core-shell particles may often be prepared by controlled precipitation of inorganic precursors onto the core particles, in some cases assisted by a coupling agent as with the combination silica and gold or silver as described above. A second approach is to deposit small particles of the coating material on the cores by heterocoagulation, such as in the case of yttrium basic carbonate or zirconia on polystyrene.

An especially versatile example of the second approach is the layer-by-layer technique, in which successive layers of anionic particles are deposited, alternated by layers of a cationic polymer. The layer-by-layer technique has the great advantage that it is not very specific for the coating material, where other methods usually depend on the particular combination of core and shell material. Disadvantages are that the layers are added in discrete steps of about 30 nm and that a lot of redundant polymer is also incorporated in the shell. Hollow particles form a special kind of core-shell particle in which the core consists of air or solvent. Hollow inorganic particles are made by removal of the core with a solvent or by heating (calcination). Removal of polystyrene cores by calcination has been used to make hollow spheres of yttrium compounds, zirconia, and silica. Hollow silica particles have been made by dissolution of silver and gold or zinc sulfide. Colloidal crystals of particles with a low-index core and a high-index shell such as titania are suitable building blocks for photonic crystals, provided that they may be made monodisperse with a smooth coating.

Particles coated with titania are generally exceptionally difficult to synthesize because the titania precursors are highly reactive, making it difficult to control their precipitation. This easily causes the core particles to aggregate or the titania to form separate particles. Titania coated particles are very useful as catalysts and as white pigments. Titanyl sulfate in sulfuric acid was used to deposit titania on silica spheres. Rather irregular coatings were obtained. The slightly low isoelectric point indicated that the coverage was incomplete. This was also found to be the case by using $TiCl_4$ to coat silica. Other methods use the hydrolysis of titanium alkoxides in nonaqueous solvents as the precursor. Only a monolayer of titania was deposited on silica spheres in tetrahydrofuran. Using a similar approach, thicker coatings may be deposited on copper compounds, zinc oxide, silica, and gold nanoparticles. These methods lead to particles with a complete coating but with a lot of surface roughness. They also take place at a rather low concentration of the alkoxide, typically around 0.01 M. This concentration needs to be well controlled because too high concentrations easily lead to particle aggregation or formation of secondary titania particles. This is why multiple steps are often used to obtain thicker coatings.

Stable colloidal core-shell particles consisting of a polystyrene core and a titania coating were prepared in one step by the hydrolysis of a titanium alkoxide in the presence of a cationic polystyrene latex. Although Imhof used polystyrene as a core, other polymer colloids may be given cationic surface groups or negatively charged particles may be made positive by coating with a polyelectrolyte. The coatings are very smooth and uniform and may be varied in thickness from just a few nanometers to at least 50 nm. Thicker coatings should also be possible but only through a multistep seeded growth process. The coated spheres have the same monodispersity as the starting latex, allowing them to form colloidal crystals.

Measurement of the coating thickness with light scattering and electron microscopy showed that the titania coating is not dense when the particles are in suspension in ethanol but that it densifies when the particles are dried. From the ratio of titania to polystyrene, measured by thermogravimetric analysis, it was found that the coating consists of 21 vol % titania and that drying increases this to 55 vol %. In the process, the shells become much thinner.

Hollow titania particles may be made by removal of the polystyrene cores either by dissolution in toluene or by firing in a furnace. The dissolution route leaves stable colloidal titania shells that are spherical and monodisperse. Drying of these shells causes them to deform because of their softness. The firing route produces dense, undeformed shells of a mosaic of small anatase crystallites. Techniques for synthesis of metal oxide shells may be found in Han et al., "Low-Temperature Synthesis of Highly Crystalline $TiO_2$ Nanocrystals and their Application to Photocatalysis" *Small*, 1, No. 8-9, 812-816, which is incorporated by reference as if fully set forth herein.

The antimicrobial effects of titanium dioxide have been known for quite some time and it is used to control bacteria activity. When titanium dioxide ($TiO_2$) is irradiated with near-UV light, this semiconductor exhibits strong bactericidal activity. In some embodiments, cationic bridged polycyclic compounds described herein may be used as the cationic core of a core-shell particle. The shell may be formed form negatively charged metal oxides deposited on the surface of the positively charged core bridged polycyclic compound. By combining metal oxides (e.g., $TiO_2$) with positively charged bridged polycyclic compounds containing quaternary ammonium salts, one is able to combine the properties of both substances (e.g., different mechanisms of antimicrobial attack within one bridged polycyclic compound leading to a more effective antimicrobial).

In some embodiments, a positively charged or neutral bridged polycyclic compound core may be coated with any metal and/or metal oxide. An oxide precursor of the metal oxide coating may be used to deposit the metal oxide shell around the bridged polycyclic compound core. An oxide precursor may include, but is not limited to, a metal halogenate (e.g., $TiCl_4$) or a metal alkoxide (e.g., titanium tetraisopropoxide (TTIP)). A metal alkoxide may be more stable. In some embodiments, any metal precursor may be used to coat a charged bridged polycyclic compound core with an oxide shell.

In some embodiments, any metal and/or metal precursor may be used to coat a bridged polycyclic compound core. For example, silver may be coupled to the exterior of a bridged polycyclic compound (e.g., silver may coat a portion and/or substantially all of the exterior of the bridged polycyclic compound). In some embodiments, a metal oxide shell may be formed/deposited around a bridged polycyclic compound core and/or a bridged polycyclic compound core including a metal (e.g., silver) coating.

Metals which may be deposited on a charged or neutral core include, but are not limited to Ti, Zr, Hf, B, Zn, Ta, W, V, or combinations thereof (e.g., TiOZrO, borotitanate, etc.). Examples such as these are also biologically active and may contribute to the antimicrobial and/or anti-inflammatory nature of the core-shell bridged polycyclic compounds created. Shell oxides may contribute to a core-shell bridged polycyclic compounds self-cleaning properties.

In some embodiments, metal oxide bridged polycyclic compounds and/or metal oxide core-shell bridged polycyclic compounds may be formed from main group metals, transition group metals, or lanthanide metals. Main group metals may include, but are not limited to, aluminum, gallium, germanium, indium, tin, antimony, lead, and bismuth.

Transition metals may include, but are not limited to, titanium, vanadium, chromium, manganese, iron, cobalt, nickel, copper, zinc, yttrium, zirconium, niobium, molybdenum, ruthenium, rhodium, cadmium, hafnium, tantalum, tungsten, rhenium, osmium, and iridium.

Lanthanide metals may include, but are not limited to, lanthanum, cerium, praseodymium, neodymium, samarium, europium, gadolinium, terbium, dysprosium, holmium, erbium, thulium, ytterbium, and lutetium.

In some embodiments, alkaline earth metals (e.g., calcium, strontium, and barium) may generally be one metal component in mixed metal oxides (e.g., calcium titanate, calcium ruthenate, barium titanate, barium ruthenate, strontium titanate, strontium ruthenate, yttrium barium copper oxide). Simple oxides such as MgO and SrO may be prepared by this method.

In some embodiments, alkali metals (e.g., lithium and potassium) may generally be one metal component in mixed metal oxides (e.g., lithium tantalate ($LiTaO_3$), lithium niobate ($LiNbO_3$), Fe- or Ti-doped lithium niobate, potassium barium niobate ($KBa_2Nb_5O_{15}$), potassium lithium niobate ($K_3Li_2Nb_5O_{15}$), potassium sodium tantalate (($K_{1-x}Na_x$)$TaO_3$), $K_3Li_2(Ta_xNb_{1-x})_5O_{15}$ etc.).

In some embodiments, a metal M may include $CaBi_2O_4$. $CaBi_2O_4$ is an antimicrobial substance activated by natural light, providing another customization avenue, as opposed to titanium oxides which are antimicrobial upon activation by ultraviolet light.

The composition, e.g., solution, used for the deposition includes the soluble polymer and the metal precursors. Metals may be included through addition of appropriate metal salts. For example, barium may be added through a barium salt such as barium acetate. Suitable metal salts may include metal nitrates, metal oxalates, metal acrylates, and metal coordination complexes.

Titanium oxides have been mentioned several times due to their well documented properties (e.g., antimicrobial) as well as the fact that titanium is inexpensive when compared to other metals. However, there are many other metals which may be used and/or combinations of metals which may provide added advantages not observed using any one metal by itself.

In some embodiments, combinations of metals may be used to form a mixed metal oxide shell around a bridged polycyclic compound core. In some embodiments, metal oxide films may include, but are not limited to, a metal oxide with a single metal, may be a metal oxide with two metals or three metals or may be a metal oxide including four or more metals. Mixed oxides have been widely used in catalysis, because the properties of the individual oxides may be modified by the presence of neighboring phases. Mixed oxides improve the activity and selectivity of catalysts by means of the formation of surface defects that may give rise to the formation of acid or basic sites. In semiconductors mixed oxides have important role in modifying the electrical or optical properties of the isolated oxides. Usually zirconia and titania are mixed by solid state reaction, requiring temperatures as high as 2000° C. to form the crystalline $ZrTiO_4$. Mixed metal oxides may include, but are not limited to, barium titanium oxide (barium titanate), strontium titanium oxide (strontium titanate), barium strontium titanium oxide (barium strontium titanate), strontium ruthenium oxide (strontium ruthenate), lanthanum-strontium manganese oxide, yttrium-barium-copper oxide ($YBa_2Cu_3O_7$), vanadium-barium-titanate, etc. The antimicrobial coatings prepared by the present process may be insulating, resistive, conductive, ferroelectric, ferromagnetic, piezoelectric, and even superconductive depending upon the chemical compositions and micro structures.

Gomez et al. reported the synthesis of sol-gel catalysts, where the precursors of the sol-gel catalysts were titanium n-butoxide (98%, Aldrich) and zirconium n-butoxide (99%, Aldrich), with n-butanol (Baker, 99%) as solvent. Samples were prepared by mixing 3.3 moles of $H_2O$ and 3.0 moles of n-butanol at 0° C. under constant stirring. After adjusting the pH at 3 with $HNO_3$, titanium and zirconium n-butoxide were added drop-by-drop to the initial solution for five hours, appropriated amounts of the corresponding alkoxides were used to obtain 100, 90 50, 10 and 0 wt % of $TiO_2$ in $ZrO_2$. The resulting suspensions were maintained under reflux and constant stirring until gelling. Samples were then dried at 70° C. for 24 hours (fresh samples) and calcined at 600 for 4 h. The 2,4-dinitroaniline photodecomposition was determined at room temperature. The evolution of the 2,4-dinitroaniline decomposition in function of time was followed with a UVV is spectrometer at fixed absorption band of 346 nm.

When the diffraction patterns of the pure titania samples are compared with those of the samples containing 10 wt % $ZrO_2$, no phase associated with pure zirconia was observed, only anatase and rutile were identified. This means that the 10 wt % of $ZrO_2$ was dissolved in these two titania polymorphs. The incorporation of zirconium atoms into anatase stabilized the crystalline anatase structure (99 wt %). An additional effect of zirconium atoms is to reduce the crystallite size of both anatase (50 to 13 nm) and rutile phases (90 to 49 nm). The sample with 50:50 wt % amounts of titania and zirconia shows amorphous and crystalline $ZrTiO_4$ phase with mean crystallite size of 1.1 and 36 nm respectively. The crystalline $ZrTiO_4$ phase corresponds to the only intermediate compound reported for this system, Gomez et al.'s results show that the non-hydrolytic synthesis method is not a condition to obtain the compound without previous segregation of tinania or zirconia as reported elsewhere. The samples of pure zirconia and that with 10 wt % titania were amorphous after synthesis. The unmixed ZrO crystallized 48 wt % into the tetragonal phase and the 52 wt % into the monoclinic phase. In the rich $ZrO_2$ mixed oxide only tetragonal and moclinic zirconia may be observed, hence titania was dissolved in the tetragonal and monoclinic phases of zirconia. The crystallite size of the tetragonal phase in the 10 wt % $TiO_2$ sample is 15 nm and is of the same order to that corresponding to the phase obtained in unmixed zirconia (13 nm). This result indicates that titania inhibits crystallite growing; this is also valid for the monoclinic phase. This result contrasts with the observed effect of zirconia into the crystallization of the titania polymorphs diminishing the $TiO_2$ crystallite size. Gomez et al. then assumed that $ZrTiO_4$ is a semiconductor, which generates important hole-electron mobility between the conduction band and the valence band improving the photoactivity. Techniques for synthesis of mixed metal oxide shells may be found in Gomez et al., "Synthesis, characterization and photocativity of nanosized sol-gel $TiO_2$—$ZrO_2$ mixed oxides." *The* 13*th International Congress on Catalysis*, Jul. 10-15, 2004, Paris, France, which is incorporated by reference as if fully set forth herein.

In some embodiments, stabilizers may be before/during/after coating a charged bridged polycyclic compound with a metal oxide. Stabilizers may be added before/during the reaction to ensure the formation of a smooth coating and to prevent the formation of secondary titania particles. After the reaction is complete any or excess stabilizers may be removed. Stabilizers may also be chosen to customize the solubility of the oxide-coated bridged polycyclic compounds. Hydrophilic stabilizers (e.g., polyethylene glycol (PEG), PEG derivatives) may be chosen to increase the water solubility of the new core-shell bridged polycyclic compound. Hydrophobic stabilizers may be used to increase the solubility of the core-shell bridged polycyclic compound in hydrophobic solvents. This may be necessary depending upon the desired properties of the core-shell bridged polycyclic compound. The shell may be so thick that substituents (e.g., $R^3$) on the surface of a bridged polycyclic compound core may not be able to effect the properties of the core-shell bridged polycyclic compound, thus increasing the need for functional stabilizer substituents coupled to the surface of the core-shell bridged polycyclic compound.

In some embodiments, stabilizers may be used simply to ensure the uniformity of coating of the shell over the core. After completion of the reaction the stabilizers may be removed upon work-up (e.g., purification) of the core-shell bridged polycyclic compounds.

By modifying the conditions of the reaction during the formation of the shell around the core bridged polycyclic compound, many of the properties (e.g., uniformity and thickness) of the shell may be controlled. Metal oxide shells are known to be porous at low thickness. The shells being porous at low thickness makes it possible for ions and molecules to diffuse through them. Contact of a microbe cell wall and a core-shell bridged polycyclic compound may cause part of the microbe cell wall to open and diffuse into the bridged polycyclic compound, depending upon the specific properties of the shell. In this way core-shell bridged polycyclic compounds may be customized to expose microbes to two or more types of compounds with antimicrobial properties. Preparing antimicrobials including two or more antimicrobial functionalities may increase the effective killing power of the core-shell bridged polycyclic compound towards microbes.

In some embodiments, reaction conditions during formation of the oxide shell around a core bridged polycyclic compound may be controlled such that different products and/or different product ratios are obtained. For example, by increasing the concentration of the reaction, metal oxide bridged polycyclic compounds may be formed alongside core-shell bridged polycyclic compounds. Adjusting the concentration may adjust the ratio of metal oxide bridged polycyclic compounds to core-shell bridged polycyclic compounds. By decreasing the concentration of the reaction, only a portion of a core bridged polycyclic compound may covered with an oxide shell. Forming "core-(partial)shell bridged polycyclic compounds" may allow the resulting bridged polycyclic compound to display properties typically exhibited by the core and shell separately. Forming "core-(partial)shell bridged polycyclic compounds" may allow further flexibility and customization of a coating including the bridged polycyclic compounds.

Matrices and Methods of Coating a Surface

In some embodiments, a bridged polycyclic compound (e.g., compound 100, core-shell bridged polycyclic compound) may be suspended within a matrix. A matrix may include a polymeric composition and/or prepolymeric compounds. In some embodiments, a matrix may be formed by cross coupling bridged polycyclic compounds. A matrix is typically composed of one or more monomers, but may include other matrix components/constituents. Often the matrix constituents include one or more "addressable" components or complementary binding pairs, that optionally promote assembly and/or cross-linkage of the matrix. Techniques for combining compounds with an appropriate matrix and applying said matrix to a surface may be found in U.S. Pat. No. 6,929,705 to Meyers et al. ("Meyers"), U.S. Patent Application, Publication No. 2005/0008777 to McCleskey et al. ("McCleskey"), and U.S. Patent Application, Publication No. 2005/0008763 to Schachter ("Schachter"), which are incorporated by reference as if fully set forth herein.

A wide variety of nanostructure-compatible polymers are known to those of skill in the art (see e.g., Demus et al. (ed.) 1998 Handbook of Liquid Crystals Volumes 1-4, John Wiley and Sons, Inc., Hoboken, N.J.); Brandrup (ed.) 1999 Polymer Handbook, (John Wiley and Sons, Inc.); Harper 2002 Handbook of Plastics, Elastomers, and Composites, 4th edition (McGraw-Hill, Columbus, Ohio); and Kraft et al. (1998) Angew. Chem. Int. Ed. 37:402-428.

Exemplary polymers which may be used include, but are not limited to, thermoplastic polymers (e.g., polyalkenes, polyesters, polysilicones, polyacrylonitrile resins, polystyrene resins, polyvinyl chloride, polyvinylidene chloride, polyvinyl acetate, or fluoroplastics); thermosetting polymers (e.g., phenolic resins, urea resins, melamine resins, epoxy resins, polyurethane resins); engineering plastics (e.g., polyamides, polyacrylate resins, polyketones, polyimides, polysulfones, polycarbonates, polyacetals); and liquid crystal polymers, including main chain liquid crystal polymers (e.g., poly(hydroxynapthoic acid)) and side chain liquid crystal polymers (e.g., poly[n-((4'(4"-cyanphenyl)phenoxy)alkyl) vinyl ether]).

1. Some specific embodiments of polymers which may be used in a matrix to support bridged polycyclic compounds may include, but are not limited to, aminoacrylic resins, epoxy resins, and polyurethane resins. Organic polymeric materials used for forming antibiotic-containing films or coatings may include any synthetic, natural or semi-synthetic organic polymers so far as they may be formed into films. Generally, such polymers are thermoplastic polymers or thermoset polymers. Examples of such organic polymeric materials include, but are not limited to, acetate rayon, acrylic resins, acrylonitrile-butadiene-styrene (ABS) resins and acrylic resins, aliphatic and aromatic polyamides, aliphatic and aromatic polyesters, allyl resin, (Allyl), AS resins, butadiene resins, chlorinated polyethylene, conductive resins, copolymerised polyamides, copolymers of ethylene and vinyl acetate, cuprammonium rayons and natural and synthetic rubbers, EEA resins, epoxy resins (e.g., bisphenol, dihydroxyphenol, and novolak), ether ketone resins, ethylene vinyl alcohol, (EN-VAL), fluorine resins, fluorocarbon polymers, fluoroplastics, (PTFE), (FEP, PFA, CTFE, ECTFE, ETFE), high density polyethyelenes, ionomer resins, liquid crystal polymer, (LCP), low density polyethylenes, melamine formaldehyde, (melamine resins), natural polymers such as cellulosics, nylons, phenol-formaldehyde plastic, (PF) phenolic resins, polyacetal, (acetal), polyacrylates, (acrylic), polyacrylonitrile, (PAN), (acrylonitrile), polyamide, (PA), (nylon), polyamide-imide, (PAI), polyaryletherketone, (PAEK), (ketone), polybutadiene, (PBD), polybutylene terephthalate, polybutylene, (PB), polycarbonate, (PC), polycarbonates, polydicyclopentadiene, (PDCP), polyketones, (PK), polyester block copolymers, polyesters, polyesterurethane, polyesterurethaneurea, polyether and polyester block polymers, polyether ketoneketone (PEKK), polyetherether ketone (PEEK), polyetherimide, (PEI), polyethers, polyethersulfone, (PES), polyetherurethane, polyetherurethaneurea, polyethylene isophthalate, polyethylene terephthalate, polyethylene, (PE), polyethylenechlorinates, (PEC), polyglycolic acid, polyhexamethylene terephthalate, polyimide, (PI), polylactic acid, polymethylpentene, (PMP), polyvinyl alcohol, polymethyl methacrylate, polymethyl-co-polybutyl methacrylate, poly-m-phenylene isophthalamide, polyalkenes, polyphenylene oxide, (PPO), polyphenylene sulfide, (PPS), polyphthalamide, (PTA), poly-p-phenylene terephthalamide, polypropylene, (PP), polysiloxanes such as polydimethyl siloxane, polystyrene, (PS), polysulfides, polysulfone, (PSU), polytetrafluoroethylene, polyurethane, (PU), polyvinyl acetate, polyvinyl alcohols, polyvinylchloride, (PVC), polyvinylidene chloride, (PVDC), polyvinylidene fluoride and polyvinyl fluoride, rayon, reconstituted silk and polysaccharides, reinforced polyethylene terephthalate resins, segmented polyurethane elastomers, silicone resins, spandex or elastane elastomers, styrene type specific resins, thermoplastic polyurethane elastomers, thermosetting synthetic polymers such as phenol-formaldehyde copolymer, triacetate rayon, unsaturated polyester resins, urea resins, urethane resins, vinyl chloride resins, vinyl polymers, and vinylidene chloride resins. This group includes reasonable copolymers, terpolymers and mixtures of the species listed.

In some embodiments, matrices may include polymers such as polyethers. Polyethers may include poly(arylene) ethers. Examples of, as well as, methods of making polyethers may be found in U.S. Pat. Nos. 5,658,994 and 5,874,516 to Burgoyne, Jr. et al. ("Burgoyne"); U.S. Pat. No. 6,080,170 to Nash et al. ("Nash"); U.S. Pat. No. 6,187,248 to O'Neill et al. ("O'Neill"); and U.S. Pat. No. 6,716,955 to Burgoyne, Jr. ("Burgoyne"), which are incorporated by reference as if fully set forth herein.

In some embodiments, matrices may include polymers based on acrylic emulsions. Examples of, as well as, methods of making acrylic emulsions and their use in fast dry and extremely durable waterborne, coating composition may be found in U.S. Pat. No. 5,824,734 to Yang ("Yang"), which is incorporated by reference as if fully set forth herein.

In some embodiments, polyurethane/vinyl polymers and copolymers may be employed to form improved coating dispersions used for forming a matrix for compounds described herein. The hybrid polymer coating dispersions offer benefits in shelf stability, self-cross-linkability, surfactant-free nature, water resistance, and low temperature cross-linking. Methods for making such aqueous polyurethane-vinyl polymer dispersion may be found in U.S. Pat. No. 5,521,246 to Tien et al. ("Tien") and U.S. Pat. No. 6,218,455 to Smith et al. ("Smith"), which are incorporated by reference as if fully set forth herein.

In some embodiments, methods for making shelf stable epoxy polymer hybrid water-based dispersions may include (1) polymerizing an unsaturated monomer in the presence of an epoxy resin in water, and (2) blending a separately prepared vinyl acetate based polymer dispersion with a liquid epoxy resin and isophoronediamine. The resulting epoxy hybrid dispersions may be useful as protective film coatings and adhesives. A benefit of the technology in method 1 may be the potential of the prepared hybrid dispersion to be combined later with polyfunctional amine curatives and remain a stable one-pot dispersion system. A benefit of method 2 may be its potential to yield a stable one-pot dispersion system as prepared. Methods for making such aqueous polyurethane-vinyl polymer dispersion may be found in U.S. Pat. No. 5,389,703 to Lee ("Lee") and U.S. Pat. No. 6,235,811 to Robeson et al. ("Robeson"), which are incorporated by reference as if fully set forth herein.

In some embodiments, 3-trimethoxy silyl propyl dimethyl octadecyl ammonium chloride may serve as a matrix for the coatings described herein. When 3-trimethoxy silyl propyl dimethyl octadecyl ammonium chloride is used as a matrix, it may be activated, for example, with hydrolysis.

In some embodiments, reagents and/or matrices may serve dual purposes. Certain compounds may be used as reagents for forming bridged polycyclic compounds described herein as well as acting as a matrix for the bridged polycyclic compounds. For example PMHS may be used as a reductive agent during the synthesis of bridged polycyclic compounds (e.g., compounds 120 and 122) and PMHS may then act as a matrix by cross-linking the reduced bridged polycyclic compounds.

Polymers may be dissolved in suitable solvents or in some cases, dispersed in a suitable liquid or solvent mixture. This may include water. Examples of organic solvents include, but are not limited to, toluene, xylene, methyl ethyl ketone, methyl isobutyl ketone, ethyl acetate, butyl acetate, cyclohexanone, cyclohexanol, alcohols (e.g., methanol, isopropanol, ethanol, etc.) and chlorinated solvents (e.g., dichloromethane) and mixtures thereof. Any suitable polymer may be selected by one skilled in the art which is capable of functioning as a matrix for the antimicrobial agents described (and other optional ingredients) for coating specified. It is evident that depending on the particular application or use and other pertinent considerations, an appropriate choice of polymer may readily be made.

Organic polymers may act as a carrier and matrix for the bridged polycyclic compounds described herein.

In some embodiments, a polymer matrix may have binding properties for the metal precursors (e.g., core-shell bridged polycyclic compounds, metal oxide bridged polycyclic compounds, core-partial shell bridged polycyclic compounds) used to form a surface coating (e.g., polyethylenimine (PEI), a substituted PEI such as carboxylated-polyethylenimine (PEIC) or a polymer such as polyacrylic acid, polypyrolidone, and poly(ethylene-maleic acid)). Polymers may include PEI or substituted PEIs such as PEIC. Typically, the molecular weight of such polymers is greater than about 30,000. Polymers such as PEI and polymer precursors of such polymers may form a matrix for bridged polycyclic compounds which cross couple the bridged polycyclic compounds to one another. PEI may be used as a matrix or medium which assist in spreading bridged polycyclic compounds described herein uniformly. Upon application of a PEI matrix including bridged polycyclic compounds, the composition may be alkylated polymerizing the matrix. Examples of polymer matrices with binding properties for metal oxide based bridged polycyclic compounds include, but are not limited to, polyalkene latex and cellulosic polymer.

Admixing the bridged polycyclic compounds and an organic polymeric compound in a usual manner and then coating the mixture obtained onto a surface (forming it into films) may produce coated products with antimicrobial properties. The formation of the film may be carried out according to any known methods (e.g., for roll coating polymer coatings).

Specialty matrices may be used depending on what surface a coating is applied to. For example, in some embodiments, a coating composition may include pigments and used as a paint or paint equivalent. A paint equivalent may include a wet adhesion monomer containing a cross-linkable hydroxyl group useful in the making of latex paints. Methods for making such aqueous polyurethane-vinyl polymer dispersion may be found in U.S. Pat. No. 6,538,143 to Pinschmidt, Jr. et al. ("Tinschmidt"), which is incorporated by reference as if fully set forth herein. In some embodiments, coating compositions described herein may include specialty matrices for ink jet paper coatings. Ink jet paper coatings may be made having high optical density images, excellent water fastness, and fast print drying times. The coating composition comprises may include inorganic pigments (e.g., silica), a non-polymeric polyamine and polyvinyl alcohol. High optical density images and excellent water resistance may be achieved by incorporating amine functional emulsion polymers in the ink jet coating formulation. Emulsion polymers may include 2-(dimethylamino) ethyl methacrylate (DMAEMA), vinyl acetate, and poly(vinyl alcohol). Methods for making such aqueous polyurethane-vinyl polymer dispersion may be found in U.S. Pat. No. 6,455,134 to Rabasco ("Rabasco") and U.S. Pat. No. 6,458,876 to Rabasco et al. ("Rabasco"), which are incorporated by reference as if fully set forth herein.

Solvents (or liquids to disperse the polymer) which may be used include, but are not limited to, aliphatic hydrocarbons, aromatic solvents, alcohols and other oxygenated solvents, substituted hydrocarbons, phenols, substituted aromatic hydrocarbons and halogenated aliphatic hydrocarbons. Each resin system has a group of solvents and diluents compatible with the resin and suitable for film forming. In some cases the organic solvent is only used to disperse the resin powder. It is contemplated that water may be used as solvent/diluent or dispersant for some resin compositions.

The polymer coatings may contain other additives as well as antimicrobial compositions. They may contain, for example, polymerization catalysts, stabilizers, delustering agents, optical whitening agents, organic or inorganic pigments, inorganic fillers, plasticisers and so on. It is also possible that the antimicrobial particles themselves may fulfill a dual role and provide the benefits of some of the aforementioned additives.

Matrices may include white pigments such as magnesium oxide, calcium oxide, aluminum oxide, zinc oxide, titanium dioxide, silicon dioxide, calcium carbonate, magnesium carbonate and barium sulfate. In addition, to the present antibacterial oxide or zeolite may be added additives such as magnesium silicate, aluminum silicate, zinc silicate, silica gel-zinc, synthetic hydrotalcite, aluminum tripolyphosphate.

Conventional procedures for incorporating powders in polymer compositions may be used to prepare matrices with bridged polycyclic compounds as described herein. Antimicrobial compounds may be added to a monomer or to an intermediate product prior to polymerization. In some embodiments, antimicrobial compounds may be mixed or compounded with a finished polymer before it is applied as a film. Pre-coating of antimicrobial particles with polymers greatly facilitates incorporation of the particles in the bulk polymer. This may be done, for example, by slurrying the antimicrobial compounds with a solution of the polymer, then removing the solvent by drying. From about 0.1 to about 10% by weight of polymer based on the coated antimicrobial compounds and from about 0.5 to about 5% by weight of polymer based on the coated antimicrobial compounds may be suitable for this purpose.

In some embodiments, a coating is placed onto a surface wherein the coating composition is comprised of dispersed epoxy resin particles. The epoxy resin may be a solid or liquid epoxy resin. The epoxy resin may be a liquid that is dispersed (i.e., emulsified) within the solvent. Exemplary epoxy resins include diglycidyl ether of bisphenol A, such as those available from The Dow Chemical Company, Midland, Mich. under the trade name D.E.R., and from Shell Chemical Company, Houston, Tex. under the trade name EPON or EPI-REZ and phenol and cresol epoxy novolacs, such as those available under the trade name D.E.N. from The Dow Chemical Company, Midland, Mich. Other examples of useful epoxy resins include those described in U.S. Pat. Nos. 5,118,729, 5,344,856 and 5,602,193, which are incorporated by reference as if fully set forth herein. The amount of epoxy resin in the coating composition may be any amount sufficient to coat a surface that, subsequently, may be cured to form a microbial resistant coating on the surface.

The epoxy coating composition may also contain a surfactant that forms an epoxy resin in water dispersions, wherein the epoxy resin molecules have a neutral or positive surface charge, the surfactant being a nonionic surfactant, amphoteric surfactant or mixture thereof. The nonionic surfactant may be, for example, a nonionic surfactant or combination of surfactants known to form oil in water emulsions. Exemplary nonionic surfactants include, but are not limited to, polyglycol ether of an epoxy, an alcohol, fat, oil, a fatty acid, a fatty acid ester or an alkylphenol. Exemplary amphoteric surfactants include, but are not limited to, those known in the art, such as alkyl betaines and dihydroxyethyl glycinates.

In some embodiments, an epoxy resin may be polymerized such that bridged polycyclic compounds suspended within the matrix are cross-coupled to one another and to a surface. In some embodiments, a nucleophile, specifically a dinucleophile may be employed to accomplish such an end (e.g., a diamine). Examples of epoxy resins as well as techniques for polymerizing resins may be found in U.S. Pat. No. 5,350,814 to McGarry ("McGarry"), which is incorporated by reference as if fully set forth herein.

Examples of expoxy resins may include the butyl glycidyl ether; styrene oxide; phenyl glycidyl ether; p-butyl phenol glycidyl ether; polyglycidyl ethers of polyhydric polyols; cycloaliphatic epoxy resins made from epoxidation of cycloalkenes with peracids; the polyglycidyl esters of aliphatic, cycloalipnatic, or aromatic polycarboxylic acids; the polyglycidyl ethers of polyphenols, (e.g., bisphenol A); and novolak resins (e.g., epoxy phenol novolak resins and epoxy cresol novolak resins); and aromatic glycidal amine resins (e.g., triglycidyl derivatives of p-aminophenol).

Amine-terminated and/or ammonium-terminated flexible polymers may include amine-terminated polyethers, amine-terminated diene based polymers, amine-terminated hydrogenated diene or polyalkene base polymers, saturated polyesters, copolymers of vinyl substituted aromatics and conjugated dienes, and amine-terminated copolymers of nitrile rubber. Amine-terminated flexible polymers may include branched polymers. The amine termination may be one or more ends of the polymer chains. Thus, as amine reactants, they may be mono-, di- or trifunctional, as well as, blends of mono-, di-, and trifunctional polymers.

Flexible epoxy resins are made by reacting uncured epoxy resin with an amine curing agent in the presence of a low molecular weight acrylate copolymer having functional groups that may react with the epoxy resin or the amine curative. For example, acrylate copolymers are made from butyl acrylate and acrylic acid or maleic anhydride and have number average molecular weights of 1000 to 6000. The resulting flexible epoxy resins exhibit elongations up to 200%. Examples of epoxy resins, and specifically techniques for forming flexible epoxy resins may be found in U.S. Pat. No. 5,698,657 to Conner et al. ("Conner"), which is incorporated by reference as if fully set forth herein.

The amount of surfactant present in the coating composition may be any amount sufficient to disperse the epoxy resin and cause the epoxy resin particles in the dispersion to have a neutral or positive charge. Generally, the amount of surfactant is at least about 0.1 percent by weight or at least about 0.5 percent by weight. Generally, the amount of surfactant is at most about 10 percent or at least about 5 percent by weight of the total coating composition weight.

The epoxy coating composition may contain a latent curing agent. Examples of latent curing agents include dicyandiamide and blocked isocyanates, such as an alcohol-blocked toluene diisocyanate. The latent curing agent is dicyandiamide. The amount of latent curing agent is an amount sufficient to cure the epoxy resin and generally should be an amount that is not so great that the coating, after curing, fails to provide the desired properties. Generally, the amount of latent curing agent is at least about 0.1 percent by weight or at least about 0.5 percent by weight. The amount of latent curing agent is at most about 10 percent or at least about 5 percent by weight of the total coating composition weight.

Examples of curing agents useful for curing epoxy resins may be found in U.S. Pat. No. 6,008,313 to Walker et al. ("Walker"), which is incorporated by reference as if fully set forth herein.

The aqueous epoxy coating composition contains water in an amount sufficient, for example, to provide an epoxy in water emulsion when the epoxy is a liquid. The water should also be sufficiently pure to provide a water matrix that fails to cause coagulation of the particles (e.g., epoxy or filler particles) due, for example, to impurities (e.g., ionic impurities).

The polymer film compositions may be clear or may contain pigment particles or dyes. The pigment particles may include titanium dioxide, alumina or silica. Pigment particles may include titanium dioxide particles from about 0.1 to about 10 microns in median particle size. Pigment particles may include titanium dioxide particles from about 0.2 to about 5 microns in median particle size.

In some embodiments, a coating may include fillers. Fillers may impart, for example, opacity or improved wear resistance to the coating composition after it has been cured. Exemplary fillers include ceramic particles or whiskers and known surface treated metal pigments. Fillers may include a ceramic. Ceramics may include oxides, borides, nitrides, carbides, hydroxides, carbonates, silicides, silicates and alloys thereof.

When a coating composition contains a filler, the filler is generally present in an amount of about 1 percent to about 50 percent by weight of the total coating composition weight. The amount of the filler, when present, may be at least about 2 percent or at least about 5 percent. The amount of the filler, when present, may be at most about 40 percent or at most about 35 percent.

In some embodiments, a coating composition may include a cross-linking catalyst, for example, to increase the rate of cross-linking (i.e., cure) of the epoxy at a temperature. Generally, the catalyst may be, for example, a tertiary amine or imidazole. Examples of the catalyst that may be employed in the coating composition include 2-methylimidazole, benzyldimethylamine, dimethyl aminomethyl phenol or tris (dimethylaminomethyl)phenol.

When the coating composition contains a cross-linking catalyst, the catalyst is generally present in an amount of about 0.001 percent to about 1 percent by weight of the total coating composition weight. The amount of the catalyst, when present, is at least about 0.002 percent, at least about 0.005 percent, ory at least about 0.01 percent to at most about 0.7 percent, at most about 0.5 percent and at most about 0.3 percent by weight of the total weight of the coating composition.

In some embodiments, a coating composition may also contain a small amount of defoamer. The defoamer may include any suitable defoamer, such as those known in the art. Exemplary defoamers may include siloxane-based defoamers. The defoamer, when present, is present only in a quantity necessary to control the foaming of the coating composition. It has been found that, in general, the defoamer impedes the adherence of the coating composition to a metal surfaces. The amount of defoamer, when present, is generally present in an amount of at most about 0.15 percent, at most about 0.05 percent, or at most about 0.02 percent by weight of the total weight of the coating composition.

In some embodiments, compounds or additives included in an antimicrobial composition may be selected to adjust particular properties of the composition or to introduce new properties to the composition. Adjusting properties of a composition based on a selection of a particular compounds or additives allows further customization of a composition. In some embodiments, compounds or additives which have or enhance antimicrobial properties and/or anti-inflammatory properties (e.g., boron (e.g., boric acid), zinc) may be used. In some embodiment, compounds or additives may adjust the hydrophilicity or hydrophobicity of the complex. Research has held that specific additives do affect the antimicrobial activity of quaternary ammonium compounds in certain coating compositions (e.g. boric acid, tetrafluoroborate counter ion, hexafluorophosphate, bis(trifluoromethanesulfonyl) imide, EDTA, disodium EDTA). In some embodiments, before a coating composition is applied to a surface the surface may be cleaned. A degreasing operation may be performed to promote a good adherence of the coating. If a surface is not degreased, the fatty substances and other surface contaminants that are not removed are liable to reduce the adherence of the resin coating and to give rise to a non-homogeneous deposit comprising areas without coating.

In some embodiments, a surface is desirably free of contaminants, such as petroleum greases and oils, that may cause the pretreatment and coating to be insufficiently adhered to the surface. Prior to applying the coating composition a surface may be cleaned. Various methods of cleaning are well known in the art. The particular cleaning method should be able to adequately remove residual oil or dirt from the surface but should not cause over-etching of the surface, except when desirable. Exemplary cleaning methods may include, but is not limited to, solvent cleaning (such as a chlorinated solvent (e.g., methylene chloride), ketone (e.g., acetone), alcohol (e.g., methanol), or toluene), emulsion cleaning, alkaline cleaning, acid cleaning, pickling, salt bath descaling ultrasonic cleaning, roughening (e.g., abrasive blasting, barrel finishing, polishing and buffing, chemical etching and electro-etching).

Degreasing of a surface may be generally performed either chemically or electrolytically. A surface may be cleaned by mechanical means (e.g., grinding or sandblasting). A surface may be degreased chemically by being placed in contact with a solution containing halogenated organic solvents (e.g., methylene chloride, 1,1,1-trichloroethane, perchloroethylene, or trichloroethylene).

The degreasing operation may be performed electrolytically in an electrolysis bath or electrolyte including an aqueous solution containing alkaline mixtures similar to those just specified or else calcium carbonate or potassium hydroxide. The electrolyte may contain an alkaline compound in a proportion of from about 0.5 to about 20 wt. %. The temperature of the electrolyte may be between from about 25° and about 95° C. The surface may be subjected to a current density of between 0.1 and 20 A/dm2 for a period longer than about 0.1 seconds.

The surface may be degreased chemically by employing a solution based on alkaline mixtures containing one or more agents including, but not limited to, caustic soda, soda ash, alkaline silicates, sodium hydroxide, sodium carbonate, sodium metasilicate, phosphates, alkaline builders, ammonium acid phosphate, ammonium hydroxide, monoethanol amine, and dimethylamine oxide and optionally containing one or more of the agents including, but not limited to, complexing agents, surfactants, sequestrant, builders, surface-active agents, defoaming agents, and mixtures thereof. The alkaline degreasing solutions and alkaline degreasing agents employed for cleaning metal surfaces are well known in the literature. Exemplary methods will use a solution of potassium or sodium hydroxide at a concentration of from about 1 to about 5%. The degreasing solution is applied to the surface by known spray or dip methods. Generally, these are applied at a temperature of from about 50 to about 200° C. or from about 60 to about 80° C.

Alkaline builders may be generally classified into three types, namely, the strong alkaline type composed mainly of sodium silicate or trisodium phosphate and/or caustic soda, medium alkaline type composed of one or more than one of the following; disodium phosphate, sodium pyrophosphate, sodium carbonate, etc., and mild alkaline type composed of disodium phosphate, sodium bicarbonate, sodium tripolyphosphate, sodium sesquicarbonate, etc. Any alkaline builder of the above types may be employed therefore.

The temperature of the alkaline solution may be generally between about 25° and about 95° C. The temperature of the alkaline solution may be greater than about 50° C. The temperature may be greater than about 60° C. A surface may be generally subjected to the solution for a period longer than 0.1 second. A surface may be subjected to the alkaline solution for a period longer than 1 second. A surface may be subjected to the alkaline solution for a period longer than 3 seconds. In general, alkaline chemistry can be deactivating towards antimicrobial ammonium salts. However, this can be counteracted by adjusting pH back to neutral or acidic by neutralizing the surface before adding the antimicrobial coating. Inclusion of chelating agents such as EDTA in the antimicrobial formulation can also help avoid deactivation by magnesium, calcium or other counterions of the alkaline solution and/or painted surface before antimicrobial coating application. An antimicrobial coating formulation that is acidic may also aid in neutralizing the pH of the alkaline solution cleaned surface.

The concentration of the cleaning agent and the surfactant must be sufficient to remove substantially all oil and other contaminants from a surface to be coated, but must not be so high that a significant amount of foaming occurs. Typically, the water rinse step may be avoided if the cleaning bath is not too concentrated, which is acceptable in the event that the surface is initially relatively clean.

A surface having been contacted by the cleaning solution may be generally rinsed with water (neutral medium) or other known rinse agent, also by known spray or dip methods. Air-drying or other drying means may generally follows rinsing.

In some embodiments, a surface cleaning step may be eliminated or combined with the surface pre-treatment step in certain circumstances depending upon the condition of the surface and the type of pre-treatment utilized.

In some embodiments, a surface to which a coating composition is applied may be pretreated to enhance the adhesion of the coating composition after curing. The pretreatment may be, for example, the formation of an interlayer on the surface that enhances adhesion of the coating composition after curing. For example, the interlayer may be a chemical conversion layer (e.g., a silane, phosphate, chromate, epoxy, or oxide coating) or the interlayer may be an adhesive coating. Generally, pretreatment may be performed by contacting the surface with chromium phosphate, chromium chromate, zinc phosphate, iron phosphate, or an organic epoxy-based composition.

The interlayer may be any thickness sufficient to enhance the adhesion of the coating composition during application and after curing but, in general, the interlayer is at most about 100 percent of the thickness of the cured coating of the antimicrobial composition on one side, the interlayer is at most about 50 percent of the thickness of the cured coating of the antimicrobial composition, or the interlayer is at most about 10 percent of the thickness of the cured coating of the antimicrobial composition. The interlayer, typically, is between about 0.01 to about 30 microns thick. Thickness of the interlayer is at least about 0.1 microns, at least about 0.2 microns, or at least about 0.5 microns. Thickness of the interlayer is at most about 20 microns, at most about 15 microns, or at most about 10 microns.

In some embodiments, a surface may be pretreated with an aqueous composition including phosphoric acid and a divalent metal ion when a the surface is steel, zinc or zinc based alloys or zinc aluminum alloy coated steel, aluminum or aluminum alloy. Any divalent metal ion may be used as the divalent metal ion for use in the composition. Generally, the metal may include, but not limited to, divalent transition metal ions (e.g., Mn, Co, Fe, Ni, and Zn), and alkaline earth divalent metal ions (e.g., Mg, Ca, Sr, and Ba). The metal may be Fe or Zn. The metal may be Zn. Silicate may be added to precipitate out any metal ions that may then be removed from the phosphating composition.

To accelerate the formation of the phosphate layer, oxidants may be added (e.g., bromate, chlorate, nitrate, nitrite, organic nitro compounds, perborate, persulfate or hydrogen peroxide, m-nitrobenzene sulfonate, nitrophenol or combinations thereof).

In some embodiments, to optimize the layer formation on certain materials, sulfate, simple or complex fluoride ions, silicofluoride, boron fluoride, citrate, tartrate, hydroxy-carboxylic acids, aminocarboxylic acids, condensed phosphates, or SiO-containing compounds (e.g., alkali metal metasilicate, alkali metal orthosilicate, and alkali metal disilicate) and mixtures thereof may be added.

When a surface is predominantly galvanized metal and/or steel, the pretreatment may include contacting the metal surface with an aqueous composition comprising phosphoric acid and a divalent metal ion, the composition generally having a total phosphate content from about 0.01 to about 3 moles/liter, a total phosphate content from about 0.02 to about 2 moles/liter, or a total phosphate content from about 0.1 to about 1 moles/liter. The composition may have divalent metal ion content of from about 0.001 to about 2 moles/liter (based on metal ion content), a metal ion content of from about 0.01 to about 1 moles/liter, or a metal ion content of from about 0.05 to about 0.5 moles/liter.

In some embodiments, a surface may include an aluminum, aluminum alloy, or aluminized steel sheet, in order to enhance corrosion resistance, surface hardness and adhesive property of the substrate, an oxide film (alumite) may be formed on the sheet by pretreatment (anodizing) with caustic soda, oxalic acid, sulfuric acid or chromic acid.

The quantities of the components in a coating composition may vary but are typically chosen to suit a particular material/substance which is prevalent in the surface being treated.

The pretreatment compositions may be prepared by the addition of the components in any convenient order known to one skilled in the art.

In some embodiments, after a coating composition is applied, the coating is at least partially cured or dried to harden and adhere the coating to a surface. The curing is by means suitable to the polymer composition used. Curing may be accomplished using methods including, but not limited to, heating, infrared radiation, fluorescent radiation, ultraviolet radiation, gamma or beta radiation, X-ray radiation, or combinations thereof. In an exemplary method, a surface, immediately after coating, is passed through a gas-fired heating zone where solvents are evaporated and the resin is cured or dried. The polymer may be at least partially cured by heat. Heat curing may be employed to raise the temperature of the coating to accelerate cross-linking reactions. Heat curing may be accomplished by various heating means such as an electric heating oven, hot air heating oven, infrared heating oven, and high-frequency heating oven. For curing, a heating temperature and time are properly selected in consideration of the formulation of a coating composition, the size and composition of a surface material, the capacity of an oven, and other factors. The particular temperature is dependent on such things as the particular epoxy, curing agent and catalyst employed and curing time desired. The temperature, however, should not be so great that the cured coating is degraded, for example, by decomposing. Generally, the drying or curing treatment is carried out under normal pressure or reduced pressure at a temperature of at least about 50° C. to at most about 400° C., depending upon the from what material the surface is formed.

The time at the temperature of cure may be any time necessary to cure the surface coating and is desirably as short as practical. Generally, the time at the curing temperature may be at least about 0.1 minute to at most about 24 hours. The time at the cure temperature may be at least about 10 minutes, at least about 5 minutes, or at least about 0.5 minute. The time at the cure temperature may be at most about 2 hours, at most about 1 hour, or at most about 0.5 hour. As well within the knowledge of those skilled in the art, the temperature and time are in a relative relationship and also the conditions vary depending on the properties of coating required.

Immediately after heating to cure or dry the coating, the coated surface may be subjected to quenching in order to harden the coating. The quenching may be by any suitable means as known in the art such as by water or other coolant immersion, spray, or mist or by cold air.

The thickness of the coating may be in the range of from about 0.5 to about 30 microns. Thickness of a surface coating may be at least about 2 microns, at least about 3 microns, or at least about 4 microns. Thickness of a surface coating may be at most about 20 microns, at most about 15 microns, or at most about 10 microns.

After curing, the applied coating composition, a surface having a cured resin coating adhered thereto is formed generally having antimicrobial properties. In some embodiments, a coating that is formed, typically, has self-cleaning properties.

In some embodiments, bridged polycyclic compounds describes herein may be used to form antimicrobial coatings for surfaces. Bridged polycyclic compounds may be suspended in matrices as described herein which may be used to couple the bridged polycyclic compounds to the surface and/or to each other. In some embodiments, coating may be self-cleaning (e.g., superhydrophobic, inhibit microbial adhesion). Antimicrobial coatings may be applied to any surface which would benefit any of the customizable properties (e.g., antimicrobial, self-cleaning) imparted by coatings described herein. Coatings may be applied to medical devices. Medical devices may include invasive medical devices such as catheters which are temporarily positioned within a patient or subject. In a specific embodiment, medical devices may include invasive dental devices (e.g., drills, suction tubes). Medical devices may include invasive devices such as medical implants (e.g., dental implants). Medical devices may include non-invasive devices and systems (e.g., kits, kit packaging, trays, medical/dental equipment, medical/dental instruments, medical containers such as blow fill seal vials and bottles for pharmaceuticals).

Surfaces to which antimicrobial coatings may be applied include, but are not limited to, countertops, doorknobs, faucets, handles, portions of public areas, etc.

Other examples of surfaces and materials to which a surface coating may be applied are presented herein below. For example, fiberglass surfaces include resins, polymers, reinforcing fabric and fibers. Surfaces made from fiberglass include but are not limited to bathtubs, boats, motorcycles, car bodies, canoes, airplanes, model aircraft, jet skis, sculptures, as well as traditional industrial molding and model-making articles.

There are seven basic types of surface plastics which include polyethylene terephthalate (PET), high density polyethylene (HDPE), polyvinyl chloride (PVC), low density polyethylene (LDPE), polypropylene (PP), polystyrene (PS), polyester, polymers and mixtures thereof. These types of plastics may also be combined with other materials including, but not limited to bridged polycyclic compounds, to make all sorts of composites. Manufacturers are unlimited in the number and types of articles that may be made from plastic. Carbon and graphite fibers are high-strength materials that are used as reinforcing agents in plastic composites. Examples of plastic articles include vials, blow-fill-seal containers, bottles, jars, jugs, bags, covers, pipes, furniture, containers, caps, cups, trays, aircraft fuselages and wings, spacecraft structures, and sports equipment.

Both ferrous and nonferrous metal surfaces are available for use with surface coatings described herein. These include aluminum, brass, bronze, chrome, copper, tin, zinc, iron, stainless steel, and steel. Examples of metal surfaces include, but are not limited to, buildings, doors, window frames, automobiles, boats, structures, and many more too numerous to mention.

Three basic types of glass include sheet, plate, and float. These basic glass types may be changed to meet modern requirements for comfort, security, safety, and architectural needs by adding chemicals or other ingredients during fabrication and processing.

There are a number of distinct dishware surface types available. Dishware may include glassware, ceramic ware, plastic ware, wood ware and metal ware. Examples of dishware may include agateware, basalt, bisque, bone china, cauliflower ware, cream ware, delft, earthenware, flambe, hard paste porcelain, ironstone, jackfield, jasper, lusterware, majolica, marbled, parian, pate-sur-pate, pearl ware, porcelain, redware, salt glaze, slipware, snowman-porcelain, soft paste porcelain, spatter ware, staffordshire figures, stoneware, tortoiseshell, and transfer ware. Utensils may also be made from any of the above materials.

Ceramic surfaces include glazed tile, mosaic tile, and quarry tile. Applications of ceramic tiles include countertops, walls, floors, ceilings and appliances.

Other types of surfaces, such as sinks, bath tubs, towel racks, and toilets may be made of porcelain, ceramic, or other materials. Other surfaces may include any surface associated with a bathroom and/or kitchen area (e.g., plumbing and/or electrical fixtures).

There are many types of wood surfaces available. Examples of some types of wood include, but are not limited to, alder, ash, aspen, beech, birch, bocote, bubinga, butternut, cedar, cherry, cocobolo, canarywood, cypress, ebony, hickory, holly, kingwood, lacewood, locust, mahogany, maple, oak, osage, parawood, padauk, pecan, persimmon, poplar, purpleheart, redheart, rosewood, spanish cedar, sycamore,. teak, tulipwood, walnut, wenge, zebrawood, ziricote. Articles made from wood may include furniture, baseball bats, chairs, stools, furniture, handles, motor-vehicle parts, barrels and crates, sporting and athletic goods, railroad ties, veneer, flooring, treated lumber, such as that used for decks, siding, crates, and interior finishing.

Three basic types of stone surfaces available include igneous, metamorphic, and sedimentary. Some of these surfaces may include granite, marble, slate, sandstone, serpentinite, schistose gneiss, quartzite, sandstone, limestone and fieldstone. Stone is often used in construction of buildings, roads, walls, fireplaces, and monuments. There are a number of types of concrete surfaces available as well. These surfaces may include unreinforced concrete, reinforced concrete, cast-in-place concrete, precast concrete, post-tensioned concrete, and prestressed concrete. Examples of concrete surfaces may include building components, bridge components, walls, streets, curbs and gutters. Four types of asphalt include hot-mix asphalt, cold-mix asphalt, glassphalt, and rubberized asphalt. Asphalt is used on road surfaces, walls, roofing, and sporting tracks. There are a multitude of mineral surfaces available. Minerals include ores of metal and other natural substances that may be mined. Examples of mineral surfaces may include jewelry, furniture, building components and many more. Finally coated and painted surfaces are also examples of hard surfaces that may be modified to derive the desired benefits.

In certain aspects, surfaces described herein are may be rigid (not flexible). Examples of surfaces that are not considered to be rigid would include films. In certain aspects, surfaces described herein are more rigid than a synthetic resin film having a thickness of 0.1 mm.

In some embodiments, it is desirable for the coating compositions to be applied to exposed surfaces. As used herein, the term "exposed surfaces" includes exterior surfaces that are exposed to the elements. In some embodiments, the coating compositions are applied to interior surfaces that are subject to periodic contact with water (including, but not limited to the bathroom surfaces described above). Interior surfaces that are subject to periodic active contact with water may be distinguished from interior surfaces on which water or condensation merely passively accumulates, based on the fact that the former may have water showered, rinsed, or splashed thereon.

In some embodiments, surfaces described herein need not be transparent. That is, the surfaces may be translucent or opaque.

Construction Applications using Compositions Comprising Bridged polycyclic Compounds Specialty matrices may be used depending on what surface a coating is applied to. For example, in some embodiments, a coating composition may include pigments and used as a paint or paint equivalent. A paint equivalent may include a wet adhesion monomer containing a cross-linkable hydroxyl group useful in the making of latex paints. Methods for making such aqueous polyurethane-vinyl polymer dispersion may be found in U.S. Pat. No. 6,538,143 to Pinschmidt, Jr. et al. ("Pinschmidt"), which is incorporated by reference as if fully set forth herein.

In some embodiments, special formulations of coating may be prepared for use in various areas of construction (e.g., architectural construction).

An antimicrobial coating composition may be prepared by paint making techniques which are known in the coatings art. In some embodiments, at least one pigment is well dispersed in a waterborne medium under high shear such as is afforded by a mixer. Then an emulsion-polymerized addition polymer is added under low shear stirring along with other coatings adjuvants as desired. The antimicrobial coating composition may contain, in addition to the pigment(s) and the latex polymer, conventional coatings adjuvants such as, for example, colloids, emulsifiers, coalescing agents or solvents (e.g., DMF and ethylene glycol), curing agents, thickeners, humectants, wetting agents, biocides, plasticizers, antifoaming agents, colorants, waxes, pH adjusters (e.g., boric acid), and antioxidants.

In particular, coalescing agents or solvents are used in architectural and industrial latex coatings to promote film formation, and selection of the proper coalescing solvent is a key to the formulation of superior latex coatings. A coalescent is often used in water-based systems as a fugitive plasticizer to soften the resin particles, enabling them to fuse into a continuous film. During the drying process, most or all of the coalescent evaporates, allowing the film to achieve the desired hardness. Other coalescing agents or solvents may include, but are not limited to, dimethylsulfoxide, dimethylformamide, acetone, butanol, propanol, isopropanol, pentanol, hexanol, propylene glycol, ethylene glycol, ethylene glycol 2-ethylhexyl ether, di(ethylene glycol)2-ethylhexyl ether, ethylene glycol butyl ether, di(ethylene glycol)hexyl ether, 3-ethylhexanol, hexanol, 1,4-butanediol and the like.

In some embodiments, complexing agents (e.g., chemical compounds, polymers) may be added to a antimicrobial composition. A good example of this might be in a composition including pigments which will be used as an antimicrobial paint. Certain compounds (e.g., magnesium) may reduce the effectiveness of quaternary ammonium based antimicrobial compositions, however, the addition of complexing agents which might neutralize these compounds may overcome this problem. An example of a complexing agent may include, but is not limited to, ethylenediaminetetraacetic acid ("EDTA") and salts thereof (e.g. disodium EDTA).

The antimicrobial coating composition may be applied to a surface such as, for example, metal, wood, sheet rock, ceramic, cultured marble and plastic, using conventional coating application methods such as, for example, brush, roller, drawdown, dipping, curtain coater, and spraying methods such as, for example, air-assisted spray, airless spray, high volume low pressure spray, and air-assisted electrostatic spray.

Coatings including the bridged polycyclic compounds as described herein may include antimicrobial paint compositions, caulk compositions, adhesive compositions and sealant compositions, and methods of preparing such compositions.

Coatings including the bridged polycyclic compounds as described herein may include a latex paint composition comprising an antimicrobial latex prepared as described herein, a pigment, and, optionally, thickener.

In some embodiments, antimicrobial compositions may take the form of a coating, adhesive, sealant or elastomer.

Coatings and Paints: Paints are typically liquids which are useful for application to a substrate, such as wood, metal, glass, ceramics, fiberglass, composite materials, cardboard, corrugated board, paper, textiles, non-woven materials, plastic, foam, tape or a combination thereof, in a thin layer. Paints are typically used to protect the surface of the substrate from elemental damage and/or physical damage. Paints are also commonly used for decoration and aesthetic purposes. Paints find very broad commercial use and also find a variety of uses in the home. Paints, their formulations, ingredients, additives and processing conditions are generally described in Kirk-Othmer-Paint; pg. 1049-1069, Vol. 17; 1996, by Arthur A. Leman, the disclosure of which is incorporated herein.

Typically, paints are described as latex, alkyd, or oil-based paints. Additionally, a wide variety of paints are water-based. These designations identify the binder used in the manufacture of the paint and the solvent, if any, which is used. Typically classes of latex paints include gloss, semi-gloss, flat, and satin. These terms describe the shininess of the paint surface after the paint as dried on the substrate. Paints typically contain binders/resins, such as latex emulsions. A common latex emulsion employed in paints is based on acrylic and vinyl acetate. Paints often include pigments (organic and inorganic), inorganic extenders, filler pigments, solvents, and additives, such as thickeners, protective colloids, biocides, driers, pigment dispersants, pigment extenders, adhesion promoters, surfactants, and defoamers. When paints are manufactured, surface active agents are used to stabilize the emulsion polymerization and also regulate the resulting polymer particle size.

In some embodiments, a formulation may also contain matte finish additives (low to no gloss or flat) and thixotropic additives (anti-sag components) formulations including metal oxides (e.g. silica) and surface modified metal oxides (e.g. silica with trimethyl silyl, vinyl dimethyl silyl, etc.) may be found in U.S. Pat. No. 6,720,368 which is incorporated by reference as if fully set forth herein.

The aforementioned monomers may be utilized to prepare latexes useful in coatings and paints. Typically the monomers are selected to give an acrylic latex emulsion, for durable exterior paint. These monomers may include methyl methacrylate, butyl acrylate, and 2-ethylhexyl acrylate, and mixtures thereof. Non-acrylic based monomers are typically used for interior paints, except in the cases of gloss and semi-gloss paints. Among other monomers, vinyl acetate, butyl acrylate and mixtures thereof, are commonly used in a variety of paint formulations.

Alkyd resins are produced by reaction of a polybasic acid, such as phthalic or maleic anhydride, with a polyhydric alcohol, such as glycerol, pentaerythitol, or glycol, in the presence of an oil or fatty acid." (See Kirk-Othmer-Paint; pg. 1049-1069; Vol. 17; 1996; Arthur A. Leman). Alkyd resins are typically described as long-oil, medium-oil, and short-oil alkyds. Such description is based on the amount of oils and/or fatty acids in the resins. Long-oil alkyds generally have an oil content of 60% or more; short-oil alkyds, less than 45%; and medium-oil alkyds have an oil content in between the two. The short- and medium-oil alkyds are based on semidrying and nondrying oils, whereas long-oil alkyds are based on semidrying and drying oils.

Typical pigment extenders used in paints include, for example, titanium dioxide, calcium carbonate, talc, clay, silica, zinc oxide, feldspar, corrosion resistance extenders, mildew resistance extenders, and film-hardening extenders, and mixtures thereof Solvents typically used in paints included, for example, mineral spirits, glycol ethers (e.g. ethylene glycol and propylene glycol) and the like. In addition to binders, solvents, pigments, and extenders, many paints contain additives. Additives include, for example, thickeners, pigment dispersants, surfactants, defoamers, biocides, mildewcides, preservatives, driers, defoamers, antiskinning agents and pH adjusting agents and mixtures thereof (e.g. acids and bases). Additional additives include hydroxyethylcellulose, hydrophobically modified alkali-soluble emulsions, and hydrophobically modified ethylene oxide urethanes.

Adhesives and Sealants: Sealants have been generally described in Kirk-Othmer-Sealants; pg. 650-666; Vol. 21; 1997, by Richard Palmer and Jerome Kloswski, the disclosure of which is incorporated herein. A sealant is a material that is installed into a gap or joint to prevent water, wind, dirt, or other contaminants from passing through the joint or gap. Sealants, which can also be defined by how they are tested, are rated by their ability to stretch, twist, bend, and be compressed while maintaining their bulk properties so they do not tear apart under stress. The adhesion required of a sealant is simply the strength to hold the sealant in position as it is stressed and strained. Adhesives are used to transfer loads and are typically designed with much higher tensile and shear strengths than sealants. The most important rating of an adhesive in many applications is the determination of how much load it can handle. Some sealants are used as adhesives and some adhesives as sealants and thus arises the occasional blurring of their roles. If the material's primary function is the exclusion of wind, water, dirt, etc., it is typically a sealant.

Sealants include high performance sealants, such as for example, silicones, urethanes, and polysulfides, medium performance sealants, such as for example, acrylic sealants, and low performance sealants, such as for example, butyls, putties, and caulks. The measure of the stress of a sealant at a specific strain is referred to as the modulus of elasticity, sometimes called the secant modulus. This important sealant property describes the force exerted by a sealant as it is stressed. Because a primary function of sealants is to adhere to the substrates it is in contact with, the force generated by a joint opening or closing are transmitted by the sealant to the substrate-sealant bond line. A primary factor in sealant durability is its ability to resist decay from environmental elements. For most typical applications this includes extremes of high and low temperature, water, oxidation, and sunlight. Other factors include weatherability and adhesion life. One of the more destructive elements is exposure to sunlight; specifically, ultraviolet (UV) light. All sealants are affected by weathering but there is much difference in the effect of weathering on different sealants. A second key factor in determining the durability of a sealant is the ability of the sealant to adhere to the substrate through its lifetime. A sealant may have excellent resistance to uv effects, but if it has poor adhesion performance and fails adhesively, it is of little use.

Commercially available silicone sealants are typically one of three curing types: moisture-reactive (curing) sealants, moisture-releasing (latex) sealants, and addition-curing sealants. The formulation of moisture-curing silicones includes a silicone polymer, filler, a moisture-reactive cross linker, and sometimes a catalyst. A newer class of silicone sealants are known as the silicone latex sealants. These sealants are silicone-in-water emulsions that cure by evaporation of the emulsifying water. The silicone latex polymer is prepared by first emulsifying a low molecular weight silicone polymer in water and then polymerizing it to the desired molecular weight. Inherent to emulsion polymerization is the ability to produce high molecular weight polymers at a low emulsion viscosity. Next, a silicone cross-linker is added with a condensation catalyst. The cross-linker, the structure of which is similar to those described previously, must diffuse through the water phase and into the siloxane phase where it can react with the silicone polymer. Addition-curing silicones in general are two-part systems that cure by the platinum-catalyzed reaction of a silicon hydride with typically a vinyl group attached to silicon. The basis for urethane chemistry is the reaction of an isocyanate group with a component containing an active hydrogen. The first step in formulating a urethane sealant is to prepare what is commonly called the prepolymer, typically by reaction of a hydroxy-terminated polyether with a stoichiometric amount of diisocyanate. Polysulfide sealants were the first high performance synthetic elastomeric sealants produce in the United States. The basic polymers are mercaptan-terminated (HS—R—H), with molecular weights ranging from 1000 to ca 8000.

There are two principal classes of acrylic sealants: latex acrylics and solvent-release acrylics. High molecular weight latex acrylic polymers are prepared by emulsion polymerization of alkyl esters of acrylic acid. Monomer, water, surfactants, and an initiator are mixed and polymerized until the acrylic monomer is depleted. Two types of monomers are used to vary polymer properties. High $T_g$ monomers such as methyl methacrylate and vinyl chloride improve durability and hydrophobicity, whereas polar-functional monomers such as hydroxyethyl acrylate are used to improve adhesion. The maximum levels of solids for the latex polymer is approximately 60%. In typical formulations, above this point the viscosity increases rapidly and the emulsion stability is poor. In relatively low solids (high water) content formulations, rather severe shrinkage occurs during cure. This can introduce stress and may be one of the reasons most latex acrylics are of lower performance and lower movement ability. The surfactants used are of special concern to sealant formulation because they can interfere with adhesion if improperly used. One approach to solve this problem is in corporate the surfactant into the polymer backbone during polymerization. This approach, which places the surfactant in an ideal location to stabilize the emulsion, does not allow the surfactant to migrate through the aqueous phase and interfere with adhesion because the surfactant is connected to the backbone (13). The emulsion polymers are compounded into sealants by adding fillers, plasticizers, freeze-thaw stabilizers, thickeners, and adhesions promoters. As is true of the silicone sealants, the acrylic sealants are easy to apply and clean with water.

Another class of acrylic sealants are the solvent-releasing acrylics. Acrylic monomers are polymerized in a solvent. The molecular weight of the polymer is lower than in the latex acrylics because of the inherently higher viscosity of the medium. However, the percentage of solids is approximately 80% vs the 60% common to latex acrylics. The natural adhesion of most of the solvent-releasing acrylics produces some of the best unprimed adhesion in the sealant industry. However, slow, continual cure generally produces large compression sets and limits their use to low movement application. Also, the relatively high amounts of solvent and traces of acrylic monomer in these functions limits their use to outdoor applications, usually in construction.

A typical one-part pigmented siliconized acrylic latex sealant will contain acrylic latex polymer (polymer and water), and optional ingredients selected from calcium carbonate, plasticizers, mineral spirits, propylene glycol, titanium dioxide, ammonium hydroxide, preservatives, surfactants, inorganic dispersants, organic dispersants, defoamers, associative thickener, and silane adhesion promoters, and mixtures thereof.

A typical one-part clear acrylic latex sealant formulation will contain acrylic latex polymer (polymer and water) and optional ingredients selected from plasticizers, fumed silica, surfactants, amino silanes, and ammonlium hydroxides and mixtures thereof Almost all sealants contain a mixture of a powdered filler incorporated into a viscous liquid, which results in a viscous sealant having a paste-like consistency.

In some embodiments formulations used as sealants and the components thereof (e.g., butylacrylate latex is known as AcryGen 4096D and is produced by GenCorp Performance Chemicals [Fitchburg, Mass.] and/or latex known as Rhoplex CS4000 and is produced by the Rohm and Haas Company [Philadelphia, Pa.]) may be used for construction application sealants and surface coatings in general and can be found in Winterowd, et.al. U.S. Pat. No. 6,608,131 which is incorporated by reference as if fully set forth herein.

Adhesives have been generally described in Kirk-Othmer-Adhesives; pg. 445-466; Vol. 1; 1991, by Aldophus Pocius, the disclosure of which is incorporated herein. An adhesive is a material capable of holding together solid materials by means of surface attachment. Adhesion is the physical attraction of the surface of one material for the surface of another. An adherend is the solid material to which the adhesive adheres and the adhesive bond or adhesive joint is the assembly made by joining adherends together by means of an adhesive. Practical adhesion is the physical strength of an adhesive bond. It primarily depends on the forces of the adhesive and the adherend, as well as the engineering of the adhesive bond. The interphase is the volume of materials in which the properties of one substance gradually change into the properties of another. The interphase is useful for describing the properties of an adhesive bonds. The interface, contained within the interphase, is the plane of contact between the surface of one material and the surface of another. Except in certain special cases, the interface is imaginary. It is useful in describing surface energetics.

Adhesive properties are often tested using various peel tests. In the simplest peel test, the T-peel test, the adherends are identical in size, shape, and thickness. Adherends are attached at their ends to a tensile testing machine and then separated in a "T" fashion. The temperature of the test, was well as the rate of adherend separation, is specified. The force required to open the adhesive bond is measured and the results are reported in terms of newtons per meter (pounds per inch, ppi). There are many other peel test configurations, each dependent upon the adhesive application. Such tests are well described in the ASTM literature.

A structural adhesive is a resin system, usually a thermoset, that is used to bond high strength materials in such a way that the bonded joint is able to bear a load in excess of 6.9 MPa (1,000 psi) at room temperature. Structural adhesives are the strongest form of adhesive and are meant to hold loads permanently. They exist in a number of forms. The most common form is the two-part adhesive, widely available as a consumer product. The next most familiar is that which is obtained as a room temperature curing liquid. Less common are primer-liquid adhesive combinations which cure at room temperature.

A pressure-sensitive adhesive, a material which adheres with no more than applied finger pressure, is aggressively and permanently tacky. It requires no activation other than the finger pressure, exerts a strong holding force, and should be removable from a smooth surface without leaving a residue. Pressure-sensitive adhesives are most widely used in the form of adhesive tapes. These tapes are used for an extraordinary number of applications: masking, medical application, electrical insulation, assembly, packaging, and other application. The application governs the choice of tape backing and the adhesive formulation. A transparent backing having relatively weak adhesive is used for paper mending; a filament filled backing having an aggressive adhesive is used for packaging applications. Pressure-sensitive adhesives are also obtainable in aerosol form for use in various graphics.

The general formula for a pressure-sensitive adhesive includes elastomeric polymer, a tackifying resin, any necessary fillers, various antioxidants and stabilizers, if needed, and cross-linking agents. In formulating a pressure-sensitive adhesive, a balance of three physical properties needs to be taken into account: sheer strength, peel strength, and tack. The shear strength or shear holding power of the adhesive is typically measured by hanging a weight on the end of a piece of tape and measuring the time of failure. Tack is the technical term applied to quantify the sticky feel of the material. in general, the shear strength and the tack of a pressure-sensitive adhesive increase and then go through a maximum as a function of the amount of tackifying resin added. The peel strength usually increases with the amount of tackifying resin. The shear holding power often depends upon the mode of crosslinking. This, a balance of properties appropriate to the application is obtained by controlling the rubber-to-resin ratio as well as the level and type of cross-linking agent.

The most widely used emulsion-based adhesives is that based upon poly(vinyl acetate)-poly(vinyl alcohol) copolymers formed by free-radical polymerization in an emulsion system. Poly(vinyl alcohol) is typically formed by hydrolysis of the poly(vinyl acetate). The properties of the emulsion are derived from the polymer employed in the polymerization as well as from the system used to emulsify the polymer in water. The emulsion is stabilized by a combination of a surfactant plus a colloid protection system. The protective colloids are similar to those used in paint to stabilize latex. For poly(vinyl acetate), the protective colloids are isolated from natural gums and cellulosic resins (carboxymethylcellouse or hydroxyethylcellous). The hydrolyzed polymer may also be used. The physical properties of the poly(vinyl acetate)polymer can be modified by changing the co-monomer used in polymerization. Any material which is free-radically active and participates in an emulsion polymerization may be employed. Plasticizers (qv), tackifiers, humectants, and other materials are often added to the adhesive to meet specifications for the intended application. Because the presence of foam in the bond line could decrease performance of the adhesion joint, agents that control the amount of air entrapped in an adhesive bond must be added. Biocides are also necessary: many of the materials that are used to stabilize poly (vinyl acetate) emulsions are natural products. Poly(vinyl acetate) adhesives known as "white glue" or "carpenter's glue" are available under a number of different trade names. Application are found mostly in the are of adhesion to paper and wood.

Elastomers: Elastomers have been generally described in Kirk-Othmer-Elastomers; pg. 905-1079; Vol. 8; 1993; and Kirk-Othmer-Elastomers; pg. 1-31; Vol. 9; 1994, by various authors, the disclosure of which is incorporated herein. The term elastomer is the modern word to describe a material that exhibits rubbery properties, i.e., that can recover most of its original dimensions after extension of compression. Once key class of elastomers is rubber materials. "Rubber materials, e.g., natural, SBR, or polybutadiene, being unsaturated hydrocarbons, are subjected to sulfur vulcanization, and this process requires certain ingredients in the rubber compound, besides the sulfur, e.g., accelerator, zinc oxide, and stearic acid. Accelerators are catalysts that accelerate the cross-linking reaction so that reaction time drops from many hours to perhaps 20-30 min. at about 130° C. In addition to the ingredients that play a role in the actual vulcanization process, there are other components that make up a typical rubber compound.

Softeners and extenders, generally inexpensive petroleum oils, help in the mastication and mixing of the compound. Antioxidants are necessary because the unsaturated rubbers can degrade rapidly unless protected from atmospheric oxygen. They are generally organic compounds of the amine or phenol type. Reinforcing fillers, e.g. carbon black or silica, can help enormously in strengthening the rubber against rapture or abrasion. Nonreinforcing fillers, e.g., clay or chalk, are used only as extenders and stiffeners to reduce cost.

For Styrene-Butadiene Rubber (SBR), the polymerization is carried out in an emulsion system where a mixture of the two monomers is mixed with a soap [or other surface active agent] solution containing the necessary catalysts (initiators). The final product is an emulsion of the copolymer, i.e., a fluid latex.

In some embodiments, elements used within an antimicrobial coatings as described herein is association with other applications or elsewhere herein (e.g., under the "Matrices" heading) may also be incorporated into a composition for architectural construction purposes including commercial and residential.

In some embodiments, an antimicrobial coating may be especially useful in the construction of a medical, medical research facility, or nursing home.

Marine Applications using Compositions Comprising Bridged Polycyclic Compounds

Embodiments described herein relate to coating compositions, to the use of such compositions in forming protective coatings on substrates, and to substrates bearing such coatings. Embodiments described herein relate more especially to the protection of substrates in aquatic environments, especially marine environments, and is concerned in particular with the provision of non-fouling protective coatings.

In some embodiments, non-fouling protective coatings may include antimicrobial coatings.

Man-made structures such as boat hulls, buoys, drilling platforms, oil production rigs, piers and pipes which are immersed in water are prone to fouling by aquatic organisms such as green and brown algae, barnacles, mussels and the like. Such structures are commonly of metal, but may also comprise other structural materials such as concrete, wood, synthetic materials, etc. This fouling is a nuisance on boat hulls, because it increases the frictional resistance towards movement through the water, with the consequence of reduced speeds and increased fuel costs. It is a nuisance on static structures such as the legs of drilling platforms and oil production rigs, firstly because the resistance of thick layers of fouling to waves and currents can cause unpredictable and potentially dangerous stresses in the structure, and, secondly, because fouling makes it difficult to inspect the structure for defects such as stress cracking and corrosion. It is a nuisance in pipes such as cooling water intakes and outlets, because the effective cross-sectional area is reduced by fouling, with the consequence of reduced flow rates. Fowling is a nuisance issue as relates to for example tools used in the water, for example nets or fishing rods, especially these items which are left at least partially submerged for long periods of time.

The commercially most successful methods of inhibiting fouling have involved the use of anti-fouling coatings containing substances toxic to aquatic life, for example tributyltin chloride or cuprous oxide. Such coatings, however, are being regarded with increasing disfavour because of the damaging effects such toxins can have if released into the aquatic environment. There is accordingly a need for non-fouling coatings which do not contain markedly toxic materials.

In some embodiments, antimicrobial coatings may inhibit the growth of a variety of organisms. Organisms which may be inhibited by antimicrobial coatings include, but are not limited to:

Fungi: *Aspergillus flavus, A. fumigalus, A. niger, Blastomyces dermatitidis, Candidas* pp., *Coccidioides immitis, Cryptococcus neoformans, Fusarium culmorum, Geotrichum* spp., *Histoplasma capsulatum, Malassezia furfur, Microsporum* spp., *Mucor racemosus, Nocardia* spp., *Paracoccidioides brasiliensis, Penicillium* spp., *Rhizopus higricans, Saccharomyces cerevisiae, Sporothrix schneckii, Torulopsis* spp., *Trichophyton* spp;

Bacteria: *Aerobacter aerongenes, Aeromonas hydrophila, Bacillus cereus, Bacillus subtilis, Bordetella pertussis, Borrelia burgdorferi, Campylobacter fetus, C. jejuni, Corynebacterium diphtheriae, C. bovis, Desulfovibrio desulfurica, Escherichia coli* 0157:H7, Enteropathogenic *E. coli*, Enterotoxin-producing *E. coli, Helicobacter pylori, Klebsiella pneumoniae, Legionella pneumophila, Leptospira interro-* gans, *Mycobacterium tuberculosis, M. bovis, Neisseria gonorrhoeae, N. meningitidis, Proteus mirabilis, P. vulgaris, Pseudomonas aeruginosa, Rhodococcus equi, Salmonella choleraesuis, S. enteridis, S. typhimurlum, S. typhosa, Shigella sonnei, S. dysenteriae, Staphylococcus aureus, S. epidermidis, Streptococcus anginosus, S. mutans, Vibrio cholerae, Yersinia pestis, Y. pseudotuberculosis, Actinomycetes, Stretomyces reubrireticuli, Streptoverticillium reticulum, Thermoactinomyces vulgaris;*

Viruses: Adenoviruses, Coronaviruses, Cytomegalovirus, Enteroviruses, Epstein-Barr virus, Herpes simplex virus, Hepatitis viruses, Human Immunodeficiency virus, Human Parvoviruses, Influenza viruses, Morbillivirus, Mumps virus, Norwalk viruses, Papillomaviruses, Paromyxovirus, Poxvirus, Rabies virus, Reoviruses, Rotaviruses, Rubella virus, Respiratory Synctial virus, Rhinoviruses, Varicella zoster virus;

Parasites: *Ancyclostoma braziliense, Anisakis, Babesia microti, Balantidum coli, Blastocystis hominis, Chilomastix mesnili, Cryptosporidium parvum, Cyclospora, Dientamoeba fragilis, Diphyllobothrium latum, Echinococcus granulosus, Entamoeba coli, E. histolytica, Enterocytozoon, Fasciola hepatica, Giardia lamblia, Iodamoeba butschlii, Isospora belli, Leishmania brasiliensis, L. donovani, L. tropica, Paragonimus westermani, Plasmodium vivax, Pnemocystis carinii, Sarcocytis hominis, Strongyloides stercoralis, Taenia solium, Toxoplasma gondii, Trichomonas vaginalis, Trichinella spiralis, Trypanosoma cruzi*; and Mollusks: mussels, clams, oysters, shellfish snails, bivalves, chitons, barnacles.

In some embodiments, elements used within an antimicrobial coatings as described herein is association with other applications or elsewhere herein (e.g., under the "Matrices" heading) may also be incorporated into a composition for marine applications for anti-fouling purposes.

Dental Compositions and Varnishes Comprising Bridged polycyclic Compounds

In prospering industrial societies, life expectancy steadily increases. At the same time, a drop in birth rate is observed. Both factors result in a change in age distribution characterized by a high proportion of elderly people.

In the field of dentistry, the increased average age of patients along with achievements regarding caries prophylaxis and treatment result in an increased average age of teeth which have to be cared for.

The prevention of caries and periodontitis can therefore not be limited to children and adolescents as the lifelong conservation of teeth demands a preventive approach also for middle-aged and elderly patients. Otherwise there is the risk that the positive results of early preventive measures will be lost within a few years ending up with tooth loss at old age.

Dental applications are challenging and require top performance from dental care providers and materials technology. Materials used in these applications need to be comfortable, hard, wear resistant, strong and yet also visibly appealing. Poorly formulated dental materials can result in discomfort, complications, and increased health care cost to consumers.

Demanding requirements such as those for dental materials also exist in numerous other products such as coatings. Recent developments in nanotechnology are increasingly being considered to address these requirements. A key challenge to widespread adoption of nanotechnology to such applications is the ability to manufacture non-agglomerated discrete nanoparticles that can be homogeneously distributed in resins or coatings to produce nanocomposites.

In some embodiments, a dental composition may include bridged polycyclic compounds. At least one of the bridged polycyclic compounds may include at least two cyclic groups. At least two of the cyclic groups may include quaternary ammonium or amine moieties. In some embodiments at least two of the cyclic groups may be defined at least in part by quaternary ammonium moieties.

In some embodiments, a composition may be applied to an oral surface or at least to a portion of an oral surface. An oral surface may include at least a portion of a dental fixture.

A method may include applying a dental composition to dental fixture such as bridges, caps, retainers, dentures and any temporary or permanent dental fixture in the oral cavity.

In some embodiments, a dental composition may include core-shell nanoparticles as described herein.

In some embodiments, a dental composition may include nanoparticles as described herein.

A dental composition and method of use of the same may be used in restoring the function and anatomy of a tooth. Dental compositions as described herein may be used in bonding agents, resin cements, sealants, varnishes, gels and resins. Dental compositions may include polymerizable unsaturated monomers, oligomers, prepolymers, or combinations thereof. Dental compositions may inhibit tooth decay and/or microbial growth in and around an oral cavity. Dental compositions may inhibit secondary decay.

Some commonly found bacteria leading to tooth decay have been known for some time (e.g. *Actinomyces israelii, A viscosus, A naeslundii, Arachnia propionica, Rothia dentocariosa, Bacterionema matruchotii*, and *Corynebacterium acnes*) as described by J. M Slack, et.al. in J. Dent. Res 50(1): 78-82, 1971, incorporated by reference as if set forth fully herein.

In some embodiments, dental compositions may enhance sustained antimicrobial activity with minimum harm to the living structure and surrounding tissues and without affecting the composition's restorative properties.

In some embodiments, dental compositions described herein may be used for oral trauma treatment. Dental composition may be used for oral trauma treatment field kits used for the temporary or permanent treatment of oral trauma out in the field when specialized help is not readily available (e.g., for a member of the armed services during maneuvers or times of war). Dental compositions may be used in combination with gelators, absorbents, and/or coagulating agents to prepare oral antimicrobial wound dressings.

Nanoparticles have been shown to enable nearly 50% reduction in filling shrinkage. These nanocomposites are suggested to be particularly useful for fabricating load bearing and cosmetic restorations. Examples of nanoparticles and general properties which they impart to dental compositions may be found in U.S. Pat. No. 6,593,395, which is incorporated by reference as if fully set forth herein.

A dental composite may have a high strength required for load-bearing restorations, yet maintains a glossy appearance, even after substantial wear. Through the use of particles having a mean particle size between about 0.05 .mu.m and about 0.50 micromolar, the composite is useful in stress bearing restorations and in cosmetic restorations. The structural filler used is typically ground to a mean particle size of less than 0.5 micromolar and also includes a nanofiller having discrete particles of a mean particle size less than 100 nm to improve handling and mechanical characteristics. The preferred dental composites maintain their surface finish even after substantial use and also have the strength properties of hybrid composite resins.

In some embodiments, a dental composite, comprising: a polymerizable resin base; and about 10% by volume to about 80% by volume filler consisting essentially of a ground structural filler and a non-ground nanofiller, wherein the ground structural filler comprises between about 10% by volume and about 70% by volume of the composite and consists of ground particles of mean particle size between about 0.05 .mu.m and about 0.50 .mu.m, and wherein the ground structural filler contains less than 50% by volume of particles above 0.5 .mu.m in diameter, and wherein the non-ground nanofiller comprises between about 1.0% by volume and about 15% by volume of the composite and consists essentially of discrete, non-aggregated gamma alumina particles having a mean particle size of about 40 nm or less.

The resin composite, in the cured form, may have a flexural strength of at least 100 MPa.

The resin composite, in the cured form, may have a flexural strength of at least 120 MPa.

The resin base comprises a polymerizable vinyl compound.

The the ground structural filler contains less than 10% by volume of particles above 0.8 .mu.m in diameter.

The the non-ground nanofiller comprises between about 5 and about 12% by volume of the composite.

The dental composite of claim 1, wherein the non-ground nanofiller has a refractive index in the range of about 1.48 to about 1.6.

A dental composite comprising: a polymerizable resin base; and about 11% by volume to about 80% by volume filler in the resin base, the filler consisting essentially of a ground structural filler and a non-ground nanofiller, wherein the ground structural filler comprises between about 10% by volume and about 70% by volume of the composite and consists of ground particles having a mean particle size of between about 0.05 .mu.m and about 0.50 .mu.m, and wherein the non-ground nanofiller comprises between about 1.0% by volume and about 15% by volume of the composite and consists essentially of discrete, non-aggregated aluminosilicate particles having a mean particle size of less than about 100 nm, and a 1:4 molar ratio of alumina to silica.

The resin composite, in the cured form, has a flexural strength of about 120 MPa or greater.

The resin base includes a polymerizable vinyl compound.

The non-ground nanofiller comprises between about 5% by volume to about 12% by volume of the composite.

The aluminosilicate particles have a mean particle size of about 80 nm.

The resin composite, in the cured form, has a flexural strength of at least 100 MPa.

The ground structural filler contains less than 10% by volume of particles above 0.8 .mu.m in diameter.

The non-ground nanofiller has a refractive index in the range of about 1.48 to about 1.6.

A dental composition may include a polymerizable compound, a polymerization initiator system, bridged polycyclic compounds, or combinations thereof. These compositions may be suitable for restoring the functionality and anatomy of a damaged tooth. Uses may include, but are not limited to, use as dental primers, adhesives, surface sealants, liners, luting cements, varnishes, impression materials, equipment and impression systems, and composite restoratives. Uses may include, but are not limited to, impression materials, coatings for impression trays, and impression systems. In some embodiments, dental compositions may impart antimicrobial activity to a contacted tooth structure and/or surrounding tissue.

The present dental compositions may include a polymerizable compound (e.g., at least one polymerizable monomer or prepolymer selected from those known in the art of dental materials) including, but not limited to, polymerizable amides, esters, alkenes, imides, acrylates, methacrylates, urethanes, vinyl esters or epoxy-based materials. Other polymerizable compounds may include those based on styrene, styrene acrylonitrilic, sulfones, acetals, carbonates, phenylene ethers, phenylene sulfides, or other polymerizable units listed herein. Examples of dental compositions and additives typically used may be found in U.S. Pat. No. 6,326,417, which is incorporated by reference as if fully set forth herein. Examples of dental compositions and additives typically used may be found in U.S. Pat. and patent application Ser. Nos. U.s. Pat. Nos. 6,500,004; 6,326,417; 20010009931; 20050252413; and 20030134933 (acidic based sealants) which are incorporated by reference as if fully set forth herein.

Polymerizable compounds may include ethylenically unsaturated monomers and prepolymers and include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Wakline, which are incorporated by reference as if fully set forth herein. Methacrylate-based monomers may be used (e.g., condensation product of bisphenol A and glycidyl methacrylate, 2,2'-bis [4-(3-methacryloxy-2-hydroxy propoxy)-phenyl]-propane ("BIS-GMA"), dipentaerythritol pentaacrylate (DPEPA), pentaerythritol dimethacrylate (PEDM), the condensation product of ethoxylated bisphenol A and glycidyl methacrylate ("EBPA-DMA"), and the condensation product of 2 parts hydroxymethylmethacrylate and 1 part triethylene glycol bis(chloroformate) ("PCDMA")). Polymerizable compounds may include polyurethane-based dimethacrylates ("PUDMA").

Polymerizable compounds may include polymerizable diluent monomers. Such monomers are generally used to adjust the viscosity of a polymerizable composition. Suitable methacrylate-based diluent monomers may include, but are not limited to, hydroxyalkyl methacrylates (e.g., 2-hydroxyethyl methacrylate, 1,6-hexanediol dimethacrylate, and 2-hydroxypropyl methacrylate); glyceryl dimethacrylate; and ethyleneglycol methacrylates (e.g., ethyleneglycol methacrylate, diethyleneglycol methacrylate, triethyleneglycol methacrylate, Triethyleneglycol dimethacrylate, and tetraethyleneglycol methacrylate).

When used as primers, adhesives, or primer/adhesive, dental compositions may include a polymerizable compound including hydrophilic polymerizable monomers to enhance the bonding characteristics of the dental composition. Suitable polymerizable hydrophilic monomers may have carboxyl, phosphoryl, sulfonyl, and/or hydroxyl functional groups. Examples of polymerizable hydrophilic monomers having at least one carboxyl group may include, but are not limited to, methacrylic acid, maleic acid p-vinylbenzoic acid, 11-methacryloyloxy-1,1-undecanedicarboxylic acid, 1,4-dimethacryloyloxyethylpyromellitic acid, 6-methacryloyloxyethylnaphthalene-1,2,6-tricarboxylic acid, 4-methacryloyloxymethyltrimellitic acid and the anhydride thereof, 4-methacryloyloxyethyltrimellitic acid ("4-MET") and an anhydride thereof ("4-META"), 4-(2-hydroxy-3-methacryloyloxy)butyltrimellitic acid and an anhydride thereof, 2,3-bis(3,4-dicarboxybenzoyloxy)propyl methacrylate, methacryloyloxytyrosine, N-methacryloyloxytyrosine, N-methacryloyloxyphenylalanine, methacryloyl-p-aminobenzoic acid, an adduct of 2-hydroxyethyl methacrylate with pyromellitic dianhydride (PMDM), and an adduct of 2-hydroxyethyl methacrylate with 3,3',4,4'-benzophenonetetracarboxylic dianhydride (BTDA) or 3,3',4,4'-biphenyltetracarboxylic dianhydride. Hydrophilic monomers may include BPDM, the reaction product of an aromatic dianhydride with an excess of 2-HEMA (2-hydroxyethyl methacrylate), as disclosed in U.S. Pat. No. 5,348,988, which are incorporated by reference as if fully set forth herein. Other hydrophilic monomers may include EDMT, the reaction product of 2-hydroxyethyl methacrylate ("2-HEMA") with ethylene glycol bistrimellitate dianhydride; DSDM, the reaction product of 3,3',4,4'-diphenylsulfone tetracarboxylic dianhydride and 2-HEMA; PMDM, and PMGDM, the adduct of pyromellitic dianhydride with glycerol dimethacrylate.

Examples of polymerizable compounds having at least one phosphoric acid group may include, but are not limited to 2-methacryloyloxyethyl acidophosphate, 2-methacryloyloxypropyl acidophosphate, 4-methacryloyloxybutyl acidophosphate, 8-methacryloyloxyoctyl acidophosphate, 10-methacryloyloxydecyl acidophosphate, bis(2-methacryloyloxyethyl)acidophosphate, and 2 methacryloyloxyethylphenyl acidophosphate. The phosphoric acid group in these compounds may be replaced with a thiophosphoric acid group. Examples of polymerizable compounds may include 2-methacryloyloxyethylphenyl acidophosphate and 10-methacryloyloxydecyl acidophosphate. Examples of polymerizable monomers having at least one sulfonic acid group include 2-sulfoethyl methacrylate, 3-sulfo-2-butyl methacrylate, 3-bromo-2-sulfo-2-propyl methacrylate, 3-methoxy-1-sulfo-2-propyl methacrylate, and 1,1-dimethyl-2-sulfoethyl methacrylamide.

All the above polymerizable monomers may be used alone or in combination.

A dental composition may include a polymerization initiator system, including light curing, self-curing, dual curing, and vacuum, heat, and pressure curing systems as well as any combination thereof. Visible light curing systems employ light-sensitive compounds (e.g., benzil diketones and DL-camphorquinone) in amounts ranging from about 0.05 to 0.5 weight percent. Visible light curing systems may include polymerization accelerators (e.g., various organic tertiary amines well known in the art). In visible light curable compositions, the tertiary amines are generally acrylate derivatives such as dimethylaminoethyl methacrylate and, particularly, diethylaminoethyl methacrylate ("DEAME") in amounts in the range from about 0.05 to 0.5 weight percent.

Self-curing compositions may contain free radical polymerization initiators such as, for example, peroxides in amounts ranging from about 2 to 6 weight percent. Suitable free radical initiators may include lauryl peroxide, tributyl hydroperoxide, cumene hydroperoxide, and benzoyl peroxide. The heat and pressure curable systems also include heat cure initiators such as aromatic sulfinic acids and salts thereof, benzoyl peroxide, 1,1'-azobis (cyclohexanecarbonitrile), or other free radical initiators. Polymerization accelerators commonly used with these include tertiary amines, generally aromatic tertiary amines such as ethyl 4-(N,N-dimethyl)aminobenzoate ("EDAB"), dimethyl-p-toluidine, dihydroxyethyl-p-toluidine and the like, in amounts ranging from about 0.05 to about 4.0 weight percent.

The dental restorative compositions may also comprise other additives and solvents known in the art, for example, ultraviolet light absorbers, anti-oxidants such as BHT, stabilizers, fillers, pigments, opacifiers, handling agents, and others. An ultraviolet absorber may be employed in amounts ranging from about 0.05 to about 5.0 weight percent. Such ultraviolet absorbers may be desirable in the visible light curable compositions in order to avoid discoloration of the resin from any incident ultraviolet light. Suitable ultraviolet absorbers may include gelators, various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y.

Fillers, such as colloidal silica, barium glasses, fibrous fillers, quartz, ceramic fillers and the like may also be incorporated into dental compositions, particularly when they are to be used as bonding agents, luting cements or filling composites. Suitable fillers may include fillers conventionally used in the dental industry capable of being covalently bonded to the resin matrix itself or to a coupling agent which is covalently bonded to both. Silane coupling agents are known, for example methacryloxypropyl trimethoxy silane. Such fillers are described in U.S. Pat. Nos. 4,544,359 and 4,547,531, which is incorporated by reference as if fully set forth herein. Examples of suitable filling materials may include, but are not limited to, amorphous silica, spherical silica, colloidal silica, barium glasses, quartz, ceramic fillers, silicate glass, hydroxyapatite, calcium carbonate, fluoroaluminosilicate, barium sulfate, quartz, barium silicate, strontium silicate, barium borosilicate, barium boroaluminosilicate, strontium borosilicate, strontium boroaluminosilicate, glass fibers, lithium silicate, ammoniated calcium phosphate, deammoniated calcium phosphate, alumina, zirconia, tin oxide, polymer powders, polymethyl methacrylate, polystyrene, and polyvinyl chloride, titania, and combinations thereof. Particularly suitable fillers for dental filling-type materials prepared are those having a particle size in the range from about 0.1 to about 5.0 microns, together with a silicate colloid having particle sizes in the range from about 0.001 to about 0.07 microns.

Antimicrobials may be generally effective against organisms which cause secondary decay, and must not adversely affect the required physical properties of the cured compositions, in particular water sorption, diametral tensile strength, and hardness. In particular, the ADA specification No. 27 requires dental resin composites to have water sorption values below 50 $\mu g/mm^3$/week. Commercial dental restorative materials used as, filling materials preferably have water sorption values of less than about 30, less than about 20, or less than about 15 $\mu g/mm^3$/week. The ADA specification No. 27 specifies that the diametral tensile strength for filled dental composite (type II) should be a minimum of 34 MPa. Commercial dental restorative materials used as filling materials may have DTS values of greater than about 38, greater than about 40, or greater than about 45 MPa. Dentine bonding strength must be at least about 10 MPa, at least about 15 MPa, at least about 18 MPA, or at least about 20 MPa.

Dental compositions may be used as bonding primers or adhesives. When dental compositions are to be used as bonding primers, adhesives, or primer/adhesives, volatile solvents such as water, alcohol, acetone, and the like are used to dilute the polymerizable compound(s). The particular amounts of polymerizable compound(s) and solvent may be adjusted so as to provide sufficient viscosity such that they can be applied in one or a relatively few number of coats and achieve a uniform thin coating, of the dental substrate, while providing high bonding strengths between the dental substrate and the restorative material or dental component. Optionally, additional polymerizable compounds, optional self-life stabilizers, or other modifying ingredients known in the art may be incorporated.

Dental compositions may be used as a bonding agent and/or base liner under restorative materials such as resin composites, silver amalgam alloys, and the like.

The most common ailments seen by vets in dogs and cats are dental problems. More than half of all pets suffer from gum disease, dental calculus or similar dental problems.

Calculus is the brown build-up of plaque found extending downwards on the tooth from the gum line. Calculus is a haven for bacteria which can have serious consequences for your pet's general health. These bacteria can not only cause abscesses and tooth loss but can have effects further afield—even resulting in organ damage as the bacteria are carried from the mouth, through the bloodstream.

All types of teeth and gum diseases can lead to serious health problems in pets. Dogs and cats make much fuller use of their teeth than humans do—using them in ways humans usually use their hands. For this reason, toothache, dental disease and loss of teeth can all have serious consequences for pets. Damage to the teeth and gums in pets is permanent and irreversible.

In some embodiments this antimicrobial may be incorporated into pet dental systems for plaque prevention (e.g. OraVet™ a clinically provided plaque prevention system [Merial, Duluth, Ga.]). A system featuring a dental barrier sealant and a plaque prevention gel that can significantly reduces the formation of plaque and calculus, two factors in the onset of periodontal disease.

Dental compositions may be used as dental luting cements and/or cavity filling materials.

In some embodiments, elements used within an antimicrobial coatings as described herein is association with other applications or elsewhere herein (e.g., under the "Matrices" heading) may also be incorporated into a composition for dental purposes.

Medical Device Applications using Compositions Comprising Bridged polycyclic Compounds Medical devices used for patient treatment can be a source of microbial (bacterial or fungal) infection in such patients. For example, insertion or implantation of a catheter into a patient can introduce microbes and/or, when left in place for prolonged periods of time, permit the introduction of microbes during long-term exposure of the catheter exit site to the environment. In addition, long-term catheter use often produces a biofilm on the catheter surface, which facilitates the development of infection that can cause patient discomfort and compromise patient health.

Medical devices are any article that contacts patients or are used in health care, and may be for use either internally or externally. The medical devices can be made from a variety of natural or synthetic materials, such as, for example, latex, polystyrene, polyester, polyvinylchloride, polyurethane, ABS polymers, polyamide, polyimide, polycarbonate, polyacrylates, polyethylene, polypropylene, synthetic rubber, stainless steel, ceramics such as aluminum oxide and glass, and silicone.

Illustrative, non-limiting, examples include of medical devices include, but are not limited to, cannulae, catheters, condoms, contact lenses, endotracheal and gastroenteric feeding tubes as well as other tubes, grafts, guide wires, implant devices, IUDs, medical gloves, oxygenator and kidney membranes, pacemaker leads, peristaltic pump chambers, shunts, stents and sutures Other non-limiting examples of medical devices include peripherally insertable central venous catheters, dialysis catheters, long term tunneled centrral venous catheters, long term non-tunneled central venous catheters, peripheral venous catheters, short-term central venous catheters, arterial catheters, pulmonary artery Swan-Ganz catheters, urinary catheters, artificial urinary sphincters, long term urinary devices, urinary dilators, urinary stents, other urinary devices, tissue bonding urinary devices, penile prostheses, vascular grafts, vascular catheter ports, vascular dilators, extravascular dilators, vascular stents, extravascular stents, wound drain tubes, hydrocephalus shunts, ventricular catheters, peritoneal catheters, pacemaker systems, small or temporary joint replacements, heart valves, cardiac assist devices and the like and bone prosthesis, joint prosthesis and dental prosthesis.

In some embodiments, antimicrobial compositions useful for forming a coating may be supplied in the form of a kit comprising the compositions to coat various medical devices (e.g., catheters) prior to use. These kits may be readily prepared by utilizing standard preparations of antimicrobial solutions, which are readily known and applied in the art. The compositions used in the kit may be in the following forms, but are not limited to these forms, creams, capsules, gels, pastes, powders, liquids and particles.

It is also contemplated that a kit may comprise a medical device that has been pre-coated with an antimicrobial agent and compositions to coat the medical device prior to implantation into a mammal. Thus, the medical staff only needs to apply the antimicrobial composition to the medical device prior to implantation. One realizes that a kit containing a pre-coated medical device will reduce the amount of time that is needed for the implantation.

A further embodiment is a kit comprising compositions to coat the surfaces of medical devices prior to implantation into a mammal comprising an antimicrobial composition as described in various emodiments herein.

In some embodiments, elements used within an antimicrobial coatings as described herein is association with other applications or elsewhere herein (e.g., under the "Matrices" heading) may also be incorporated into a composition for medical device coatings.

Personal Care Applications using Compositions Comprising Bridged polycyclic Compounds In October 2000, the first known outbreak of *Mycobacterium fortuitum* cutaneous infections acquired from whirlpool footbaths, also called footspas, was investigated at a nail salon in northern California. Over 100 pedicure customers had prolonged boils on the lower legs that left scars when healed. In the investigation, the area behind the screen of the recirculation inlet in each of 10 footspas at the nail salon was swabbed and recovered strains of *M. fortuitum* from all 10. Isolates from 3 footbaths and 14 patients were indistinguishable by pulsed-field gel electrophoresis and by multilocus enzyme electrophoresis.

Before this outbreak, *M. fortuitum* and other rapidly growing mycobacteria (RGM) caused localized cutaneous infections but usually in a healthcare-associated setting with surgical or clinical devices contaminated with water from the hospital or from the municipal water system. In the nail salon outbreak, it was suspected that the mycobacteria entered the footspas through the municipal tap water and thrived in the large amount of organic debris accumulated behind the footspa recirculation screens. However, cultures of tap water at that nail salon later in the investigation yielded RGM in the *M. chelonae*-abscessus group but not *M. fortuitum*.

Since RGM are commonly found in municipal water systems, and since the nail care business is a $6 billion and growing industry in this country, it was hypothesized that similar whirlpool footbath-associated RGM infections occurred sporadically but went unnoticed. Soon after the health communities were alerted to this outbreak, 3 cases of lower extremity RGM infections associated with 2 different nail salons were documented from southern California.

Little has been published on the prevalence of mycobacteria in whirlpool footbaths. To determine the prevalence of nontuberculous mycobacteria in this common nail salon equipment, a mycobacteriologic survey of footspas in nail salons in California was conducted from November to December 2000.

Mycobacteria were isolated from virtually all pedicure spas surveyed, the sole exception being the footspa that had only been in service for 11 days. Mycobacteria were recovered whether or not disinfectants were reportedly used and whether or not debris was visible behind the recirculation screen. Addtionally the recirculation screen was found to have the highest level of overall bacteria. Likely due to the continued exposure to the bulk water for the recirculation process. In some embodiments an antimicrobial coating is applied to the recirculation screen and/or other components of the jet by the manufacturer and/or as part of the routine cleaning process of the pedicure or whirlpool bath maintence between customers. As both pipe (interior and exterior pipe systems as decribed by B. Munde in U.S. Pat. No. 5,230,842, which is incorporated by reference as if fully set forth herein)

pipeless (U.S. Pat. Nos. 4,853,987; 5,414,878; 5,587,023, which are incorporated by reference as if fully set forth herein) and traditional foot baths have propellers, screens and jets, the coating can be used for any pedicure bath system and all components.

RGM, *M. fortuitum* in particular, were the most frequently isolated mycobacteria. The survey suggests that potentially pathogenic mycobacteria are widespread in these footspas across California. These organisms most likely were introduced into the footspas through the municipal water supply, where they colonized parts of the spas and probably the plumbing. Given that these whirlpool footbaths are widespread in California but similar infections known to date are rare, the presence of such mycobacteria alone may not be sufficient to cause pedicure customers to get cutaneous infections from using these spas. The 2000 outbreak investigation noted an unusually large amount of debris behind the footspa recirculation screens, which might have provided a niche for mycobacteria to colonize and proliferate to large numbers. In that outbreak, customers who shaved their legs before using these implicated footspas were at higher risk for furunculosis than those who did not. However, some customers in that outbreak were infected even though they reportedly did not shave their legs before using the pedicure spas. Thus, while the widespread presence of potentially pathogenic mycobacteria in footspas has been documented, the risk for infection remains unclear.

Nonetheless, the findings documented the ubiquitous presence of potentially pathogenic mycobacteria among footspas of nail salons in California. The 2000 outbreak might have been a warning of what may happen again if this emerging infection is not adequately addressed. In 2004, a case report documented 2 cases of *M. mageritense* furunculosis associated with using footbaths at a nail salon in Georgia.

The California Board of Barbering and Cosmetology adopted new regulations in May 2001 requiring nail salons to follow specific cleaning and disinfection procedures to ensure that their footspa equipment is properly cleaned and maintained.

In some embodiments, compositions comprising bridged polycyclic compounds may be used to form antimicrobial coatings on devices and systems associated with personal care and/or personal care facilities (e.g., nail and/or hair salons). Examples of personal care items include, but are not limited to, footbaths, footspas, scissors, cuticle files, clippers, etc.

Portions of personal care devices may be treated by the manufacturer during production with an antimicrobial coating (e.g., the filter screen of a water pump in a footbath) and/or an end user of the device may treat the portion themselves. In some embodiments, an end user may purchase a kit to treat a personal care device or a portion of it. Kit are described in more detail in the Medical Device section herein.

In some embodiments a pedicure tub liner (as described by F. Sherif, et.al. in patent application U.S. 20040199994 which is incorporated by reference as if fully set forth herein) may be treated by the manufacturer or the personal care professional with antimicrobial coating In some embodiments, elements used within an antimicrobial coatings as described herein is association with other applications or elsewhere herein (e.g., under the "Matrices" heading) may also be incorporated into a composition for coating a portion of a personal care article or device.

EXAMPLES

Having now described the invention, the same will be more readily understood through reference to the following example(s), which are provided by way of illustration, and are not intended to be limiting of the present invention.

General Experimental: All manipulations were carried out using Schlenk technique under nitrogen atmosphere. Ethyl alcohol, denatured, reagent grade, anhydrous, was purchased from EMD. Dimethylformamide (DMF), 99.8%, anhydrous, was purchased from Acros Organics. Both were used without further purification. Tris(2-aminoethyl)amine, 1-bromohexane, 1-bromooctane, 1-bromodecane, 1-bromododecane, 1-bromohexadecane, 1-bromobutane, benzylbromide and methyliodide were purchased from Acros Organics and distilled before use. Terephthaldicarboxaldehyde was purchased from Acros Organics and sublimed before use. Sodium borohydride and sodium carbonate were purchased from Acros Organics and used without further purification. NMR analysis was performed on a JEOL Eclipse$^+$ 400 instrument.

Synthesis of Several Examples of Bridged Polycyclic Compounds:

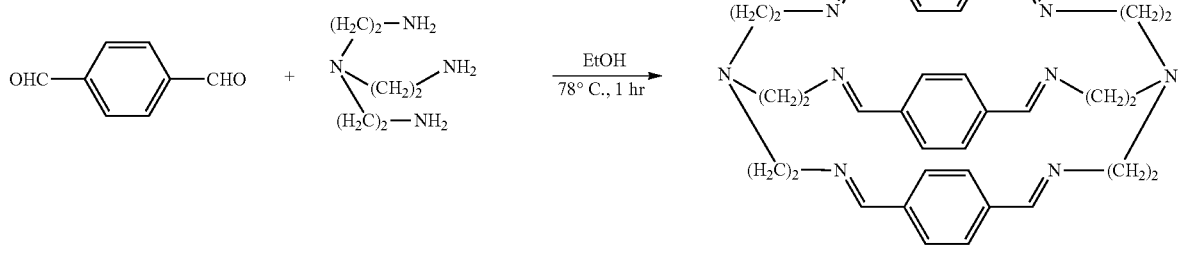

202

NaBH$_4$/RT/14 hr

-continued

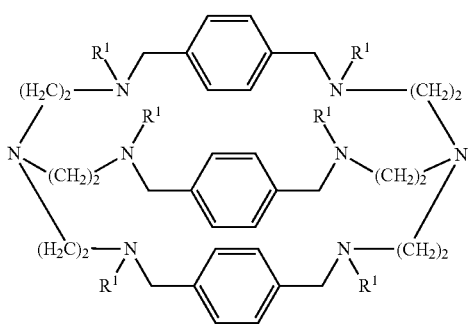

206

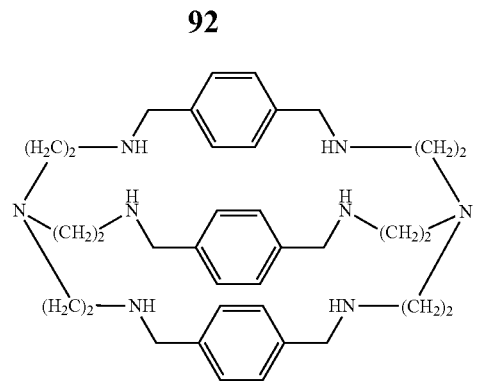

204

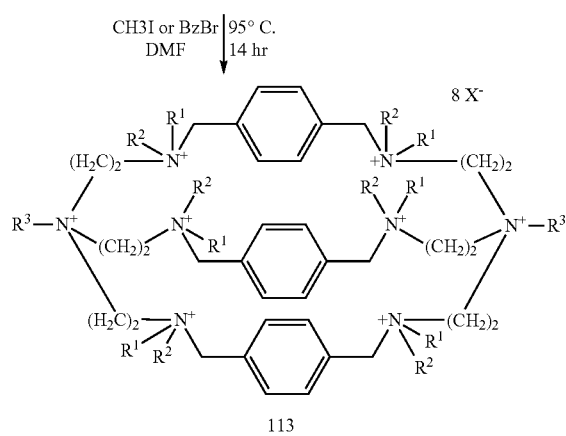

113

Where: 206a and 113a are $R^1 = C_6H_{13}$, $R^2 = CH_3$ and $R^3 = R^1$ or $R^2$
206b and 113b are $R^1 = C_8H_{17}$, $R^2 = CH_3$ and $R^3 = R^1$ or $R^2$
206c and 113c are $R^1 = C_{10}H_{21}$, $R^2 = CH_3$ and $R^3 = R^1$ or $R^2$
206d and 113d are $R^1 = C_{12}H_{25}$, $R^2 = CH_3$ and $R^3 = R^1$ or $R^2$
113e is $R^1 = C_6H_{13}$, $R^2 = CH_2Ph$ and $R^3 = R^1$ or $R^2$
113f is $R^1 = C_{12}H_{25}$, $R^2 = CH_2Ph$ and $R^3 = R^1$ or $R^2$
206h and 113h is $R^1 = C_4H_9$, $R^2 = CH_3$ and $R^3 = R^1$ or $R^2$
206g is $R^1 = C_6H_{13}$ Synthesis of 202 and 204: To a 3000 mL, 3-neck round bottom flask was added terephthaldicarboxaldehyde (16.1 g, 120 mmoles) and the flask fitted with a reflux condenser, addition funnel and thermocouple. Then ethyl alcohol (2000 mL) was added and the temperature controller set to 78 °C. About 10 minutes after the reaction solution temperature reached 78 °C., tris(2-aminoethyl)amine (11.7 g, 12.0 mL, 80.0 moles) was added by syringe. After about 1 h the heat was removed and the reaction solution allowed to cool. When the reaction solution temperature dropped below 35 °C., sodium borohydride (9.08 g, 240 mmoles) was added and the reaction solution stirred for about 14 h at room temperature. Analysis of intermediate 202 was obtained by isolation of a sample of the reaction solution before sodium borohydride addition. Work up of 204: The reaction solution was filtered and the volatiles were removed by vacuum transfer. Then 1.0 M NaOH (250 mL) and dichloromethane (150 mL) were added. After mixing the phases were separated and the aqueous layer was extracted with dichloromethane (2×75 mL). The organic was combined, washed with water (2×100 mL), dried over sodium sulfate and the volatiles removed to leave the product as a white slightly waxy powder (22.1 g, 36.9 mmoles, 92.3% yield). Analysis of 202: $^1$H NMR (400 MHz, $CD_2Cl_2$, δ): 2.74, 3.73 (s, 24H, $NCH_2CH_2NCHC_6H_4$), 7.15 (s, 12H, $NCH_2CH_2NCHC_6H_4$), 8.12 (s, 6H, $NCH_2CH_2NCHC_6H_4$). ESI-MS (m/z): $[M+H]^+$ 587. Analysis of 204: $^1$H NMR (400 MHz, $CD_2Cl_2$, δ): 2.61, 2.76 (m, 24H, $NCH_2CH_2NHCH_2C_6H_4$), 3.62 (s, 12H, $NCH_2CH_2NHCH_2C_6H4$), 6.84 (s, 12H, $NCH_2CH_2NHCH_2C_6H_4$). ESI-MS (m/z): $[M+H]^+$ 599.

Synthesis of 206a: To a 100 mL flask was added 204 (8.00 g, 13.4 mmoles) and ethyl alcohol (8.4 mL). Upon stirring for about an hour sodium carbonate (9.37 g, 88.2 mmoles) was added followed by 1-bromohexane (14.6 g, 12.4 mL, 88.2 mmoles) and the reaction flask fitted with a reflux condenser. The solution was refluxed on a thermostat controlled oil bath set to 95 °C. for about 14 h. Then the heat was removed and the reaction solution was cooled to room temperature. Work Up of 206a: The volatiles were removed by vacuum transfer, then the crude product was combined with 1.0 M NaOH (150 mL) and dichloromethane (50 mL). The phases were separated and the aqueous extracted with dichloromethane (2×50 mL). The organic phases were combined, washed with water (2×50 mL), dried over sodium sulfate and the volatiles removed to leave a light greenish-yellow oil (13.5 g, 12.2 mmoles, 91.3% yield). Analysis of 206a: $^1$H NMR (400 MHz, $CD_2Cl_2$, δ): 0.83-0.93 (m, 18H, $N\{CH_2CH_2N[CH_2(CH_2)_4CH_3]CH_2C_6H_4CH_2N[CH_2(CH_2)_4CH_3]CH_2CH_2\}_3N$), 1.19-1.46 (m, 48H, $N\{CH_2CH_2N[CH_2$ (CH$_2$)$_4$CH$_3$]CH$_2$C$_6$H$_4$CH$_2$N[CH$_2$(CH$_2$)$_4$CH$_3$]CH$_2$CH$_2$}$_3$N), 2.28-2.54 (m, 36H, N{CH$_2$CH$_2$N[CH$_2$(CH$_2$)$_4$CH$_3$]CH$_2$C$_6$H$_4$CH$_2$N[CH$_2$(CH$_2$)$_4$CH$_3$]CH$_2$CH$_2$}$_3$N), 3.28-3.64 (m, 12H, N{CH$_2$CH$_2$N[CH$_2$(CH$_2$)$_4$CH$_3$]CH$_2$C$_6$H$_4$CH$_2$N[CH$_2$(CH$_2$)$_4$CH$_3$]CH$_2$CH$_2$}$_3$N), 7.00-7.35 (m, 12H, N{CH$_2$CH$_2$N[CH$_2$(CH$_2$)$_4$CH$_3$]CH$_2$C$_6$H$_4$CH$_2$N[CH$_2$(CH$_2$)$_4$CH$_3$]CH$_2$CH$_2$}$_3$N). ESI-MS (m/z): [M+H]$^+$ 1104.

Synthesis of 113a: To the flask containing the product 206a (13.5 g, 12.2 mmoles) was added DMF (240 mL). Then methyl iodide (17.3 g, 7.60 ml, 122 mmoles) was added and the reaction solution was heated with a thermostat controlled oil bath set to 70 °C. After being heated for about 14 h, the heat was removed and the reaction solution cooled to room temperature. Work Up of 113a: The solution was divided between two 1000 mL flasks and ethyl acetate (770 mL) was added to each flask and the solution stirred for 1 h. Then the supernatant was removed by filtration. The precipitate was washed with ethyl acetate (3×60 mL) and the volatiles were removed by vacuum transfer leaving an off white powder (24.4 g, 10.9 mmoles, 89.3% yield). Analysis of 113a: $^1$H NMR (400 MHz, DMF-d$_7$, δ): 0.81-0.84 (m, 18H, CH$_3$N{CH$_2$CH$_2$N[CH$_2$(CH$_2$)$_4$CH$_3$](CH$_3$)CH$_2$C$_6$H$_4$CH$_2$N[CH$_2$(CH$_2$)$_4$CH$_3$](CH$_3$)CH$_2$CH$_2$}$_3$NCH$_3$), 1.20-2.10 (m, 48H, CH$_3$N{CH$_2$CH$_2$N[CH$_2$(CH$_2$)$_4$CH$_3$](CH$_3$)CH$_2$C$_6$H$_4$CH$_2$N[CH$_2$(CH$_2$)$_4$CH$_3$](CH$_3$)CH$_2$CH$_2$}$_3$NCH$_3$), 3.05-4.05 (m, 54H, CH$_3$N{CH$_2$CH$_2$N[CH$_2$(CH$_2$)$_4$CH$_3$](CH$_3$)CH$_2$C$_6$H$_4$CH$_2$N[CH$_2$(CH$_2$)$_4$CH$_3$](CH$_3$)CH$_2$CH$_2$}$_3$NCH$_3$), 4.40-5.20 (m, 18H, CH$_3$N{CH$_2$CH$_2$N[CH$_2$(CH$_2$)$_4$CH$_3$](CH$_3$)CH$_2$C$_6$H$_4$CH$_2$N[CH$_2$(CH$_2$)$_4$CH$_3$](CH$_3$)CH$_2$CH$_2$}$_3$NCH$_3$), 7.50-8.15 (m, 12H, CH$_3$N{CH$_2$CH$_2$N[CH$_2$(CH$_2$)$_4$CH$_3$](CH$_3$)CH$_2$C$_6$H$_4$CH$_2$N[CH$_2$(CH$_2$)$_4$CH$_3$](CH$_3$)CH$_2$CH$_2$}$_3$NCH$_3$). ESI-MS (m/z): [M-I]$^+$ 2111, [M-2I]$^{2+}$ 992, [M-Me-2I]$^+$ 1971.

Synthesis of 206b: Using the procedure for synthesis of 206a with 1-bromooctane in place of 1-bromohexane produced 206b in 96.9% yield. Analysis of 206b: $^1$H NMR (400 MHz, CD$_2$Cl$_2$, δ): 0.83-0.89 (m, 18H, N{CH$_2$CH$_2$N[CH$_2$(CH$_2$)$_6$CH$_3$]CH$_2$C$_6$H$_4$CH$_2$N[CH$_2$(CH$_2$)$_6$CH$_3$]CH$_2$CH$_2$}$_3$N), 1.23-1.43 (m, 72H, N{CH$_2$CH$_2$N[CH$_2$(CH$_2$)$_6$CH$_3$]CH$_2$C$_6$H$_4$CH$_2$N[CH$_2$(CH$_2$)$_6$CH$_3$]CH$_2$CH$_2$}$_3$N), 2.28-2.54 (m, 36H, N{CH2CH$_2$N[CH$_2$(CH$_2$)$_6$CH$_3$]CH$_2$C$_6$H$_4$CH$_2$N[CH$_2$(CH$_2$)$_6$CH$_3$]CH$_2$CH$_2$}$_3$N), 3.28-3.63 (m, 12H, N{CH$_2$CH$_2$N[CH$_2$(CH$_2$)$_6$CH$_3$]CH$_2$C$_6$H$_4$CH$_2$N[CH$_2$(CH$_2$)$_6$CH$_3$]CH$_2$CH$_2$}$_3$N), 7.00-7.35 (m, 12H, N{CH$_2$CH$_2$N[CH$_2$(CH$_2$)$_6$CH$_3$]CH$_2$C$_6$H$_4$CH$_2$N[CH$_2$(CH$_2$)$_6$CH$_3$]CH$_2$CH$_2$}$_3$N). ESI-MS (m/z): [M+H]$^+$ 1272.

Synthesis of 113b: Using the procedure for synthesis for 113a with 206b in place of 206a produced 113b in 76.8% yield. Analysis of 113b: ESI-MS (m/z): [M-I]$^+$ 2280, [M-2I]$^{2+}$ 1076, [M-Me-2I]$^+$ 2139.

Synthesis of 206c: Using the procedure for synthesis of 206a with 1-bromodecane in place of 1-bromohexane produced 206c in 96.2% yield. Analysis of 206c: $^1$H NMR (400 MHz, CD$_2$Cl$_2$, δ): 0.85-0.89 (m, 18H, N{CH$_2$CH$_2$N[CH$_2$(CH$_2$)$_8$CH$_3$]CH$_2$CAHCH$_2$N[CH$_2$(CH$_2$)$_8$CH$_3$]CH$_2$CH$_2$}$^3$N), 1.24-1.44 (m, 96H, N{CH$_2$CH$_2$N[CH$_2$(CH$_2$)$_8$CH$_3$]CH$_2$C$_6$H$_4$CH$_2$N[CH$_2$(CH$_2$)$_8$CH$_3$]CH$_2$CH$_2$}$_3$N), 2.29-2.56 (m, 36H, N{CH$_2$CH$_2$N[CH$_2$(CH$_2$)$_8$CH$_3$]CH$_2$C$_6$H$_4$CH,N[CH$_2$(CH$_2$)$_8$CH$_3$]CH$_2$CH$_2$}$_3$N), 3.28-3.64 (m, 12H, N{CH$_2$CH$_2$N[CH$_2$(CH$_2$)$_8$CH$_3$]CH$_2$C$_6$H$_4$CH$_2$N[CH$_2$(CH$_2$)$_8$CH$_3$]CH$_2$CH$_2$}$_3$N), 6.95-7.35 (m, 12H, N{CH$_2$CH$_2$N[CH$_2$(CH$_2$)$_8$CH$_3$]CH$_2$C$_6$H$_4$CH$_2$N[CH$_2$(CH$_2$)$_8$CH$_3$]CH$_2$CH$_2$}$_3$N). ESI-MS (m/z): [M+H]$^+$ 1441.

Synthesis of 113c: Using the procedure for synthesis of 113a with 206c in the place of 206a produced 113c in 78.0% yield. Analysis of 113c: ESI-MS (m/z): [M-I]$^+$ 2449, [M-2I]$^{2+}$ 1161, [M-Me-2I]$^+$ 2307.

Synthesis of 206d: Using the procedure for synthesis of 206a with 1-bromododecane in place of 1-bromohexane produced 206d in 99.2% yield. Analysis of 206d: $^1$H NMR (400 MHz, CD$_2$Cl$_2$, δ): 0.86-0.90 (m, 18H, N{CH$_2$CH$_2$N[CH$_2$(CH$_2$)$_{10}$CH$_3$]CH$_2$C$_6$H$_4$CH$_2$N[CH$_2$(CH$_2$)$_{10}$CH$_3$]CH$_2$CH$_2$}$_3$N), 1.26-1.44 (m, 120H, N{CH$_2$CH$_2$N[CH$_2$(CH$_2$)$_{10}$CH$_3$]CH$_2$C$_6$H$_4$CH$_2$N[CH$_2$(CH$_2$)$_{10}$CH$_3$]CH$_2$CH$_2$}$_3$N), 2.30-2.57 (m, 36H, N{CH$_2$CH$_2$N[CH$_2$(CH$_2$)$_{10}$CH$_3$]CH$_2$C$_6$H$_4$CH$_2$N[CH$_2$(CH$_2$)$_{10}$CH$_3$]CH$_2$CH$_2$}$_3$N), 3.28-3.64 (m, 12H, N{CH$_2$CH$_2$N[CH$_2$(CH$_2$)$_{10}$CH$_3$]CH$_2$C$_6$H$_4$CH$_2$N[CH$_2$(CH$_2$)$_{10}$CH$_3$]CH$_2$CH$_2$}$_3$N), 6.95-7.33 (m, 12H, N{CH$_2$CH$_2$N[CH$_2$(CH$_2$)$_{10}$CH$_3$]CH$_2$C$_6$H$_4$CH$_2$N[CH$_2$(CH$_2$)$_{10}$CH$_3$]CH$_2$CH$_2$}$_3$N). ESI-MS (m/z): [M+H]$^+$ 1610.

Synthesis of 113d: Using the procedure for synthesis of 113a with 206d in the place of 206a produced 113d in 61.0% yield. Analysis of 113d: ESI-MS (m/z): [M-2Me-4I]$^{2+}$ 1103, [M-3Me-5I]$^{2+}$ 1032, [M-5Me-8I]$^{3+}$ 551.

Synthesis of 113e: To the flask containing the product 206a (13.8 g, 12.5 mmoles) was added DMF (31 mL). Then benzyl bromide (21.4 g, 14.9 ml, 125 mmoles) was added and the reaction solution was heated with a thermostat controlled oil bath set to 80 °C. After being heated for about 14 h, the heat was removed and the reaction solution cooled to room temperature. Work Up of 113e: The solution was transferred into a 1000 mL flask, ethyl acetate (250 mL) was added and the solution stirred for 30 min. Then the supernatant was removed by filtration. The precipitate was washed with ethyl acetate (3×60 mL) and the volatiles were removed by vacuum transfer leaving an off white powder (19.4 g, 7.86 mmoles, 63.9% yield). Analysis of 113e: ESI-MS (m/z): [M-2Br]$^{2+}$ 1156, [M-Bz-2Br]$^+$ 2222, [M-Bz-3Br]$^{2+}$ 1071.

Synthesis of 113f: Using the procedure for synthesis of 113e with 206d in place of 206a produced 113f in 51.4% yield. Analysis of 113f: ESI-MS (m/z): [M-Bz-3Br]$^{2+}$ 1323, [M-Bz4Br]$^{3+}$856, [M-3Bz4Br]$^+$ 2385.

Synthesis of 206g: Using the procedure for synthesis of 206a with 1-bromohexadecane in place of 1-bromohexane produced 206 g in 100% yield. Analysis of 206g: $^1$H NMR (400 MHz, CD$_2$Cl$_2$, δ): 0.85-0.88 (m, 18H, N {CH$_2$CH$_2$N[CH$_2$(CH$_2$)$_{14}$CH$_3$]CH$_2$C$_6$H$_4$CH$_2$N[CH$_2$(CH$_2$)$_{14}$CH$_3$]CH$_2$CH$_2$}$_3$N), 1.22-1.42 (m, 168H, N{CH$_2$CH$_2$N[CH$_2$(CH$_2$)$_{14}$CH$_3$]CH$_2$C$_6$H$_4$CH$_2$N[CH$_2$(CH$_2$)$_{14}$CH$_3$]CH$_2$CH$_2$}$_3$N), 2.28-2.78 (m, 36H, N {CH$_2$CH$_2$N[CH$_2$(CH$_2$)$_{14}$CH$_3$]CH$_2$C$_6$H$_4$CH$_2$N[CH$_2$(CH$_2$)$_{14}$CH$_3$]CH$_2$CH$_2$}$_3$N), 3.28-3.65 (m, 12H, N {CH$_2$CH$_2$N[CH$_2$(CH$_2$)$_{14}$CH$_3$]CH$_2$C$_6$H$_4$CH$_2$N[CH$_2$(CH$_2$)$_{14}$CH$_3$]CH$_2$CH$_2$}$_3$N), 6.85-7.33 (m, 12H, N{CH$_2$CH$_2$N[CH$_2$(CH$_2$)$_{14}$CH$_3$]CH$_2$C$_6$H$_4$CH$_2$N[CH$_2$(CH$_2$)$_{14}$CH$_3$]CH$_2$CH$_2$}$_3$N). ESI-MS (m/z): [M+H]$^+$ 1946.

Synthesis of 206h: To a 100 mL flask was added 204 (1.01 g, 1.69 mmoles) and DMF (8.4 mL). Upon stirring for about an hour sodium carbonate (1.08 g, 10.2 mmoles) was added followed by 1-bromobutane (1.39 g, 1.09 mL, 10.2 mmoles) and the reaction flask fitted with a reflux condenser. The solution was refluxed on a thermostat controlled oil bath set to 70 °C. for about 14 h. Then the heat was removed and the reaction solution was cooled to room temperature. Work Up of 206h: The volatiles were removed by vacuum transfer, then the crude product was combined with 1.0 M NaOH (25 mL) and dichloromethane (25 mL). The phases were separated and the aqueous extracted with dichloromethane (2×25 mL). The organic phases were combined, washed with water (2×25 mL), dried over sodium sulfate and the volatiles removed to leave a light greenish-yellow oil (1.18 g, 1.26 mmoles, 74.5% yield). Analysis of 206h: ESI-MS (m/z): [M+H]$^+$ 936 and related peaks.

Synthesis of 113h: To the flask containing the product 206h (0.661 g, 0.653 mmoles) was added DMF (6.5 mL). Then methyl iodide (0.927 g, 0.406 ml, 6.53 mmoles) was added and the reaction solution was heated with a thermostat controlled oil bath set to 50 °C. After being heated for about 14 h, the heat was removed and the reaction solution cooled to room temperature. Work Up of 113h: To the reaction solution was added ethyl acetate (80 mL) and the solution stirred for 90 min. The solution was filtered and the precipitate washed with ethyl acetate (3×10 mL) and the volatiles removed by vacuum transfer leaving an off white powder (1.30 g, 0.626 mmoles, 95.9% yield). Analysis of 113h: ESI-MS (m/z): [M-21]$^{2+}$ 992 and related peaks.

Synthesis of a bridged polycyclic compound with a surface linker:

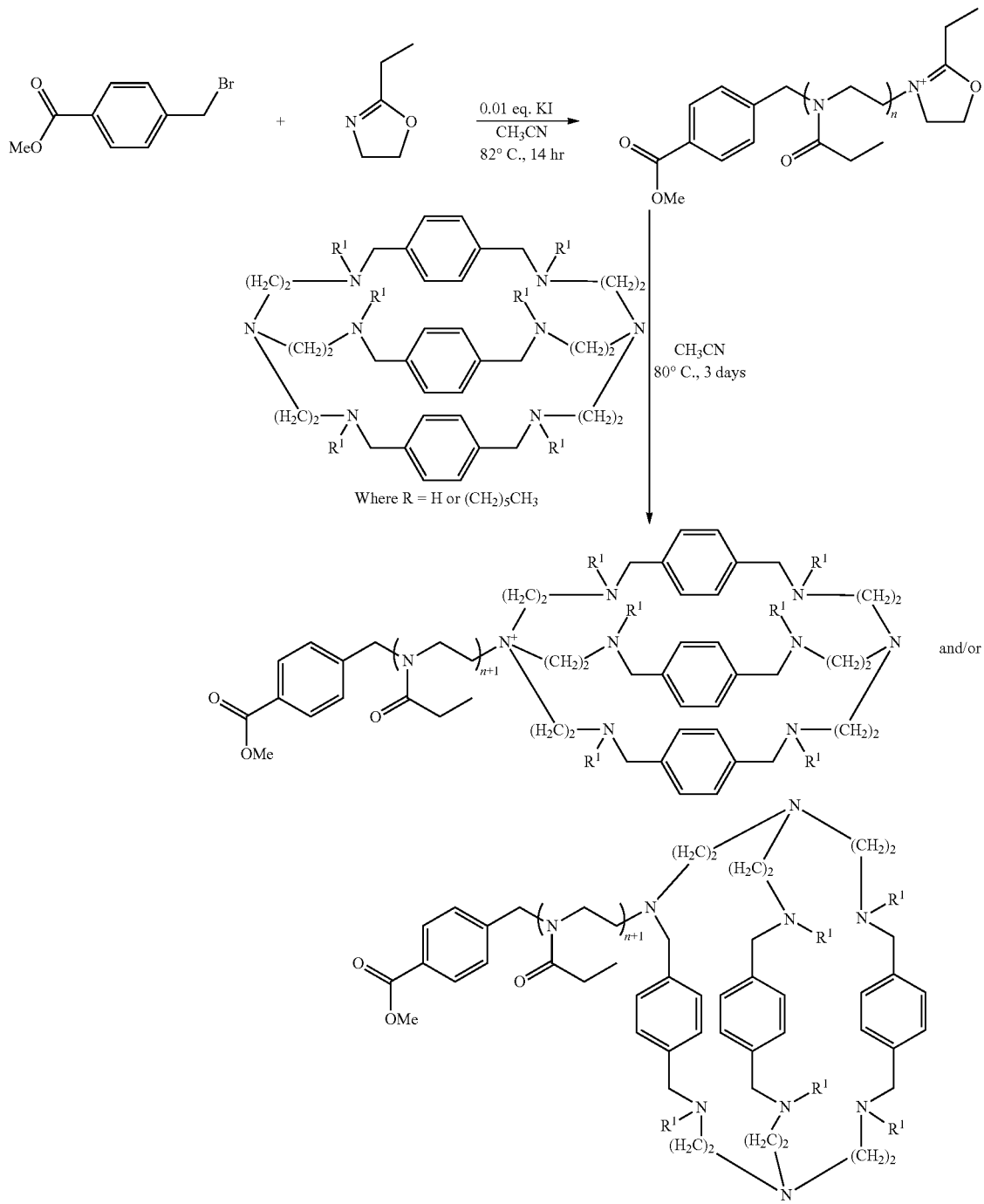

General Experimental: All manipulations were carried out using Schlenk technique under nitrogen atmosphere. Acetonitrile, anhydrous, was purchased from EMD. The 2-ethyl oxazoline was purchased from Acros Organics and distilled before use from phosphorous pentoxide. Methyl-4-(bromomethyl)benzoate and potassium iodide were purchased from Aldrich and used without further purification. Cryptand 206a was synthesized as disclosed previously. NMR analysis was performed on a JEOL Eclipse+400 instrument at Acorn NMR, Inc. in Livermore, Calif. MS analysis was performed at Scripps Center for Mass Spectrometry in La Jolla, Calif.

Synthesis of 208: To a 50 mL flask was added methyl-4-(bromomethyl)benzoate (1.13 g, 4.95 mmol), acetonitrile (5 mL), potassium iodide (8.22 mg) and 2-ethyl oxazoline (5.0 mL, 4.91 g, 49.5 mmoles). The flask was fitted with a reflux condenser and placed in an oil bath set to 82° C. for 14 h. After heating the reaction solution was cooled to room temperature. For polymer analysis, a 0.5 mL sample of the reaction solution was stirred in 5 mL of water overnight at room temperature before the volatiles removed by vacuum transfer at room temperature. Analysis of 208: MALDI-TOF MS (m/z): $[M+H_2O+H]^+$ 860.6 (n=7), $[M+H_2O+H]^+$ 960.0 (n=8), $[M+H_2O+H]^+$ 1058.7 (n=9), $[M+H_2O+H]^+$ 1157.8 (n=10).

Synthesis of 210: To a 50 mL flask was added 206a (50 mg, 0.0534 mmoles), 208 (0.0540 mL, 0.0267 mmoles, 0.495 M) and 1.0 mL of $CH_3CN$. The flask was heated on an 80° C. oil bath for 3 days. After heating the reaction solution was cooled to room temperature and the volatiles removed by vacuum transfer. Analysis of 210: MALDI-TOF MS (m/z): for $R^1=(CH_2)_5CH_3$; $[M+H]^+$ 1554 (6×$R^1$ where $R^1=(CH_2)_5CH_3$, n=3), $[M+H]^+$ 1653 (6×$R^1$ where $R^1=(CH_2)_5CH_3$, n=4), $[M+H]+1752$ (6×$R^1$ where $R^1=(CH_2)_5CH_3$, n=5), and $[M+H]^+$ 1243 (R=H, n=4), $[M+H]^+$ 1342 (R=H, n=5), $[M+H]^+$ 1441 (R=H, n=6).

Further Example of a Synthesis of a Bridged Polycyclic Compound with a Surface Linker:

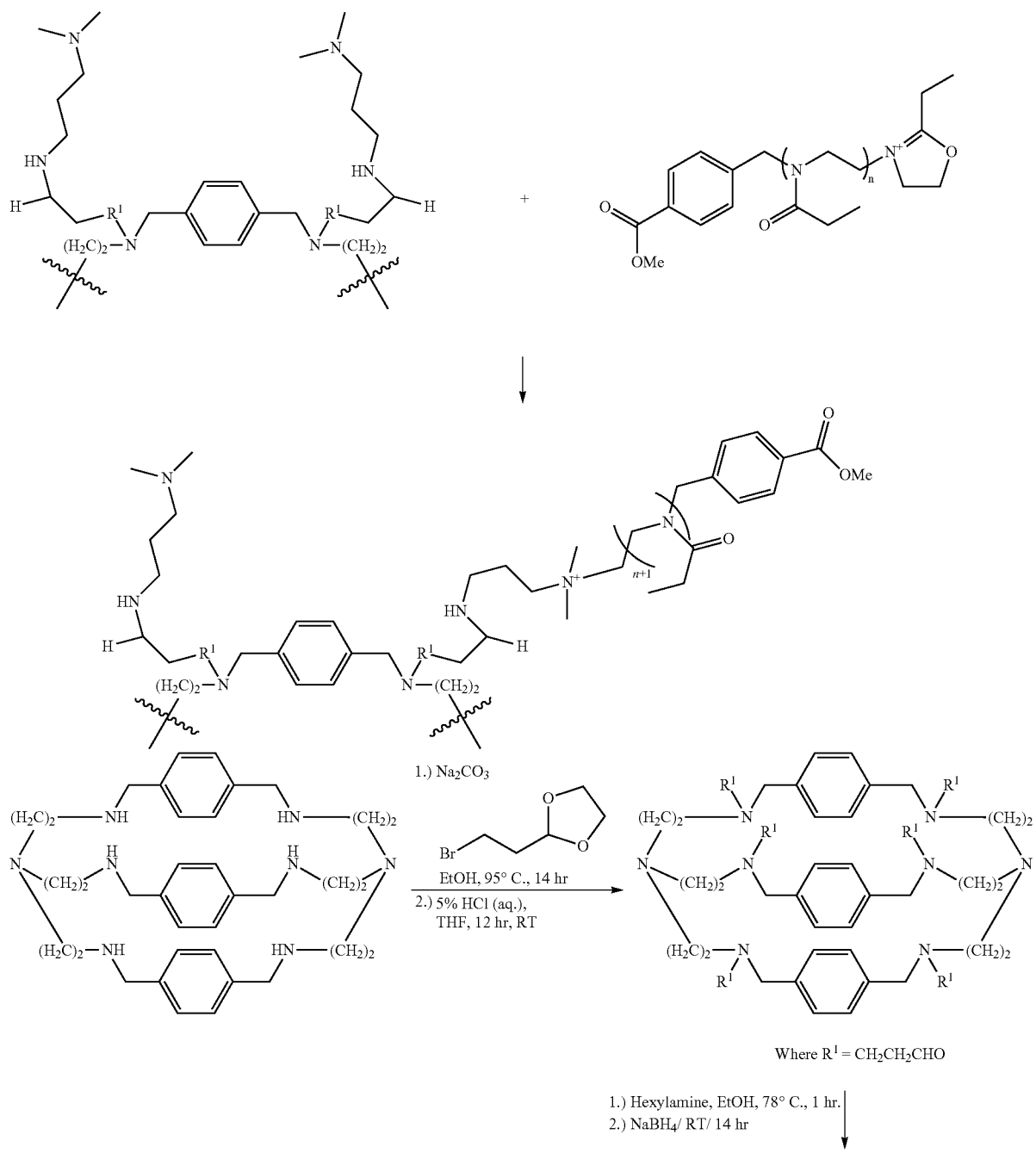

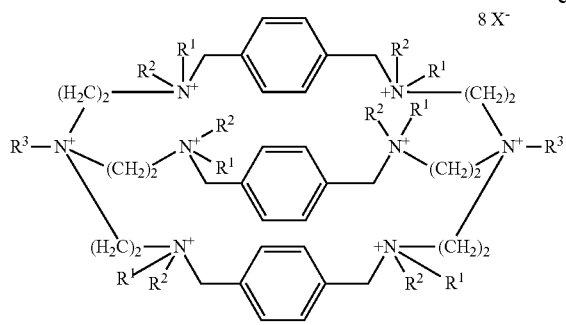

Where: $R^1 = CH_2CH_2CH_2NH(CH_2)_5CH_3$
$R^2 = $ Bz or Me
$R^3 = R^1$, Bz or Me $\xleftarrow{\begin{array}{c}\text{CH3I or BzBr}\\\text{DMF}\\70°\text{ C.}\\14\text{ hr}\end{array}}$

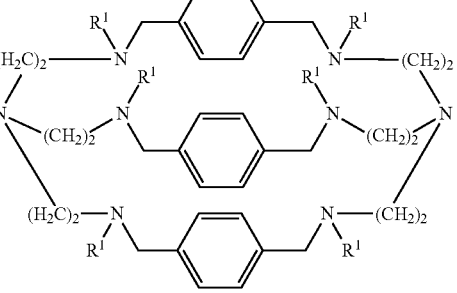

Where: $R^1 = CH_2CH_2CH_2NH(CH_2)_5CH_3$

Formulation of Coating Composition Containing C6C1 Alkylated Bridged Polycyclic Compound General Experimental: Poly vinyl alcohol (PVA), 80% hydrolized, typical mw 9,000-10,000, poly methyl methacrylate (PMMA), typical mw 120,000 and poly(methylmethacrylate-co-butylmethacrylate), (PMMABMA), typical mw 75,000 were purchased from Aldrich and used without further purification. Acetone and 1-butanol were also purchased from Aldrich and used without further purification. Active ingredient C6C1 alkylated cryptand salt was synthesized as disclosed previously. Mixing was preformed by an IKA "RW16 Basic" stirrer equipped with a "R1300 Dissolver Stirrer" impeller for larger scale and for smaller scale the solutions were magnetically stirred.

Formulation of PVA in Water Example: A 10% PVA in water is used for example although formulations between 1 and 20% PVA in water were produced (the preferred formulation range is 15 to 20% PVA in water). Water (900 mL) was stirred and PVA (100 g) was added in four portions with 10 minute separation between each portion. The solution was then stirred until clear and colorless. The foam was removed with a paper towel and the solution transferred to a glass bottle for storage.

Formulation of PVA/PMMA in Water Example: A sample of the 15% PVA water solution (50 mL) was added to a small bottle and PMMA (50 mg, 0.1%) was added. The solution was magnetically stirred for 24 h resulting in a clear homogeneous solution.

Formulation of PVA/PMMABMA in Water Example: A 15% PVA in water is used for example although formulations between 1 and 20% PVA in water were produced (the preferred formulation range is 15 to 20% PVA in water). Water (360 mL) was stirred and PVA (60 g, 0.1%) was added in four portions with 10 minute separation between each portion. Then PMMABMA (2 g) was added and the solution was then stirred until clear and colorless.

Formulation of the Active Ingredient in PVA/Water Solution Example: A sample of the 10% PVA/water solution (50 mL) was added to a small bottle and the active ingredient (1.5 g) previously dissolved in DMF (3.0 mL) was added. The solution was magnetically stirred for 24 h resulting in a clear homogeneous solution.

Formulation of the Active Ingredient in PVA/PMMA/Water Solution Example: A sample of the 15% PVA/0.1% PMMA/water solution (0.5 mL) was added to a vial containing 7.5 mg of active ingredient and the solution stirred for 5 min. Then 0.050 mL of 1-butanol was added and the solution stirred for 1 day.

Formulation of the Active Ingredient in PVA/PMMA/Water Solution Example: A sample of the 15% PVA/0.1% PMMA/water solution (0.5 mL) was added to a vial containing 7.5 mg of active ingredient and the solution stirred for 5 min. Then 0.050 mL of acetone was added and the solution stirred for 1 day.

Formulation of the Active Ingredient in PVA/PMMABMA/Water Solution Example: A sample of the 15% PVA/0.1% PMMABMA/water solution (0.5 mL) was added to a vial containing 7.5 mg of active ingredient and the solution stirred for 5 min. Then 0.050 mL of 1-butanol was added and the solution stirred for I day.

Formulation of the Active Ingredient in PVA/PMMABMA/Water Solution Example: A sample of the 15% PVA/0.1% PMMABMA/water solution (0.5 mL) was added to a vial containing 7.5 mg of active ingredient and the solution stirred for 5 min. Then 0.050 mL of acetone was added and the solution stirred for 1 day.

In the examples above DMF, 1-butanol and/or acetone were used as a solvent. Other solvents for this system are dimethyl sulfoxide, isopropanol, pentanol, hexanol, propylene glycol, ethylene glycol, ethylene glycol 2-ethylhexyl ether, di(ethylene glycol)2-ethylhexyl ether, ethylene glycol butyl ether, di(ethylene glycol) hexyl ether, 3-ethylhexanol, hexanol, 1,4-butanediol, ethanol and the like.

Other additives for this formulation: PMMA, sodium borate, boric acid, potassium tetrafluoroborate, sodium tetrafluoroborate, EDTA, disodium EDTA, metal oxides, silica and the like.

EXAMPLES:

Time Kill Test Assay for Antimicrobial Agents

Test Substance Preparation: A 1.0 mL volume of DMSO was placed into a sterile vessel and vortex mixed for 10-15 seconds. Immediately following the mixing of the DMSO, 0.025 g of the test substance powder was added to the sterile vessel and vortex mixed for 10-15 seconds to make a stock solution. The stock solution was then combined with 9.9 mL of filter sterilized deionized water, vortex mixed for 10-15 seconds and 0.1 mL of the solution was discarded resulting in a total volume of 9.9 mL and a test substance concentration of 0.25 mg/mL.

Experimental Design: A suspension of bacterial cells was exposed to the test substance for specified contact times. After exposure, an aliquot of the suspension was transferred to a neutralizing subculture media and assayed for survivors. Appropriate purity, sterility, initial suspension population control and neutralization controls were performed.

Test Organisms: Test organisms included *Staphylococcus aureus* and *Escherichia coli* in a growth medium of tryptic soy agar with 5% sheep blood, as well as, *Aspergillus niger* in a growth medium of sabouraud agar modified.

Time Kill Test Assay for 113h vs. 113b: Under the conditions of this study, 113h, demonstrated a 98.5% or 1.828 log reduction of *Staphylococcus aureus* survivors after a 5 minute exposure, a 92.5% or 1.13 log reduction after a 10 minute exposure, a 99.5% or 2.33 log reduction after a 30 minute exposure, a >99.8% or 2.92 log reduction after a 1 hour exposure, a 99.999% or 5.0 log reduction after a 6 hour exposure, a 99.999% or 5.7 log reduction after a 24 hour exposure when tested at room temperature (24° C.).

Under the conditions of this study, 113b, demonstrated a 99.1% or 2.029 log reduction of *Staphylococcus aureus* survivors after a 5 minute exposure, a 94.2% or 1.24 log reduction after a 10 minute exposure, a 99.1% or 2.06 log reduction after a 30 minute exposure, a 99.8% or 2.63 log reduction after a 1 hour exposure, a 99.99% or 4.35 log reduction after a 6 hour exposure, a >99.999% or >5.7 log reduction after a 24 hour exposure when tested at room temperature (24° C.).

Under the conditions of this study, 113h, demonstrated a 77.7% or 0.66 log reduction of *Escherichia coli* survivors after a 5 minute exposure, a 86.6% or 0.88 log reduction after a 10 minute exposure, a 82.9% or 0.77 log reduction after a 30 minute exposure, a 91.1% or 1.06 log reduction after a 1 hour exposure, a 98.5% or 1.83 log reduction after a 6 hour exposure, a 99.7% or 2.58 log reduction after a 24 hour exposure when tested at room temperature (24° C.).

Under the conditions of this study, 113b, demonstrated a 89.0% or 0.96 log reduction of *Escherichia coli* survivors after a 5 minute exposure, a 84.9% or 0.83 log reduction after a 10 minute exposure, a 93.7% or 1.21 log reduction after a 30 minute exposure, a 94.6% or 1.27 log reduction after a 1 hour exposure, a 99.0% or 2.00 log reduction after a 6 hour exposure, a 99.5% or 2.28 log reduction after a 24 hour exposure when tested at room temperature (24° C.).

Under the conditions of this study, 113h, demonstrated no percent or log reduction of *Aspergillus niger* following 5 minute, 10 minute, 30 minute, 1 hour, 6 hour, and 24 hour exposure times when tested at room temperature (24° C.).

Under the conditions of this study, 113b, demonstrated a 47.0% or 0.28 log reduction of *Aspergillus niger* survivors after a 5 minute exposure, a 38.9% or 0.22 log reduction after a 10 minute exposure, a 47.6% or 0.28 log reduction after a 30 minute exposure, a 48.1% or 0.29 log reduction after a 1 hour exposure, a 47.6% or 0.28 log reduction after a 6 hour exposure, a 27.8% or 0.14 log reduction after a 24 hour exposure when tested at room temperature (24° C.).

Time Kill Test Assay for 113a: Under the conditions of this study, 113a, demonstrated a 98.6% or 1.856 log reduction of *Staphylococcus aureus* survivors after a 5 minute exposure, a 99.9% or 3.97 log reduction after a 10 minute exposure, a >99.999% or >5.8 log reduction after a 30 minute, 1 hour, 6 hour, and 24 hour exposure period when tested at room temperature (20° C.).

Under the conditions of this study, 113a, demonstrated a 96.3% or 1.42 log reduction of *Escherichia coli* survivors after a 5 minute exposure, a 97.7% or 1.64 log reduction after a 10 minute exposure, a 99.3% or 2.14 log reduction after a 30 minute exposure, a 99.6% or 2.35 log reduction after a 1 hour exposure, a 99.9% or 3.660 log reduction after a 6 hour exposure, a >99.9999% or >6.0 log reduction after a 24 hour exposure when tested at room temperature (20° C.).

Under the conditions of this study, 113a, demonstrated a 18.3% or 0.09 log reduction of *Aspergillus niger* survivors after a 5 minute exposure, a 38.0% or 0.21 log reduction after a 10 minute exposure, a 28.2% or 0.14 log reduction after a 30 minute exposure, a 39.4% or 0.22 log reduction after a 1 hour exposure, no reduction after a 6 hour exposure, a 25.4% or 0.13 log reduction after a 24 hour exposure when tested at room temperature (20° C.).

Time Kill Test Assay for 113a vs. 113d: Under the conditions of this study, 113a, demonstrated a 97.9% or 1.68 log reduction of *Staphylococcus aureus* survivors after a 5 minute exposure, a 99.9% or 3.22 log reduction after a 10 minute exposure, a 99.999% or 5.2 log reduction after a 30 minute, a >99.999% or >5.5 log reduction after a 1 hour, 6 hour, and 24 hour exposure period when tested at room temperature (22° C.).

Under the conditions of this study, 113d, demonstrated a 82.5% or 0.76 log reduction of *Staphylococcus aureus* survivors after a 5 minute exposure, a 84.1% or 0.80 log reduction after a 10 minute exposure, a 96.8% or 1.50 log reduction after a 30 minute, a 99.8% or 2.72 log reduction after a 1 hour, and a >99.999% or >5.5 log reduction after a 6 hour, and 24 hour exposure period when tested at room temperature (22° C.).

Under the conditions of this study, 113a, demonstrated a 92.3% or 1.12 log reduction of *Escherichia coli* survivors after a 5 minute exposure, a 91.5% or 1.07 log reduction after a 10 minute exposure, a 93.7% or 1.21 log reduction after a 30 minute exposure, a 95.5% or 1.35 log reduction after a 1 hour exposure, a 99.4% or 2.23 log reduction after a 6 hour exposure, a 99.9% or 3.58 log reduction after a 24 hour exposure when tested at room temperature (22° C.).

Under the conditions of this study, 113d, demonstrated a 38.7% or 0.22 log reduction of *Escherichia coli* survivors after a 5 minute exposure, a 80.5% or 0.72 log reduction after a 10 minute exposure, a 78.7% or 0.68 log reduction after a 30 minute exposure, a 89.3% or 0.98 log reduction after a 1 hour exposure, a 98.0% or 1.70 log reduction after a 6 hour exposure, a 99.9% or 3.07 log reduction after a 24 hour exposure when tested at room temperature (22° C.).

Under the conditions of this study, 113a, demonstrated no reduction of *Aspergillus niger* survivors after a 5 minute, a 10 minute, a 30 minute, and a 1 hour exposure, a 2.2% or 0.01 log reduction after a 6 hour exposure, a 135.5% or 0.19 log reduction after a 24 hour exposure when tested at room temperature (22° C.).

Under the conditions of this study, 113d, demonstrated no reduction of Aspergillus niger survivors after a 5 minute exposure, a 15.4% or 0.07 log reduction after a 10 minute, a 14.3% or 0.07 log reduction after a 30 minute exposure, a 3.3% or 0.02 log reduction after a 1 hour exposure, a 4.4% or 0.02 log reduction after a 6 hour exposure, a 11.3% or 0.05 log reduction after a 24 hour exposure when tested at room temperature (22° C.).

Residual Surface Time Kill Test Assay for 113a vs. 113e: Under the conditions of this study, 113a, demonstrated a 94.9% or 1.32 log reduction of *Aspergillus niger* survivors after a 1 hour exposure, a 95.0% or 1.30 log reduction after a 6 hour, and a 98.8% or 1.93 log reduction after a 24 hour exposure times when tested at room temperature (21.5° C.).

Under the conditions of this study, 113e, demonstrated a 92.7% or 1.15 log reduction of *Aspergillus niger* survivors after a 1 hour exposure, a 93.8% or 1.21 log reduction after a 6 hour exposure, a 89.6% or 0.98 log reduction after a 24 hour exposure when tested at room temperature (21.5° C.).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of coating an oral surface, comprising:
applying one or more bridged polycyclic compounds to at least a portion of an oral surface, wherein at least one of the bridged polycyclic compounds has a general structure:

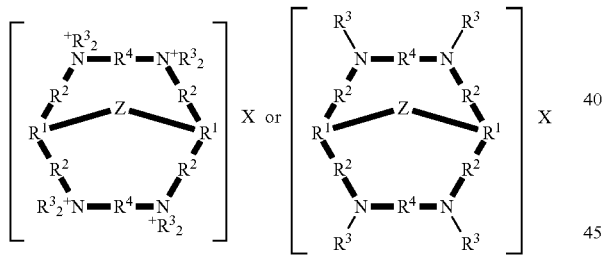

wherein each $R^1$ is independently N, $N^+R^3$, or $N^+H$;
wherein each $R^2$ is independently an alkyl group, a substituted alkyl group, or an alkene;
wherein each $R^3$ is independently an alkyl group, a substituted alkyl group, an aryl group, a substituted aryl group, a heterocycle group, a substituted heterocycle group, an alkene, an ether, a polyethyleneglycol, a benzyl group, a hydrogen, a hydrophilic group, or a polyethyleneimine;
wherein each $R^4$ is independently a substituted aryl group;
wherein Z comprises at least one bridge, wherein at least one of the bridges is —$R^2$—$N^+R^3{}_2$—$R^4$—$N^+R^3{}_2$—$R^2$— or —$R^2$—$NR^3$—$R^4$—$NR^3$—$R^2$—, and wherein each bridge independently couples $R^1$ to $R^1$;
wherein the aryl group is a phenyl, a naphthyl, a biphenyl, a diphenylmethyl, or a benzophenone;
wherein the substituted alkyl group comprises at least one substituent and wherein each substituent is independently an aryl, an acyl, an alkyl, a halogen, an alkylhalo, a hydroxy, an amino, an alkoxy, an alkylamino, an acylamino, an acyloxy, an aryloxy, an aryloxyalkyl, a mercapto, a saturated cyclic hydrocarbon, an unsaturated cyclic hydrocarbon, and/or a heterocycle;
wherein the substituted aryl group is a phenyl having at least one substituent, a naphthyl having at least one substituent, a biphenyl having at least one substituent, a diphenylmethyl having at least one substituent, or a benzophenone having at least one substituent, and wherein each substituent is independently an alkyl, an aryl, an acyl, a halogen, an alkylhalo, a hydroxy, an amino, an alkoxy, an alkylamino, an acylamino, an acyloxy, an aryloxy, an aryloxyalkyl, a thioether, a heterocycle, a saturated cyclic hydrocarbon, and/or an unsaturated cyclic hydrocarbon;
wherein the substituted heterocycle group comprises at least one substituent and wherein each substituent is independently an alkyl, an aryl, an acyl, a halogen, an alkylhalo, a hydroxy, an amino, an alkoxy, an alkylamino, an acylamino, an acyloxy, an aryloxy, an aryloxyalkyl, a thioether, a heterocycle, a saturated cyclic hydrocarbon, and/or an unsaturated cyclic hydrocarbon;
wherein each of the hydrophilic groups independently comprises a hydroxyl, a methoxy, a carboxylic acid, an ester of a carboxylic acid, an amide, an amino, a cyano, an isocyano, an ammonium salt, a sulfonium salts, a phosphonium salt, a mono-alkyl substituted amino groups, a di-alkyl substituted amino group, a polypropyleneglycol, a polyethylene glycol, an epoxy group, an acrylate, a sulfonamide, a nitro, a —OP(O)(OCH$_2$CH$_2$N$^+$R$^3$R$^3$R$^3$)O$^-$, a guanidinium, an aminate, an acrylamide, a pyridinium, a piperidine, a polymethylene chains substituted with an alcohol, a carboxylate, an acrylate, or a methacrylate, an alkyl chain having internal amino or substituted amino groups comprising internal —NH—, —NC(O)R$^3$—, or —NC(O)CH=CH$_2$—groups, a polycaprolactone, a polycaprolactone diol, a poly(acetic acid), a poly(vinyl acetate), a poly(2-vinyl pyridine), a cellulose ester, a cellulose hydroxylether, a poly(L-lysine hydrobromide), a poly (itaconic acid), a poly(maleic acid), a poly(styrenesulfonic acid), a poly(aniline), or a poly(vinyl phosphonic acid); and
wherein X comprises one or more negatively charged counter ions; and
forming an antimicrobial coating over at least a portion of the oral surface.

2. The method of claim 1, wherein at least one of the bridged polycyclic compounds comprises at least four quaternary ammonium moieties.

3. The method of claim 1, wherein at least one quaternary ammonium moiety defining at least one cyclic group of one or more of the bridged polycyclic compounds further comprises an alkyl group, a substituted alkyl group, an aryl group, a heterocycle group, a substituted heterocycle group, or a substituted aryl group.

4. The method of claim 1, wherein at least one quaternary ammonium moiety defining at least one cyclic group of one or more of the bridged polycyclic compounds further comprises an alkyl group, a substituted alkyl group, an aryl group, or a substituted aryl group and an alkyl group, a substituted alkyl group, an aryl group, or a substituted aryl group.

5. The method of claim 1, wherein at least one quaternary ammonium moiety defining at least one cyclic group of one or more of the bridged polycyclic compounds further comprises a C6 alkyl group or a C6 substituted alkyl group and a methyl group or a benzyl group.

6. The method of claim 1, wherein at least one of the bridged polycyclic compound has a general structure (I):

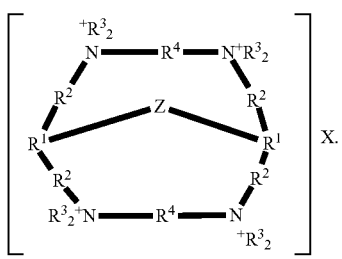

(I)

7. The method of claim 1, wherein at least one X is iodine.

8. The method of claim 1, wherein at least one X is bromine or chlorine.

9. The method of claim 1, wherein at least one of the bridged polycyclic compound has a general structure (IV):

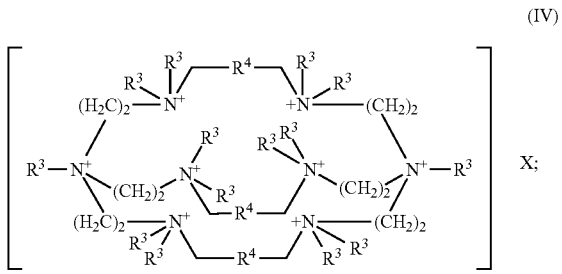

(IV)

wherein at least one $R^3$ is a benzyl group, and wherein at least one $R^3$ is a C5-C7 alkyl group or a C5-C7 substituted alkyl group; and wherein at least one $R^4$ is an aryl group or a substituted aryl group.

10. The method of claim 1, wherein at least one of the bridged polycyclic compound has a general structure (IVa):

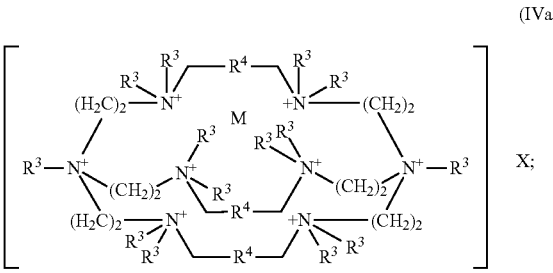

(IVa)

wherein at least one $R^3$ is a benzyl group, wherein at least one $R^3$ is a C5-C7 alkyl group or a C5-C7 substituted alkyl group; wherein at least one $R^4$ is an aryl group or a substituted aryl group, and wherein M comprises one or more guest molecules associated with one or more portions of compound (IVa).

11. The method of claim 1, wherein the oral surface comprises at least a portion of a tooth surface, at least a portion of a gum, at least a portion of soft tissue, or at least a portion of a dental fixture.

12. The method of claim 1, wherein the one or more bridged polycyclic compounds are part of a composition, wherein the composition further comprises a at least one gelator such that the composition is gel.

13. The method of claim 1, wherein the one or more bridged polycyclic compounds are part of a composition, and wherein the composition further comprises at least one polymer or polymerizable compound, and further comprising using the composition as a bonding agent.

14. The method of claim 1, wherein the one or more bridged polycyclic compounds are part of a composition, and wherein the composition further comprises at least one polymer or polymerizable compound, and further comprising using the composition as a resin cement.

15. The method of claim 1, wherein the one or more bridged polycyclic compounds are part of a composition, and wherein the composition further comprises at least one polymer or polymerizable compound, and further comprising using the composition as a sealant.

16. The method of claim 1, wherein the one or more bridged polycyclic compounds are part of a composition, and wherein the composition further comprises at least one polymer or polymerizable compound, and further comprising applying one or more of the bridged polycyclic compounds as at least a portion of a varnish.

17. The method of claim 1, wherein the one or more bridged polycyclic compounds are part of a composition, and wherein the composition further comprises at least one polymer or polymerizable compound, and further comprising using the composition as a resin.

18. The method of claim 1, wherein at least one $R^3$ comprises a guanidinium.

19. The method of claim 1, wherein at least one of the cyclic groups comprises an amide moiety coupled to the cyclic group.

20. The method of claim 1, wherein at least one $R^3$ comprises a quaternary ammonium moiety.

21. The method of claim 1, wherein the oral surface comprises the oral surface of a dog or a cat.

22. The method of claim 1, wherein at least one of the bridged polycyclic compound has a general structure:

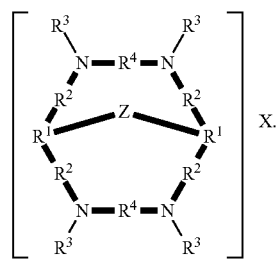

23. The method of claim 22, wherein $R^2$ is —$(CH_2)_2$—.

24. The method of claim 22, wherein $R^4$ is a substituted aryl group, and wherein the substituted aryl group comprises —$(CH_2)$-phenyl-$(CH_2)$—.

25. The method of claim 22, wherein at least one $R^3$ is a substituted aryl group.

26. The method of claim 22, wherein at least one $R^3$ comprises a substituted aryl group, wherein at least one of the substituted aryl group's substituents comprises a guanidinium group.

27. The method of claim 22, wherein at least one $R^3$ comprises a substituted aryl group, wherein at least one of the substituted aryl group's substituents is a halogen, and wherein at least one of the substituted aryl group's substituents comprises a guanidinium group.

28. The method of claim 1, wherein at least one of the bridged polycyclic compound has a general structure:

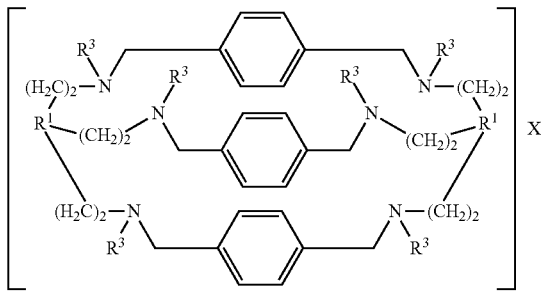

wherein each $R^1$ is independently N, $N^+H$, or $N^+R^3$;
wherein at least one $R^3$ comprises a substituted aryl group, wherein at least one of the substituted aryl group's substituents is a halogen, and wherein at least one of the substituted aryl group's substituents comprises a guanidinium group; and
wherein X comprises one or more negatively charged counter ions.

29. The method of claim 1, wherein the one or more bridged polycyclic compounds are part of a composition, wherein the composition further comprises a solvent.

30. The method of claim 1, wherein the one or more bridged polycyclic compounds are part of a composition, wherein the composition further comprises a solvent, and wherein the solvent comprises water and an alcohol based solvent.

31. The method of claim 1, wherein the one or more bridged polycyclic compounds are part of a composition, wherein the composition further comprises a polymer and/or a polymerizable compound.

32. The method of claim 1, wherein at least one $R^3$ comprises a substituted aryl group.

33. The method of claim 1, wherein at least one $R^3$ comprises a substituted aryl group, wherein at least one of the substituted aryl group's substituents comprises a guanidinium group.

34. The method of claim 1, wherein each $R^3$ is independently an alkyl group, a substituted alkyl group, an aryl group, a substituted aryl group, a heterocycle group, a substituted heterocycle group, an alkene, an ether, a polyethyleneglycol, a benzyl group, a hydrogen, a hydrophilic group, or a polyethyleneimine and wherein at least one alkyl group comprises a C5-C7 alkyl group.

35. The method of claim 1, wherein the one or more bridged polycyclic compounds are part of a composition, wherein the composition further comprises a solvent, and wherein the solvent comprises water.

36. The method of claim 1, wherein the one or more bridged polycyclic compounds are part of a composition, wherein the composition further comprises a solvent, and wherein the solvent comprises an alcohol based solvent.

37. The method of claim 1, wherein the one or more bridged polycyclic compounds are part of a composition, wherein the composition further comprises a solvent and a polymer, and wherein the solvent comprises water and an alcohol based solvent.

38. The method of claim 28, wherein the one or more bridged polycyclic compounds are part of a composition, wherein the composition further comprises a solvent, and wherein the solvent comprises water.

39. The method of claim 28, wherein the one or more bridged polycyclic compounds are part of a composition, wherein the composition further comprises a solvent, and wherein the solvent comprises an alcohol based solvent.

40. The method of claim 28, wherein the one or more bridged polycyclic compounds are part of a composition, wherein the composition further comprises a solvent, and wherein the solvent comprises water and an alcohol based solvent.

41. The method of claim 28, wherein the one or more bridged polycyclic compounds are part of a composition, wherein the composition further comprises a solvent and a polymer, and wherein the solvent comprises water and an alcohol based solvent.

42. A method of coating an oral surface of a cat or a dog, comprising:
applying one or more bridged polycyclic compounds to at least a portion of an oral surface of a cat or a dog, wherein at least one of the bridged polycyclic compounds has a general structure:

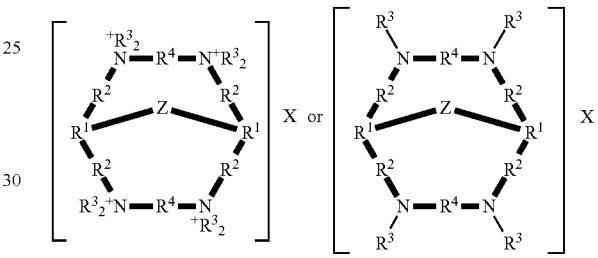

wherein each $R^1$ is independently N, $N^+R^3$, or $N^+H$;
wherein each $R^2$ is independently an alkyl group, a substituted alkyl group, or an alkene;
wherein each $R^3$ is independently an alkyl group, a substituted alkyl group, an aryl group, a substituted aryl group, a heterocycle group, a substituted heterocycle group, an alkene, an ether, a polyethyleneglycol, a benzyl group, a hydrogen, a hydrophilic group, or a polyethyleneimine;
wherein each $R^4$ is independently a substituted aryl group;
wherein Z comprises at least one bridge, wherein at least one of the bridges is $-R^2-N^+R^3{}_2-R^4-N^+R^3{}_2-R^2-$ or $-R^2-NR^3-R^4-NR^3-R^2-$, and wherein each bridge independently couples $R^1$ to $R^1$;
wherein the aryl group is a phenyl, a naphthyl, a biphenyl, a diphenylmethyl, or a benzophenone;
wherein the substituted alkyl group comprises at least one substituent and wherein each substituent is independently an aryl, an acyl, an alkyl, a halogen, an alkylhalo, a hydroxy, an amino, an alkoxy, an alkylamino, an acylamino, an acyloxy, an aryloxy, an aryloxyalkyl, a mercapto, a saturated cyclic hydrocarbon, an unsaturated cyclic hydrocarbon, and/or a heterocycle;
wherein the substituted aryl group is a phenyl having at least one substituent, a naphthyl having at least one substituent, a biphenyl having at least one substituent, a diphenylmethyl having at least one substituent, or a benzophenone having at least one substituent and wherein each substituent is independently an alkyl, an aryl, an acyl, a halogen, an alkylhalo, a hydroxy, an amino, an alkoxy, an alkylamino, an acylamino, an acyloxy, an aryloxy, an aryloxyalkyl, a thioether, a heterocycle, a saturated cyclic hydrocarbon, and/or an unsaturated cyclic hydrocarbon;

wherein the substituted heterocycle group comprises at least one substituent and wherein each substituent is independently an alkyl, an aryl, an acyl, a halogen, an alkylhalo, a hydroxy, an amino, an alkoxy, an alkylamino, an acylamino, an acyloxy, an aryloxy, an aryloxyalkyl, a thioether, a heterocycle, a saturated cyclic hydrocarbon, and/or an unsaturated cyclic hydrocarbon;
wherein each of the hydrophilic groups independently comprises a hydroxyl, a methoxy, a carboxylic acid, an ester of a carboxylic acid, an amide, an amino, a cyano, an isocyano, an ammonium salt, a sulfonium salts, a phosphonium salt, a mono-alkyl substituted amino groups, a di-alkyl substituted amino group, a polypropyleneglycol, a polyethylene glycol, an epoxy group, an acrylate, a sulfonamide, a nitro, a —OP(O)(OCH$_2$CH$_2$N$^+$R$^3$R$^3$R$^3$)O$^-$, a guanidinium, an aminate, an acrylamide, a pyridinium, a piperidine, a polymethylene chains substituted with an alcohol, a carboxylate, an acrylate, or a methacrylate, an alkyl chain having internal amino or substituted amino groups comprising internal —NH—, —NC(O)R$^3$—, or —NC(O)CH=CH$_2$— groups, a polycaprolactone, a polycaprolactone diol, a poly(acetic acid), a poly(vinyl acetate), a poly(2-vinyl pyridine), a cellulose ester, a cellulose hydroxylether, a poly(L-lysine hydrobromide), a poly(itaconic acid), a poly(maleic acid), a poly(styrenesulfonic acid), a poly(aniline), or a poly(vinyl phosphonic acid); and
wherein X comprises one or more negatively charged counter ions; and
forming an antimicrobial coating over at least a portion of the oral surface.

43. The method of claim 11, wherein at least one of the bridged polycyclic compounds comprises at least four quaternary ammonium moieties.

44. The method of claim 11, wherein at least one of the bridged polycyclic compound has a general structure (I):

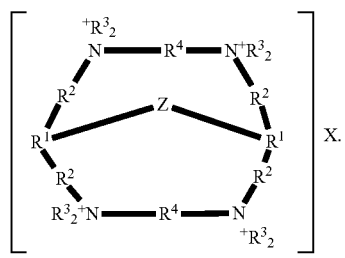

45. The method of claim 11, wherein at least one X is iodine.

46. The method of claim 11, wherein at least one X is bromine or chlorine.

47. The method of claim 11, wherein the oral surface comprises at least a portion of a tooth surface, at least a portion of a gum, at least a portion of soft tissue, or at least a portion of a dental fixture.

48. The method of claim 11, wherein the one or more bridged polycyclic compounds are part of a composition, wherein the composition further comprises a at least one gelator such that the composition is gel.

49. The method of claim 11, wherein the one or more bridged polycyclic compounds are part of a composition, and wherein the composition further comprises at least one polymer or polymerizable compound, and further comprising using the composition as a bonding agent.

50. The method of claim 11, wherein the one or more bridged polycyclic compounds are part of a composition, and wherein the composition further comprises at least one polymer or polymerizable compound, and further comprising using the composition as a resin cement.

51. The method of claim 11, wherein the one or more bridged polycyclic compounds are part of a composition, and wherein the composition further comprises at least one polymer or polymerizable compound, and further comprising using the composition as a sealant.

52. The method of claim 11, wherein the one or more bridged polycyclic compounds are part of a composition, and wherein the composition further comprises at least one polymer or polymerizable compound, and further comprising applying one or more of the bridged polycyclic compounds as at least a portion of a varnish.

53. The method of claim 11, wherein the one or more bridged polycyclic compounds are part of a composition, and wherein the composition further comprises at least one polymer or polymerizable compound, and further comprising using the composition as a resin.

54. The method of claim 11, wherein at least one R$^3$ comprises a guanidinium.

55. The method of claim 11, wherein at least one R$^3$ comprises a quaternary ammonium moiety.

56. The method of claim 11, wherein at least one of the bridged polycyclic compound has a general structure:

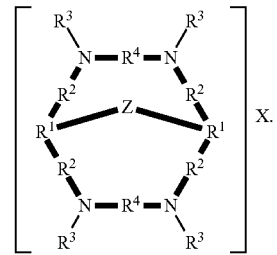

57. The method of claim 11, wherein at least one of the bridged polycyclic compound has a general structure:

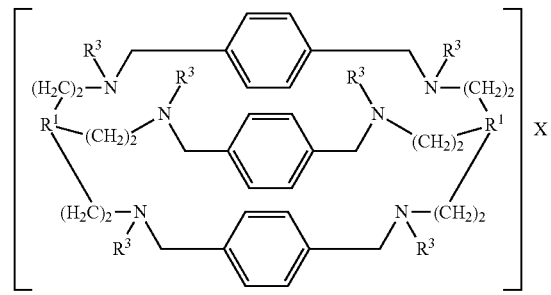

wherein each R$^1$ is independently N, N$^+$H, or N$^+$R$^3$;
wherein at least one R$^3$ comprises a substituted aryl group, wherein at least one of the substituted aryl group's substituents is a halogen, and wherein at least one of the substituted aryl group's substituents comprises a guanidinium group; and
wherein X comprises one or more negatively charged counter ions.

58. The method of claim 57, wherein the one or more bridged polycyclic compounds are part of a composition, wherein the composition further comprises a solvent, and wherein the solvent comprises water.

59. The method of claim 57, wherein the one or more bridged polycyclic compounds are part of a composition, wherein the composition further comprises a solvent, and wherein the solvent comprises an alcohol based solvent.

60. The method of claim 57, wherein the one or more bridged polycyclic compounds are part of a composition, wherein the composition further comprises a solvent, and wherein the solvent comprises water and an alcohol based solvent.

61. The method of claim 57, wherein the one or more bridged polycyclic compounds are part of a composition, wherein the composition further comprises a solvent and a polymer, and wherein the solvent comprises water and an alcohol based solvent.

62. The method of claim 11, wherein the one or more bridged polycyclic compounds are part of a composition, wherein the composition further comprises a solvent.

63. The method of claim 11, wherein the one or more bridged polycyclic compounds are part of a composition, wherein the composition further comprises a solvent, and wherein the solvent comprises water.

64. The method of claim 11, wherein the one or more bridged polycyclic compounds are part of a composition, wherein the composition further comprises a solvent, and wherein the solvent comprises an alcohol based solvent.

65. The method of claim 11, wherein the one or more bridged polycyclic compounds are part of a composition, wherein the composition further comprises a solvent, and wherein the solvent comprises water and an alcohol based solvent.

66. The method of claim 11, wherein the one or more bridged polycyclic compounds are part of a composition, wherein the composition further comprises a solvent and a polymer, and wherein the solvent comprises water and an alcohol based solvent.

67. The method of claim 11, wherein the one or more bridged polycyclic compounds are part of a composition, wherein the composition further comprises a polymer and/or a polymerizable compound.

68. The method of claim 11, wherein at least one $R^3$ comprises a substituted aryl group.

69. The method of claim 11, wherein at least one $R^3$ comprises a substituted aryl group, wherein at least one of the substituted aryl group's substituents comprises a guanidinium group.

70. The method of claim 11, wherein each $R^3$ is independently an alkyl group, a substituted alkyl group, an aryl group, a substituted aryl group, a heterocycle group, a substituted heterocycle group, an alkene, an ether, a polyethyleneglycol, a benzyl group, a hydrogen, a hydrophilic group, or a polyethyleneimine and wherein at least one alkyl group comprises a C5-C7 alkyl group.

* * * * *